United States Patent
Pan et al.

(10) Patent No.: US 6,900,231 B2
(45) Date of Patent: May 31, 2005

(54) AMINOPYRIDYL-SUBSTITUTED PHENYL ACETAMIDES AS PROTEASE INHIBITORS

(75) Inventors: Wenxi Pan, Exton, PA (US); Tianbao Lu, Kennett Square, PA (US); Thomas P. Markotan, Morgantown, PA (US); Bruce E. Tomczuk, Collegeville, PA (US)

(73) Assignee: 3-Dimensional Pharmaceuticals, Inc., Exton, PA (US)

( * ) Notice: Subject to any disclaimer, the term of this patent is extended or adjusted under 35 U.S.C. 154(b) by 19 days.

(21) Appl. No.: 10/262,871

(22) Filed: Oct. 3, 2002

(65) Prior Publication Data

US 2003/0073833 A1 Apr. 17, 2003

Related U.S. Application Data

(62) Division of application No. 09/971,000, filed on Oct. 5, 2001, now Pat. No. 6,521,663.
(60) Provisional application No. 60/238,132, filed on Oct. 6, 2000.

(51) Int. Cl.⁷ .............. C07D 213/64; C07D 213/74; C07D 213/75; A61K 31/44
(52) U.S. Cl. .............. 514/349; 514/352; 546/283.7; 546/297; 546/309; 604/6.07; 604/600; 600/573
(58) Field of Search ................. 546/297, 309, 546/283.7; 514/349, 352; 604/6.07

(56) References Cited

U.S. PATENT DOCUMENTS

| | | | |
|---|---|---|---|
| 5,084,466 A | 1/1992 | Alig et al. | 514/353 |
| 5,676,923 A | 10/1997 | Platzek et al. | 424/4 |
| 5,721,214 A | 2/1998 | Marlowe et al. | 514/18 |
| 5,807,885 A | 9/1998 | Gentile et al. | 514/438 |
| 5,885,967 A | 3/1999 | Schacht et al. | 514/19 |
| 5,892,114 A | 4/1999 | Goldmann et al. | 564/161 |
| 6,034,272 A | 3/2000 | Commons et al. | 564/19 |
| 6,049,006 A | 4/2000 | Commons et al. | 564/19 |

FOREIGN PATENT DOCUMENTS

| | | |
|---|---|---|
| DE | 199 37 494 | 2/2001 |
| EP | 0560163 A1 | 9/1993 |
| EP | 0847992 A1 | 6/1998 |
| EP | 0937459 A2 | 8/1999 |
| JP | 8092234 | 4/1996 |
| WO | WO 94/29267 | 12/1994 |
| WO | 96/40100 | 12/1996 |
| WO | WO 97/01338 | 1/1997 |
| WO | WO 97/11693 | 4/1997 |
| WO | WO 97/30971 | 8/1997 |
| WO | WO 97/49404 | 12/1997 |
| WO | WO 98/17630 | 4/1998 |
| WO | WO 98/23565 | 6/1998 |
| WO | WO 98/35982 | 8/1998 |
| WO | WO 98/37061 | 8/1998 |
| WO | WO 98/57926 | 12/1998 |
| WO | WO 98/57929 | 12/1998 |
| WO | 99/26926 | 6/1999 |
| WO | 99/51571 | 10/1999 |
| WO | WO 99/55688 | 11/1999 |
| WO | WO 99/62893 | 12/1999 |
| WO | WO 01/68605 A1 | 9/2001 |

OTHER PUBLICATIONS

Dialog File 351, Accession No. 10739102, Derwent WPI English language abstract for JP 8092224.

*Primary Examiner*—Bernard Dentz
(74) *Attorney, Agent, or Firm*—Woodcock Washburn LLP

(57) ABSTRACT

Phenyl acetamide compounds are described, including compounds of

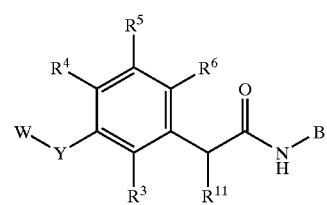

I or a solvate, hydrate or pharmaceutically acceptable salt thereof; wherein $R^3$–$R^6$, $R^{11}$, B, Y and W are set forth in the specification. The compounds of the invention are potent inhibitors of proteases, especially trypsin-like serine proteases, such as thrombin and factor Xa. Compositions for inhibiting loss of blood platelets, inhibiting formation of blood platelet aggregates, inhibiting formation of fibrin, inhibiting thrombus formation, and inhibiting embolus formation are described. Other uses of compounds of the invention are as anticoagulants either embedded in or physically linked to materials used in the manufacture of devices used in blood collection, blood circulation, and blood storage, such as catheters, blood dialysis machines, blood collection syringes and tubes, blood lines and stents. Additionally, the compounds can be detectably labeled and employed for in vivo imaging of thrombi.

30 Claims, No Drawings

AMINOPYRIDYL-SUBSTITUTED PHENYL ACETAMIDES AS PROTEASE INHIBITORS

The present application is a divisional of U.S. patent application Ser. No. 09/971,000, filed Oct. 5, 2001 now U.S. Pat. No. 6,521,663, which claims priority to Provisional Application No. 60/238,132, filed Oct. 6, 2000.

BACKGROUND OF THE INVENTION

1. Field of the Invention

The present invention relates to novel compounds that function as proteolytic enzyme inhibitors, and particularly to a new class of thrombin inhibitors.

2. Related Art

Proteases are enzymes that cleave proteins at single, specific peptide bonds. Proteases can be classified into four generic classes: serine, thiol or cysteinyl, acid or aspartyl, and metalloproteases (Cuypers et al., *J. Biol. Chem.* 257:7086 (1982)). Proteases are essential to a variety of biological activities, such as digestion, formation and dissolution of blood clots, reproduction and the immune reaction to foreign cells and organisms. Aberrant proteolysis is associated with a number of disease states in man and other mammals. The human neutrophil proteases, elastase and cathepsin G, have been implicated as contributing to disease states marked by tissue destruction. These disease states include emphysema, rheumatoid arthritis, corneal ulcers and glomerular nephritis. (Barret, in *Enzyme Inhibitors as Drugs*, Sandier, ed., University Park Press, Baltimore, (1980)). Additional proteases such as plasmin, C-1 esterase, C-3 convertase, urokinase, plasminogen activator, acrosin, and kallikreins play key roles in normal biological functions of mammals. In many instances, it is beneficial to disrupt the function of one or more proteolytic enzymes in the course of therapeutically treating a mammal.

Serine proteases include such enzymes as elastase (human leukocyte), cathepsin G, plasmin, C-1 esterase, C-3 convertase, urokinase, plasminogen activator, acrosin, chymotrypsin, trypsin, thrombin, factor Xa and kallikreins.

Human leukocyte elastase is released by polymorphonuclear leukocytes at sites of inflammation and thus is a contributing cause for a number of disease states. Cathepsin G is another human neutrophil serine protease. Compounds with the ability to inhibit the activity of these enzymes are expected to have an anti-inflammatory effect useful in the treatment of gout, rheumatoid arthritis and other inflammatory diseases, and in the treatment of emphysema. Chymotrypsin and trypsin are digestive enzymes. Inhibitors of these enzymes are useful in treating pancreatitis. Inhibitors of urokinase and plasminogen activator are useful in treating excessive cell growth disease states, such as benign prostatic hypertrophy, prostatic carcinoma and psoriasis.

The serine protease thrombin occupies a central role in hemostasis and thrombosis, and as a multifactorial protein, induces a number of effects on platelets, endothelial cells, smooth muscle cells, leukocytes, the heart, and neurons. Activation of the coagulation cascade through either the intrinsic pathway (contact activation) or the extrinsic pathway (activation by exposure of plasma to a non-endothelial surface, damage to vessel walls or tissue factor release) leads to a series of biochemical events that converge on thrombin. Thrombin cleaves fibrinogen ultimately leading to a hemostatic plug (clot formation), potently activates platelets through a unique proteolytic cleavage of the cell surface thrombin receptor (Coughlin, *Seminars in Hematology* 31(4) :270–277 (1994)), and autoamplifies its own production through a feedback mechanism. Thus, inhibitors of thrombin function have therapeutic potential in a host of cardiovascular and non-cardiovascular diseases.

Factor Xa is another serine protease in the coagulation pathway. Factor Xa associates with factor Va and calcium on a phospholipid membrane thereby forming a prothrombinase complex. This prothrombinase complex then converts prothrombin to thrombin (Claeson, *Blood Coagulation and Fibrinolysis* 5:411–436 (1994); Harker, *Blood Coagulation and Fibrinolysis* 5 (Suppl 1):S47–S58 (1994)). Inhibitors of factor Xa are thought to offer an advantage over agents that directly inhibit thrombin since direct thrombin inhibitors still permit significant new thrombin generation (Lefkovits and Topol, *Circulation* 90(3):1522–1536 (1994); Harker, *Blood Coagulation and Fibrinolysis* 5 (Suppl 1):S47–S58 (1994)).

In vivo diagnostic imaging methods for intravascular thrombi have been previously reported. These imaging methods use compounds that are detectably labeled with radioactive or paramagnetic atoms. For example, platelets labeled with the gamma emitter, In-111, can be employed as an imaging agent for detecting thrombi (Thakur, M. L. et al., *Thromb Res.* 9:345 (1976); Powers et al., *Neurology* 32:938 (1982)). The thrombolytic enzyme streptokinase labeled with Tc-99m has been proposed as an imaging agent (Wong, U.S. Pat. No. 4,418,052 (1983)). The fibrin-binding domains of *Staphylococcus aureus* derived protein A labeled with the gamma emitters, I-125 and I-131, have been proposed as imaging agents (Pang, U.S. Pat. No. 5,011,686 (1991)). Monoclonal antibodies having specificity for fibrin (in contrast to fibrinogen) and labeled with Tc-99m have been proposed as imaging agents (Berger et al., U.S. Pat. No. 5,024,829 (1991); Dean et al., U.S. Pat. No. 4,980,148 (1990)). The use of the paramagnetic contrasting agent, gadolinium diethylenetriaminepentaacetic acid in magnetic resonance imaging of patients treated by thrombolysis for acute myocardial infarction has been reported (De Roos, A. et al., *Int. J. Card. Imaging* 7:133 (1991)). Radiolabeled and paramagnetically labeled alpha-ketoamide derivatives have also been proposed as thrombus imaging agents (Abelman et al., U.S. Pat. No. 5,656,600).

A need continues to exist for non-peptidic compounds that are potent and selective protease inhibitors, and which possess greater bioavailability and fewer side-effects than currently available protease inhibitors. Accordingly, new classes of potent protease inhibitors, characterized by potent inhibitory capacity and low mammalian toxicity, are potentially valuable therapeutic agents for a variety of conditions, including treatment of a number of mammalian proteolytic disease states.

SUMMARY OF THE INVENTION

The present invention is directed to novel aminopyridinyl-, aminoguanidinyl-, and alkoxyguanidinyl-substituted phenyl acetamides having Formula I (below). Also provided are processes for preparing compounds of Formula I. The novel compounds of the present invention are potent inhibitors of proteases, especially trypsin-like serine proteases, such as chymotrypsin, trypsin, thrombin, plasmin and factor Xa. Certain of the compounds exhibit antithrombotic activity via direct, selective inhibition of thrombin, or are intermediates useful for forming compounds having antithrombotic activity. Also provided are methods of inhibiting or treating aberrant proteolysis in a mammal and methods of treating thrombosis, ischemia, stroke, restenosis or inflammation in a mammal by administering an effective amount of a compound of Formula I.

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

Also provided are methods of inhibiting or treating aberrant proteolysis in a mammal, and methods for treating myocardial infarction; unstable angina; stroke; restenosis; deep vein thrombosis; disseminated intravascular coagulation caused by trauma, sepsis or tumor metastasis; hemodialysis; cardiopulmonary bypass surgery; adult respiratory distress syndrome; endotoxic shock; rheumatoid arthritis; ulcerative colitis; induration; metastasis; hypercoagulability during chemotherapy; Alzheimer's disease; Down's syndrome; fibrin formation in the eye; and wound healing. Other uses of compounds of the invention are as anticoagulants either embedded in or physically linked to materials used in the manufacture of devices used in blood collection, blood circulation, and blood storage, such as catheters, blood dialysis machines, blood collection syringes and tubes, blood lines and stents.

The invention also includes a method for reducing the thrombogenicity of a surface in a mammal by attaching to the surface, either covalently or noncovalently, a compound of the invention.

In another aspect, the present invention includes compositions which are useful for in vivo imaging of thrombi in a mammal, comprising a compound of the present invention which is capable of being detected outside the body. Preferred are compositions comprising a compound of the present invention and a detectable label, such as a radioactive or paramagnetic atom.

In another aspect, the present invention provides diagnostic compositions which are useful for in vivo imaging of thrombi in a mammal, comprising a pharmaceutically acceptable carrier and a diagnostically effective amount of a compound or composition of the present invention.

In another aspect, the present invention includes methods which are useful for in vivo imaging of thrombi in a mammal.

DETAILED DESCRIPTION OF THE PREFERRED EMBODIMENTS

Compounds of the present invention include compounds of Formula I:

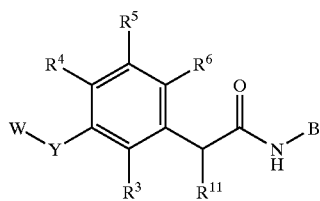

or a solvate, hydrate or pharmaceutically acceptable salt thereof; wherein:

W is hydrogen, $R^1$, $R^1OC(O)$, $R^1C(O)$, $R^1(CH_2)_sNHC(O)$, $R^1S(O)_2$, or $(R^1)_2CH(CH_2)_sNHC(O)$, wherein s is 0–4;

$R^1$ is $R^2$, $R^2(CH_2)_tC(R^{12})_2$, where t is 0–3, and each $R^{12}$ can be the same or different, $(R^2)_2(OR^{12})CH(CH_2)_p$, where p is 1–4, $(R^2)_2(OR^{12})C(CH_2)_p$, where p is 1–4, $R^2C(R^{12})_2(CH_2)_t$, wherein t is 0–3, and each $R^{12}$ can be the same or different, wherein $(R^{12})_2$ can also form a ring with C represented by $C_{3-9}$ cycloalkyl, $R^2CF_2C(R^{12})_2(CH_2)_q$, wherein q is 0–2, and each $R^{12}$ can be the same or different, wherein $(R^{12})_2$ can also form a ring with C represented by $C_{3-9}$ cycloalkyl, $R^2CH_2C(R^{12})_2(CH_2)_q$, wherein q is 0–2, and each $R^{12}$ can be the same or different, wherein $(R^{12})_2$ can also form a ring with C represented by $C_{3-9}$ cycloalkyl, $(R^2)_2CH(CH_2)_r$, where r is 0–4 and each $R^2$ can be the same or different, and wherein $(R^2)_2$ can also form a ring with CH represented by $C_{3-9}$ cycloalkyl, $C_{7-12}$ bicylic alkyl, $C_{10-16}$ tricylic alkyl, or a 5- to 7-membered mono- or bicyclic heterocyclic ring which can be saturated or unsaturated, and which contains from one to three heteroatoms selected from the group consisting of N, O and S, $R^2O(CH_2)_p$, wherein p is 2–4, $(R^2)_2CF(CH_2)_r$, wherein r is 0–4 and each $R^2$ can be the same different, wherein $(R^2)_2$ can also form a ring with C represented by $C_{3-9}$ cycloalkyl, $C_{7-12}$ bicyclic alkyl, $C_{10-16}$ tricyclic alkyl, or a 5- to 7-membered mono- or bicyclic heterocyclic ring which can be saturated or unsaturated, and which contains from one to three heteroatoms selected from the group consisting of N, O and S,

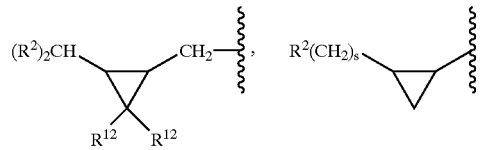

where s is 0 or 1, or $R^2CF_2C(R^{12})_2$;

$R^2$ is phenyl, naphthyl, or biphenyl, each of which is unsubstituted or substituted with one or more of $C_{1-4}$ alkyl, $C_{1-4}$ alkoxy, halogen, hydroxy, $CF_3$, $OCF_3$, COOH, $CONH_2$, or $SO_2NH_2$, a 5- to 7-membered mono- or a 9- to 10-membered bicyclic heterocyclic ring or non-heterocyclic ring which can be saturated or unsaturated, wherein the heterocyclic ring contains from one to four heteroatoms selected from the group consisting of N, O and S, and wherein the heterocyclic or non-heterocyclic ring is unsubstituted or substituted with halogen or hydroxy, $C_{1-12}$ alkyl, unsubstituted or substituted with one or more of hydroxy, COOH, amino, optionally $C_{1-3}$ alkyl substituted aryl, $C_{3-9}$ cycloalkyl, $CF_3$, $N(CH_3)_2$, heteroaryl, or heterocycloalkyl, $CF_3$, $C_{3-9}$ cycloalkyl, unsubstituted or substituted with aryl, $C_{7-12}$ bicyclic alkyl, or $C_{10-16}$ tricyclic alkyl;

Y is —NH— or —O—;

$R^3$, $R^4$, $R^5$ and $R^6$ are independently hydrogen, alkyl, cycloalkyl, alkenyl, alkynyl, optionally substituted aryl, optionally substituted aralkyl, optionally substituted heteroaryl, haloalkyl, hydroxy, alkoxy, aryloxy, heteroaryloxy, halogen, haloalkoxy, hydroxyalkyl, cyano, nitro, —$CO_2R^x$, —$CH_2OR^x$ or —$OR^x$, where $R^x$, in each instance, is independently one of hydrogen, $C_{1-12}$ alkyl or $C_{3-9}$ cycloalkyl wherein said $C_{1-12}$ alkyl or $C_{3-9}$ cycloalkyl groups may optionally have one or more unsaturations;

$R^{11}$ is hydrogen, alkyl, or alkenyl;

$R^{12}$ is hydrogen or halogen, phenyl, naphthyl, or biphenyl, each of which is unsubstituted or substituted with one or more of $C_{1-4}$ alkyl, $C_{1-4}$ alkoxy, halogen, hydroxy, $CF_3$, $OCF_3$, COOH, or $CONH_2$, a 5- to 7-membered mono- or a 9- to 10-membered bicyclic heterocyclic ring which can be saturated or unsaturated, and which contains from one to four heteroatoms selected from the group consisting of N, O and S, $C_{1-12}$ alkyl, unsubstituted or substituted with one or more of hydroxy, COOH, amino, $C_{6-14}$ aryl, heteroaryl, or heterocycloalkyl, $CF_3$, $C_{3-9}$ cycloalkyl, $C_{7-12}$ bicyclic alkyl, or $C_{10-16}$ tricyclic alkyl;

B is selected from the group consisting of:

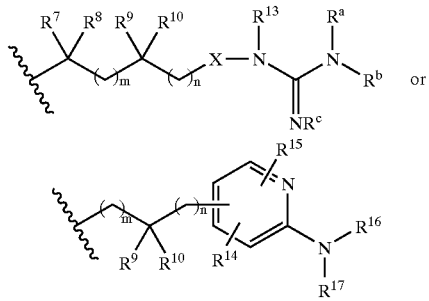

wherein $R^7$, $R^8$, $R^9$, and $R^{10}$ are independently hydrogen, alkyl, aralkyl, aryl, hydroxyalkyl, aminoalkyl, monoalkylaminoalkyl, dialkylaminoalkyl or carboxyalkyl;

or $R^7$ and $R^8$ are taken together to form —$(CH_2)_u$—, where u is 2 to 7, preferably 2 to 5, while $R^9$ and $R^{10}$ are defined as above;

or $R^9$ and $R^{10}$ are taken together to form —$(CH_2)_v$—, where v is 2 to 7, preferably 2 to 5, while $R^7$ and $R^8$ are defined as above;

or $R^7$ and $R^9$ are taken together to form —$(CH_2)_y$—, where y is 0 (a bond) or 1 to 7, preferably 0–4, while $R^8$ and $R^{10}$ are defined as above;

X is —O—, —$NR^{18}$—, or —CH═N— (where N is bonded to $NR^{13}$) where $R^{18}$ is hydrogen, alkyl, cycloalkyl or aryl, wherein said alkyl, cycloalkyl or aryl are optionally substituted with amino, monoalkylamino, dialkylamino, alkoxy, hydroxy, carboxy, alkoxycarbonyl, aryloxycarbonyl, aralkoxycarbonyl, aryl, heteroaryl, acylamino, cyano or trifluoromethyl;

$R^a$, $R^b$ and $R^c$ are independently hydrogen, alkyl, hydroxy, alkoxy, aryloxy, aralkoxy, alkoxycarbonyloxy, cyano or —$CO_2R^w$, where $R^w$ is $C_{1-12}$ alkyl, $C_{3-9}$ cycloalkyl, $C_{6-14}$ aryl, $C_{6-14}$ar($C_{1-12}$)alkyl,

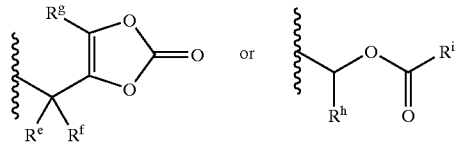

where $R^e$ and $R^f$ are independently hydrogen, $C_{1-6}$ alkyl, $C_{2-6}$ alkenyl or $C_{6-14}$ aryl, $R^8$ is hydrogen, $C_{1-6}$ alkyl, $C_{2-6}$ alkenyl or $C_{6-14}$ aryl, Rh is hydrogen, $C_{1-6}$alkyl, $C_{2-6}$ alkenyl or $C_{6-14}$ aryl, and $R^1$ is $C_{6-14}$ar($C_{1-12}$)alkyl or $C_{1-12}$ alkyl;

n is from zero to 8; and m is from zero to 6;

$R^{13}$ is hydrogen, alkyl, alkenyl, aralkyl, aryl, hydroxyalkyl, aminoalkyl, monoalkylaminoalkyl, dialkylaminoalkyl or carboxyalkyl;

$R^{14}$ and $R^{15}$ are independently hydrogen, alkyl, cycloalkyl, halogen or alkoxy; and $R^{16}$ and $R^{17}$ are independently hydrogen, alkyl, hydroxy, alkoxy, aryloxy, alkoxycarbonyl, cyano or —$CO_2R^1$, where $R^1$ is $C_{1-12}$ alkyl, $C_{3-9}$ cycloalkyl, $C_{6-14}$ aryl, $C_{6-14}$ar($C_{1-12}$)alkyl, halo($C_{1-12}$)alkyl or

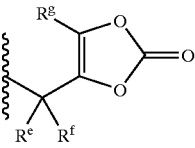

where $R^e$, $R^f$ and $R^g$ are independently hydrogen or $C_{1-12}$ alkyl.

Compounds within the scope of the present invention include those for which:

$R^3$, $R^4$, $R^5$ and $R^6$ are independently hydrogen, $C_{1-12}$ alkyl, $C_{3-9}$ cycloalkyl, halogen, $C_{2-20}$ alkenyl, $C_{2-20}$ alkynyl, optionally substituted $C_{6-14}$ aryl, optionally substituted $C_{6-14}$ar($C_{1-12}$)alkyl, optionally substituted heteroaryl, halo($C_{1-12}$)alkyl, $C_{1-12}$ alkoxy, $C_{6-14}$ aryloxy, heteroaryloxy, halo($C_{1-20}$)alkoxy or hydroxy ($C_{1-12}$)alkyl;

$R^{11}$ is hydrogen, $C_{1-12}$ alkyl or $C_{2-20}$ alkenyl;

$R^7$, $R^8$, $R^9$ and $R^{10}$ are independently hydrogen, $C_{1-12}$ alkyl, $C_{6-14}$ar($C_{1-12}$)alkyl, $C_{6-14}$ aryl, hydroxy($C_{1-12}$) alkyl, amino($C_{1-12}$)alkyl, mono($C_{1-12}$)alkylamino ($C_{1-2}$) alkyl, di($C_{1-12}$)alkylamino($C_{1-12}$)alkyl, or carboxy($C_{1-12}$)alkyl;

$R^{18}$ is $C_{1-2}$ alkyl, $C_{3-9}$ cycloalkyl or $C_{6-14}$ aryl, each of which is optionally substituted with amino, mono ($C_{1-12}$)alkylamino, di($C_{1-12}$)alkylamino, $C_{1-20}$ alkoxy, hydroxy, carboxy, $C_{1-20}$ alkoxycarbonyl, $C_{6-14}$ aryloxy carbonyl, $C_{6-14}$ ar($C_{1-20}$)alkoxycarbonyl, $C_{6-14}$ aryl, $C_{5-10}$ heteroaryl, acylamino, cyano or trifluoromethyl;

$R^a$, $R^b$ and $R^c$ are independently $C_{1-12}$ alkyl, $C_{1-20}$ alkoxy, $C_{6-14}$ aryloxy, $C_{6-14}$ar($C_{1-20}$)alkoxy, or $C_{1-20}$ alkoxycarbonyloxy;

$R^{13}$ is $C_{1-12}$ alkyl, $C_{1-20}$ alkoxy, $C_{6-14}$ aryloxy or $C_{1-20}$ alkoxycarbonyl;

$R^{14}$ and $R^{15}$ are independently $C_{1-12}$ alkyl, $C_{3-9}$ cycloalkyl or $C_{1-20}$ alkoxy; and $R^{16}$ and $R^{17}$ are independently $C_{1-12}$ alkyl, $C_{1-20}$ alkoxy, $C_{6-14}$ aryloxy or $C_{1-20}$ alkoxycarbonyl.

Preferred compounds of Formula I above are those for which Y is —NH— or —SO$_2$NH—.

A preferred subgenus of compounds of Formula I above are those for which B is

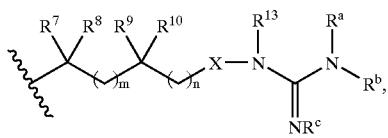

where $R^7$–$R^{10}$, $R^{13}$ and $R^a$–$R^c$ are as defined above

Another preferred subgenus of compounds of Formula I above are those for which B is

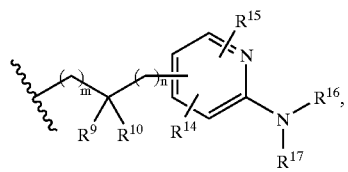

where $R^9$, $R^{10}$ and $R^{14}$–$R^{17}$ are as defined above.

Preferred compounds of Formula I above are those for which W is $R^1$, where $R^1$ is $R^2$ and $R^2$ is either optionally substituted phenyl, optionally substituted naphthyl or $C_{1-7}$ alkyl substituted with aryl.

Preferred compounds of Formula I above are those for which $R^1$ is $R^2CF_2C(R^{12})_2(CH_2)_q$.

Preferred compounds of Formula I above are those for which $R^6$ is $C_{1-6}$ alkyl or halogen. More preferred compounds within the third preferred subgenus are those for which $R^6$ is methyl or chloro, including compounds for which $R^6$ is chloro while $R^3$ is fluoro.

Preferred compounds of Formula I above are those for which $R^{11}$ is hydrogen.

Preferred values of $R^a$, $R^b$ and $R^c$ in Formula I are independently hydrogen, hydroxy, $C_{1-6}$alkyl, $C_{1-6}$ alkoxy, cyano or —CO$_2R^w$, where $R^w$, in each instance, is preferably one of $C_{1-4}$alkyl, $C_{1-7}$cycloalkyl or benzyloxycarbonyl. Suitable values of $R^a$, $R^b$ and $R^c$ include hydrogen, methyl, ethyl, propyl, n-butyl, hydroxy, methoxy, ethoxy, cyano, —CO$_2$CH$_3$, —CO$_2$CH$_2$CH$_3$ and —CO$_2$CH$_2$CH$_2$CH$_3$. In the most preferred embodiments, $R^a$, $R^b$ and $R^c$ are each hydrogen.

Also preferred at $R^a$, $R^b$ and $R^c$ is the group —CO$_2R^w$, where $R^w$ is one of

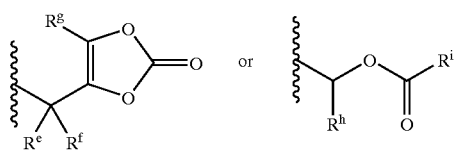

where $R^e$–$R^f$ are defined as above. When $R^a$, $R^b$ and $R^c$ are —CO$_2R^c$, where $R^w$ is one of one of these moieties, the resulting compounds are prodrugs that possess desirable formulation and bioavailability characteristics. A preferred value for each of $R^e$, $R^f$ and $R^h$ is hydrogen, $R^g$ is methyl, and preferred values for $R^i$ include benzyl and tert-butyl.

Preferred compounds are those of Formula I, where $R^7$, $R^8$, $R^9$ and $R^{10}$ are independently one of hydrogen, $C_{1-6}$ alkyl, $C_{6-10}$ ar($C_{1-6}$)alkyl, $C_{6-10}$ aryl, $C_{2-10}$ hydroxyalkyl or $C_{2-7}$ carboxyalkyl. Useful values of $R^7$, $R^8$, $R^9$ and $R^{10}$ include hydrogen, methyl, ethyl, propyl, n-butyl, benzyl, phenylethyl, 2-hydroxyethyl, 3-hydroxypropyl, 4-hydroxybutyl, 2-carboxymethyl, 3-carboxyethyl and 4-carboxypropyl. Additional preferred compounds are those where $R^7$ and $R^8$ or $R^9$ and $R^{10}$ are taken together to form —(CH$_2$)$_y$— where y is 2.

Preferred compounds when X is $NR^{18}$ are those wherein $R^{18}$ is hydrogen or $C_{1-6}$ alkyl, optionally substituted by one, two or three, preferably one, of amino, monoalkylamino, dialkylamino, alkoxy, hydroxy, alkoxycarbonyl, aryloxycarbonyl, aralkoxycarbonyl, carboalkoxy, phenyl, cyano, trifluoromethyl, acetylamino, pyridyl, thiophenyl, furyl, pyrrolyl or imidazolyl.

Suitable values of $R^{18}$ include hydrogen, methyl, ethyl, propyl, n-butyl, benzyl, phenethyl, 2-hydroxyethyl, 3-hydroxypropyl, 4-hydroxybutyl, carboxymethyl and carboxyethyl.

Most preferred compounds are those where X is oxygen.

$R^6$ can represent hydrogen, $C_{1-3}$ alkyl, halogen, or $C_{1-2}$ alkoxy. $R^6$ is preferably $C_{1-3}$ alkyl, e.g., methyl, or halogen, e.g., chlorine, bromine or fluorine.

$R^3$, $R^4$, $R^5$ and $R^6$ can independently represent hydrogen, hydroxy, $C_{1-3}$ alkyl, halogen, or $C_{1-2}$ alkoxy. Preferably $R^3$ is fluorine and hydroxy.

Preferred values of n in Formula I include from zero to 6, more preferably from zero to 4, and most preferably zero, 1 or 2. Preferred values of m include from zero to 4, more preferably zero, 1, 2 or 3.

It is also to be understood that the present invention is considered to include stereoisomers as well as optical isomers, e.g. mixtures of enantiomers as well as individual enantiomers and diastereomers, which arise as a consequence of structural asymmetry in selected compounds of the present series. The compounds of the present invention may also have polymorphic crystalline forms, with all polymorphic crystalline forms being included in the present invention.

The compounds of Formula I may also be solvated, especially hydrated. Hydration may occur during manufacturing of the compounds or compositions comprising the compounds, or the hydration may occur over time due to the hygroscopic nature of the compounds.

Certain compounds within the scope of Formula I are derivatives referred to as prodrugs. The expression "prodrug" denotes a derivative of a known direct acting drug, which derivative has enhanced delivery characteristics and therapeutic value as compared to the drug, and is transformed into the active drug by an enzymatic or chemical process. Useful prodrugs are those where $R^a$, Rb, $R^c$ and/or $R^d$ are —CO$_2R^w$, where $R^w$ is defined above. See, U.S. Pat. No. 5,466,811 and Saulnier et al., *Bioorg. Med. Chem. Lett.* 4:1985–1990 (1994).

When any variable occurs more than one time in any constituent or in Formula I, its definition on each occurrence is independent of its definition at every other occurrence. Also, combinations of substituents and/or variables are permissible only if such combinations result in stable compounds.

In another aspect, the present invention includes compositions which are useful for in vivo imaging of thrombi in a mammal, comprising a compound of the present invention which is capable of being detected outside the body. Preferred are compositions comprising a compound of the present invention and a detectable label, such as a radioactive or paramagnetic atom.

In another aspect, the present invention provides diagnostic compositions which are used for in vivo imaging of thrombi in a mammal, comprising a pharmaceutically acceptable carrier and a diagnostically effective amount of a compound or composition of the present invention.

In another aspect, the present invention includes methods which are useful for in vivo imaging of thrombi in a mammal.

According to a preferred aspect, useful compounds are those wherein the $R^1$ substituent is substituted with a detectable label, such as a radioactive iodine atom, such as I-125, I-131 or I-123. In this aspect, $R^1$ is preferably phenyl, having a para I-123, para I-125 or para I-131 substitution, or benzyl, having a meta I-123, meta I-125 or meta I-131 substitution.

The detectable label can also be a radioactive or paramagnetic chelate in which a suitable ligand (L) is attached to an $R^1$ substituent, either directly or via a divalent linking group A". Alternatively, the group —A"—L substitutes for the group W in Formula I. By suitable ligand is meant an organic moiety that is capable of chelating a radioactive or paramagnetic metal ion.

In these compounds, the divalent linking group A" includes groups that are capable of covalently bonding with a free amino group and the chelating means. For example, A" may be —C(=S)—, —C(=O)—, (=NH)—(CH$_2$)$_6$ (=NH)—, C(=O)+CH$_2$)$_6$—(=O),

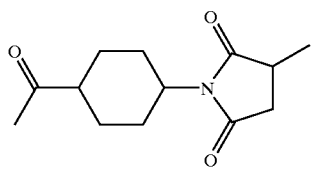

and the like.

Also, in the compounds represented by Formula I, the chelating ligand, L, includes groups capable of covalently bonding to or noncovalently binding to either a radioactive or paramagnetic atom. The chelating means including those which are customarily used for complexing radioactive or paramagnetic atoms. These include chelating means containing 3 to 12, preferably 3 to 8, methylene phosphonic acid groups, methylene carbohydroxamic acid groups, carboxyethylidene groups, or especially carboxymethylene groups, which are bonded to a nitrogen atom. If only one or two of the acid groups are bonded to a nitrogen atom, then that nitrogen is bonded to another nitrogen atom having such groups by an optionally substituted ethylene group or by up to four separated ethylene units separated by a nitrogen or oxygen or sulfur atom. Preferred as a completing means is diethylenetrimine-N,N,N',N",N"-pentaacetic acid (DTPA). DTPA is well known in the art as a chelating means for the radioactive atoms indium-111 (In-111), technetium-99m (Tc-99m), and the paramagnetic atom gadolinium (Gd). Khaw, et al., Science 209:295 (1980); Paik C. H. et al., U.S. Pat. No. 4,652,440 (1987); Gries, H. et al., U.S. Pat. No. 4,957,939 (1990). A preferred chelating ligand, L, is 1-(p-aminobenzyl)-diethylenetriaminepentaacetic acid. Also included as chelating means are compounds which contain sulfhdryl or amine moieties, the total of which in any combination is at least four. These sulfhydryl or amine moieties are separated from each other by at least two atoms which can be either carbon, nitrogen, oxygen, or sulfur. Especially preferred for chelating means, L, is metallothionein which is well known in the art as a chelating means for Tc-99m.

The term "alkyl" as employed herein by itself or as part of another group refers to both straight and branched chain radicals of up to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl. Preferably, alkyl is 1 to 6 carbon atoms.

The term "alkenyl" is used herein to mean a straight or branched chain radical of 2–20 carbon atoms, unless the chain length is limited thereto, including, but not limited to, ethenyl, 1-propenyl, 2-propenyl, 2-methyl-1-propenyl, 1-butenyl, 2-butenyl, and the like. Preferably, the alkenyl chain is 2 to 10 carbon atoms in length, more preferably, 2 to 8 carbon atoms in length most preferably from 2 to 4 carbon atoms in length.

The term "alkynyl" is used herein to mean a straight or branched chain radical of 2–20 carbon atoms, unless the chain length is limited thereto, wherein there is at least one triple bond between two of the carbon atoms in the chain, including, but not limited to, acetylene, 1-propylene, 2-propylene, and the like. Preferably, the alkynyl chain is 2 to 10 carbon atoms in length, more preferably, 2 to 8 carbon atoms in length, most preferably from 2 to 4 carbon atoms in length.

In all instances herein where there is an alkenyl or alkynyl moiety as a substituent group, the unsaturated linkage, i.e., the vinylene or acetylene linkage, is preferably not directly attached to a nitrogen, oxygen or sulfur moiety.

The term "alkoxy" is used herein to mean a straight or branched chain radical of 1 to 20 carbon atoms, unless the chain length is limited thereto, bonded to an oxygen atom, including, but not limited to, methoxy, ethoxy, n-propoxy, isopropoxy, and the like. Preferably the alkoxy chain is 1 to 10 carbon atoms in length, more preferably 1 to 8 carbon atoms in length.

The term "aryl" as employed herein by itself or as part of another group refers to monocyclic or bicyclic aromatic groups containing from 6 to 14 carbons in the ring portion, preferably 6–10 carbons in the ring portion, such as phenyl, naphthyl or tetrahydronaphthyl.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2, 3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "aralkyl" or "arylalkyl" as employed herein by itself or as part of another group, refers to $C_{1-12}$ alkyl, preferably $C_{1-6}$ alkyl, groups as discussed above having an aryl substituent, such as benzyl, phenylethyl or 2-naphthylmethyl.

The term "cycloalkyl" as employed herein by itself or as part of another group, refers to cycloalkyl groups containing 3 to 9 carbon atoms, preferably 3 to 7 carbon atoms. Typical examples are cyclopropyl, cyclobutyl, cyclopentyl, cyclohexyl, cycloheptyl, cyclooctyl and cyclononyl.

The term "$C_{7-12}$ bicyclic alkyl" is intended to include bicyclo[2.2.1]heptyl (norbornyl), bicyclo[2.2.2]octyl, 1,1,3-trimethylbicyclo[2.2.1]heptyl (bornyl), and the like.

The term "$C_{10-16}$ tricyclic alkyl" is intended to include tricyclo[5, 2, 1, $0^{2,6}$] decyl, adamantyl, and the like.

The term "halogen" or "halo" as employed herein by itself or as part of another group refers to chlorine, bromine, fluorine or iodine with chlorine and fluorine being preferred.

The term "monoalkylamine" as employed herein by itself or as part of another group refers to an amino group which is substituted with one alkyl group having from 1 to 12, preferably 1 to 6, carbon atoms.

The term "dialkylamine" as employed herein by itself or as part of another group refers to an amino group which is substituted with two alkyl groups, each having from 1 to 12, preferably 1 to 6, carbon atoms.

The term "hydroxyalkyl" as employed herein refers to any of the above alkyl groups substituted by one or more hydroxyl moieties.

The term "carboxyalkyl" as employed herein refers to any of the above alkyl groups substituted by one or more carboxylic acid moieties.

The term "heterocycle" or "heterocyclic ring", as used herein except where noted, represents a stable 5- to 7-membered mono- or bicyclic or stable 7- to 10-membered bicyclic heterocyclic ring system, any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Especially useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The term "heteroatom" is used herein to mean an oxygen atom ("O"), a sulfur atom ("S") or a nitrogen atom ("N"). It will be recognized that when the heteroatom is nitrogen, it may form an $NR^aR^b$ moiety, wherein $R^a$ and $R^b$ are, independently from one another, hydrogen or $C_1$ to $C_8$ alkyl, or together with the nitrogen to which they are bound, form a saturated or unsaturated 5-, 6-, or 7-membered ring.

Schemes 1–8 outline a synthetic route to compounds of Formula I

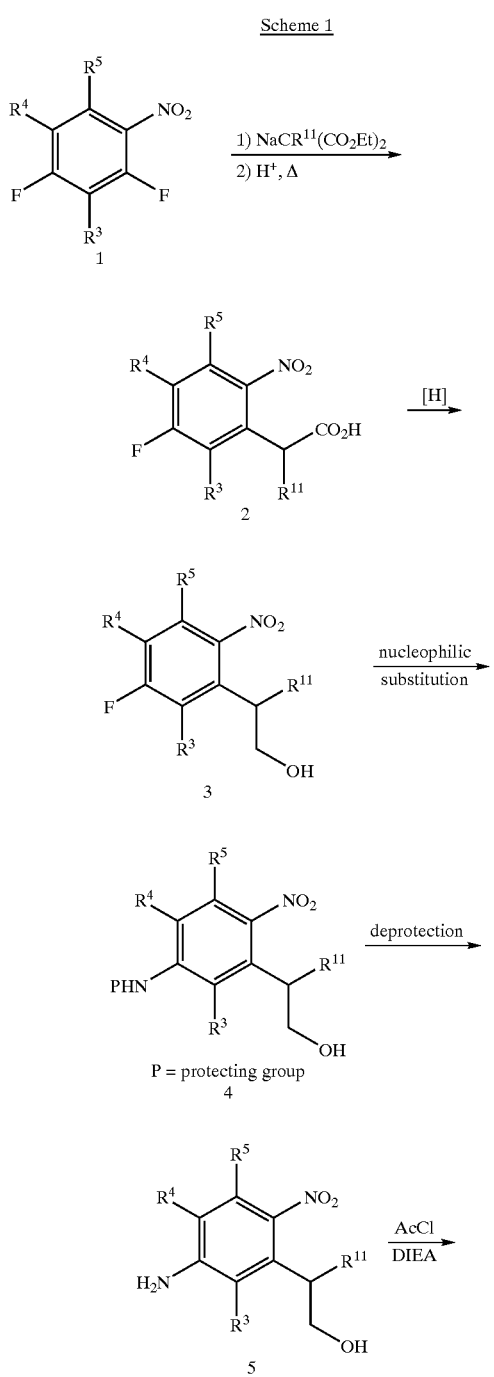

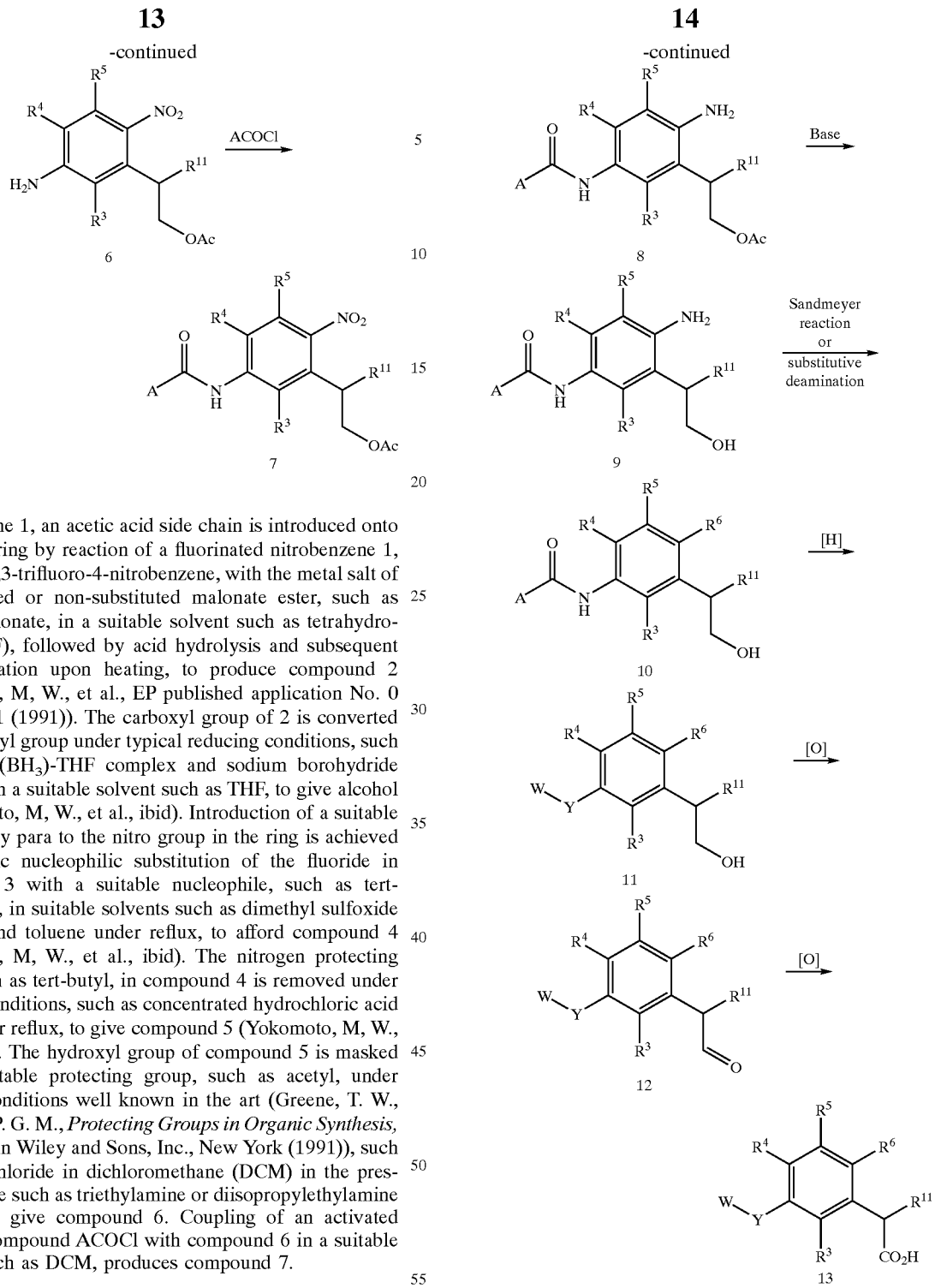

In Scheme 1, an acetic acid side chain is introduced onto a benzene ring by reaction of a fluorinated nitrobenzene 1, such as 1,2,3-trifluoro-4-nitrobenzene, with the metal salt of a substituted or non-substituted malonate ester, such as diethyl malonate, in a suitable solvent such as tetrahydrofuran (THF), followed by acid hydrolysis and subsequent decarboxylation upon heating, to produce compound 2 (Yokomoto, M, W., et al., EP published application No. 0 470 578 A1 (1991)). The carboxyl group of 2 is converted to a hydroxyl group under typical reducing conditions, such as borane (BH$_3$)-THF complex and sodium borohydride (NaBH$_4$), in a suitable solvent such as THF, to give alcohol 3 (Yokomoto, M, W., et al., ibid). Introduction of a suitable functionality para to the nitro group in the ring is achieved by aromatic nucleophilic substitution of the fluoride in compound 3 with a suitable nucleophile, such as tert-butylamine, in suitable solvents such as dimethyl sulfoxide (DMSO) and toluene under reflux, to afford compound 4 (Yokomoto, M, W., et al., ibid). The nitrogen protecting group, such as tert-butyl, in compound 4 is removed under standard conditions, such as concentrated hydrochloric acid (HCl) under reflux, to give compound 5 (Yokomoto, M, W., et al., ibid). The hydroxyl group of compound 5 is masked with a suitable protecting group, such as acetyl, under standard conditions well known in the art (Greene, T. W., and Wuts, P. G. M., *Protecting Groups in Organic Synthesis*, 2$^{nd}$ ed., John Wiley and Sons, Inc., New York (1991)), such as acetyl chloride in dichloromethane (DCM) in the presence of base such as triethylamine or diisopropylethylamine (DIEA), to give compound 6. Coupling of an activated carbonyl compound ACOCl with compound 6 in a suitable solvent, such as DCM, produces compound 7.

Scheme 2

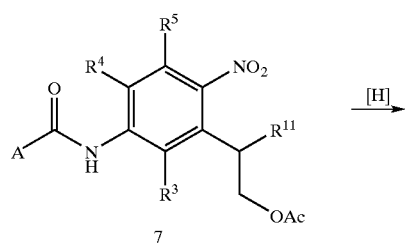

In Scheme 2, reduction of arylnitro compound 7 under typical conditions, such as catalytic hydrogenation with hydrogen in the presence of palladium on activated carbon in ethanol or methanol, gives arylamine 8. The acetyl protecting group of compound 8 is removed (in order to increase the solubility of the compound prior to the amino group manipulation) by hydrolysis under basic conditions, such as aqueous potassium carbonate (K$_2$CO$_3$) solution in methanol, to free the protected hydroxyl group, giving compound 9. The desired R$^6$ is introduced into the center scaffold of compound 9 by a Sandmeyer-type reaction ((a)

Gunstone, F. D., et al., *Org. Syn. Collect Vol.* 1, Wiley, New York, N.Y. (1941), p. 170; (b) Yokomoto, M, W., et al., EP published application No. 0 470 578 A1 (1991)) with suitable reagents, such as sodium nitrite ($NaNO_2$) and HCl followed by copper (I) chloride (CuCl), or by substitutive deamination (Doyle, M. P., et al. *J. Org. Chem.* 42:2426 (1977)) with suitable reagents, such as tert-butylnitrite (t-BuONO) and copper (II) chloride ($CuCl_2$), to give compound 10. The amino group of arylamine 9 can be converted to a methyl group under carbon—carbon coupling conditions in the presence of a palladium catalyst through an arenediazonium salt intermediate (Kikukawa, K., et al., *J. Org. Chem.* 48:1333 (1983)). Compound 10 in turn, is reduced with a suitable reducing agent, such as $BH_3$, to generate desired fragment WY of compound 11 where Y is —NH—. Oxidation of 11 with an oxidizing agent, such as sulfur trioxide pyridine complex ($SO_3$ pyridine) in DCM, yields aldehyde 12. Construction of the center and left fragment of the target compound is finally achieved by further oxidation of the aldehyde 12 to carboxylic acid 13 under suitable oxidation conditions, such as sodium chlorite ($NaClO_2$) in the presence of sodium dihydrogenphosphate ($NaH_2PO_4$) and DMSO (Dalcanale, E., et al., *J. Org. Chem.* 51:567 (1986)).

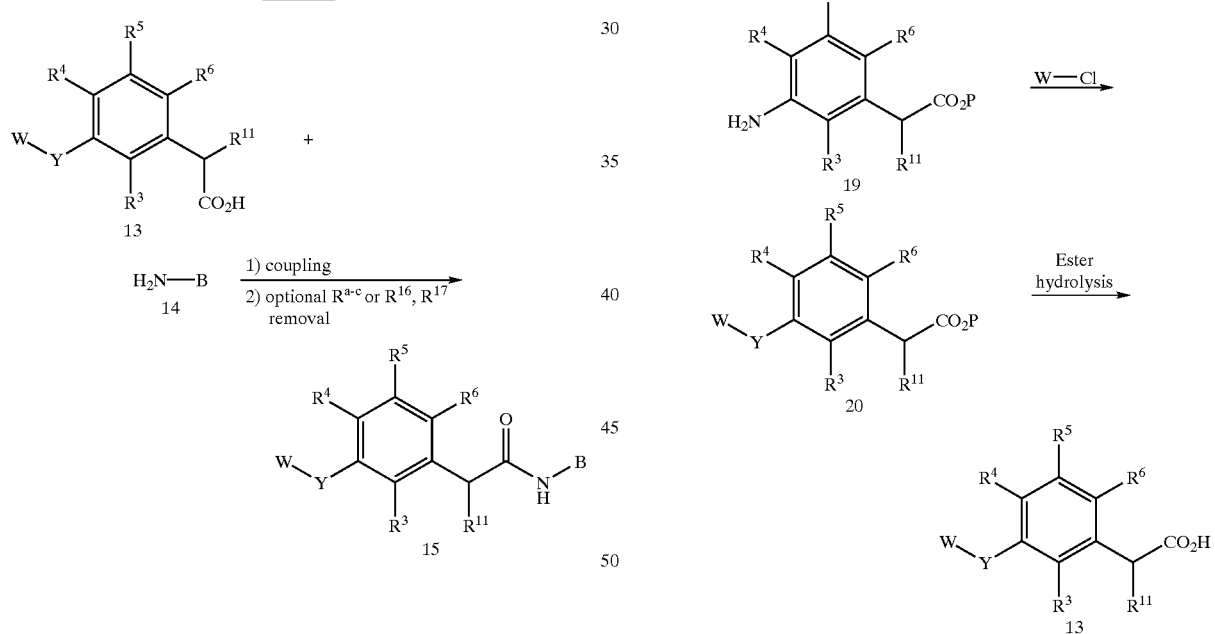

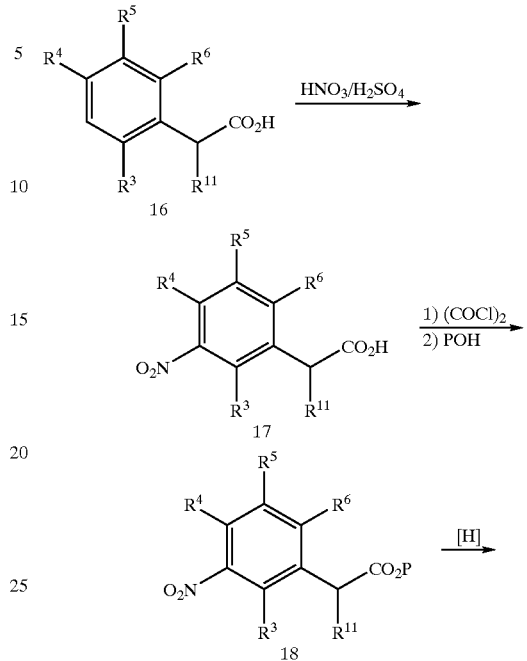

In Scheme 3, acid 13 is coupled with a suitable amine 14, such as protected O-guanidinyl amine (Tianbao Lu, et al., WO 99/26926 (1999)), or aminopyridinyl amine (Sanderson, P. E., et al., WO 97/01338 (1997)) in the presence of a typical peptide coupling reagent, such as Castro's reagent (BOP), and a base, such as DIEA, in a suitable solvent, such as N,N-dimethylformamide (DMF), to produce amide 15. Optionally, the protecting groups, such as tert-(butoxy)carbonyl (Boc), can be removed under typical deprotection conditions, such as trifluoroacetic acid (TFA) solution in DCM when B is O-guanidine, or HCl solution in 1,4-dioxane when B is aminopyridine, to generate free O-guanidine, or aminopyridine, respectively.

In Scheme 4, the phenylacetic acid derivative 16 is nitrated in the meta position of the benzene ring using standard conditions, such as 96% nitric acid in conc. sulfuric acid (Sindelar et al., *Coll. Czechoslov. Chem. Commun.* 42:2231 (1977)), to give the nitro compound 17. The carboxylic acid group of compound 17 is then protected using standard conditions well known in the art (Greene, T. W. and Wuts, P. G. M., *Protective Groups in Organic Synthesis*, 2$^{nd}$ ed., John Wiley and Sons, New York (1991)), such as conversion to the ester by reaction with oxalyl chloride followed by alcohol POH, to afford ester 18 (where P is a typical carboxylic acid protecting group). Reduction of the nitro group is accomplished using a suitable reagent, such as tin (II) chloride, in an appropriate solvent, such as ethanol, and the resulting amine 19 is reacted with an acylating agent (W=R¹C(O)) or a sulfonylating agent (W=R¹S(O)₂), such as benzylsulfonyl chloride, and a suitable base, such as N-methylmorpholine, in a solvent, such as DCM, to provide the N-substituted-aminophenylacetate 20 (Y=—NH—). The carboxylic acid group is deprotected using standard conditions well known in the art (Greene, T. W. and Wuts, P. G. M., *Protective Groups in Organic Synthesis*, 2$^{nd}$ edition, John Wiley and Sons, New York (1991)), such as hydrolysis with aqueous hydroxide, to give acid 13 (Y=—NH—). This is then coupled with amine 14 and deprotected, as in Scheme 3, to produce phenylacetamide 15 (Y=NH).

Scheme 5

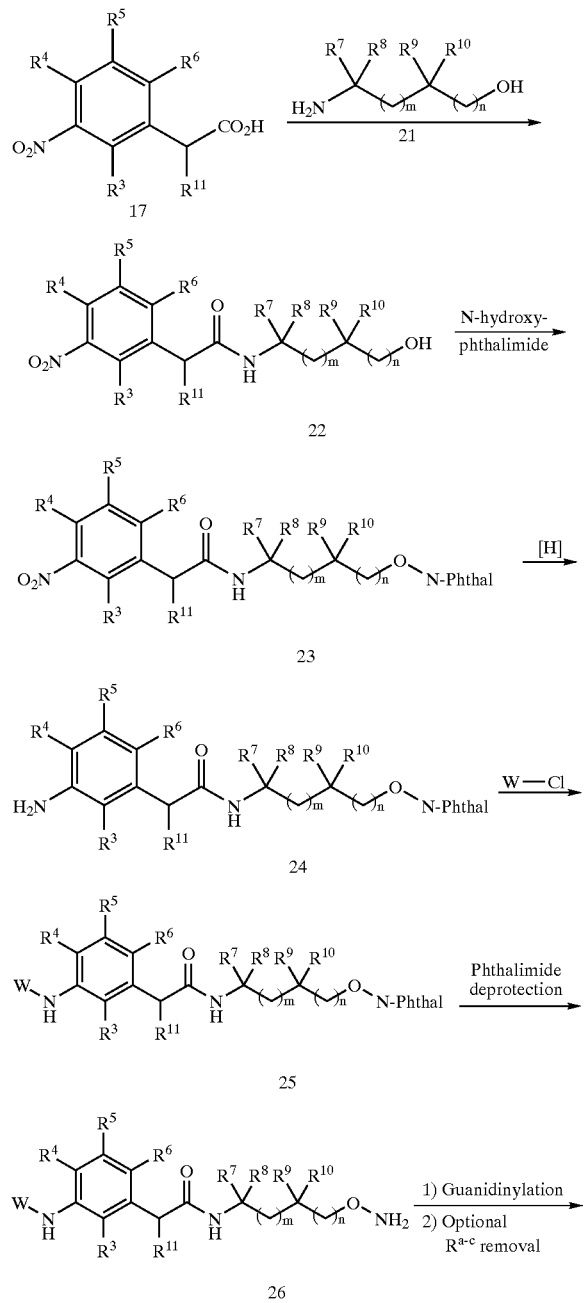

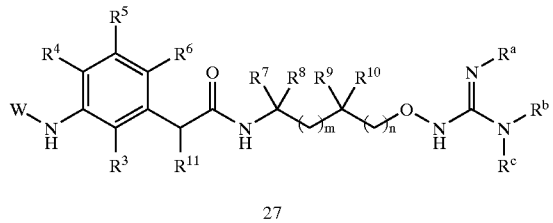

27

In Scheme 5, nitrophenylacetic acid 17 is coupled to an aminoalcohol 21, such as ethanolamine, using a standard peptide coupling procedure, such as in Scheme 3, to give alcohol 22. The alcohol is converted to the protected alkoxyamine by coupling to N-hydroxyphthalimide using standard reagents (Mitsunobu, O., *Synthesis* 1:1 (1981)), such as triphenylphosphine and diethylazodicarboxylate, in a suitable solvent, such as THF, to afford compound 23, which is then converted to aniline 24 under typical reducing conditions, such as hydrogenation over palladium(0) on carbon, in a suitable solvent, such as ethanol. The amine is then acylated or sulfonylated as in Scheme 4 to give intermediate 25, and the alkoxyamine deprotected using standard conditions well known in the art (Greene, T. W. and Wuts, P. G. M., *Protective Groups in Organic Synthesis*, 2$^{nd}$ edition, John Wiley and Sons, New York (1991)), such as aqueous methylamine in ethanol/THF. Guanidinylation of the resulting alkoxyamine 26 is accomplished with a standard guanidinylation reagent, such as N,N'-bis(tert-butoxycarbonyl)-S-methylthiourea (Bergeron, R. J. and McManis, J. S., *J. Org. Chem.* 52:1700 (1987)) or N-R$^a$-N'-R$^b$, R$^c$-1H-pyrazole-1-carboxamidine (Bernatowicz, M. S. et al. *Tetrahedron Lett.* 34:3389 (1993)), and the guanidine optionally deprotected as in Scheme 3, to provide final target 27.

Scheme 6

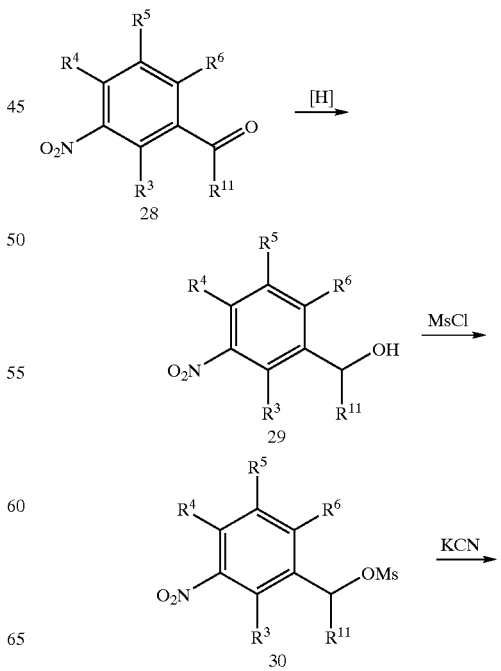

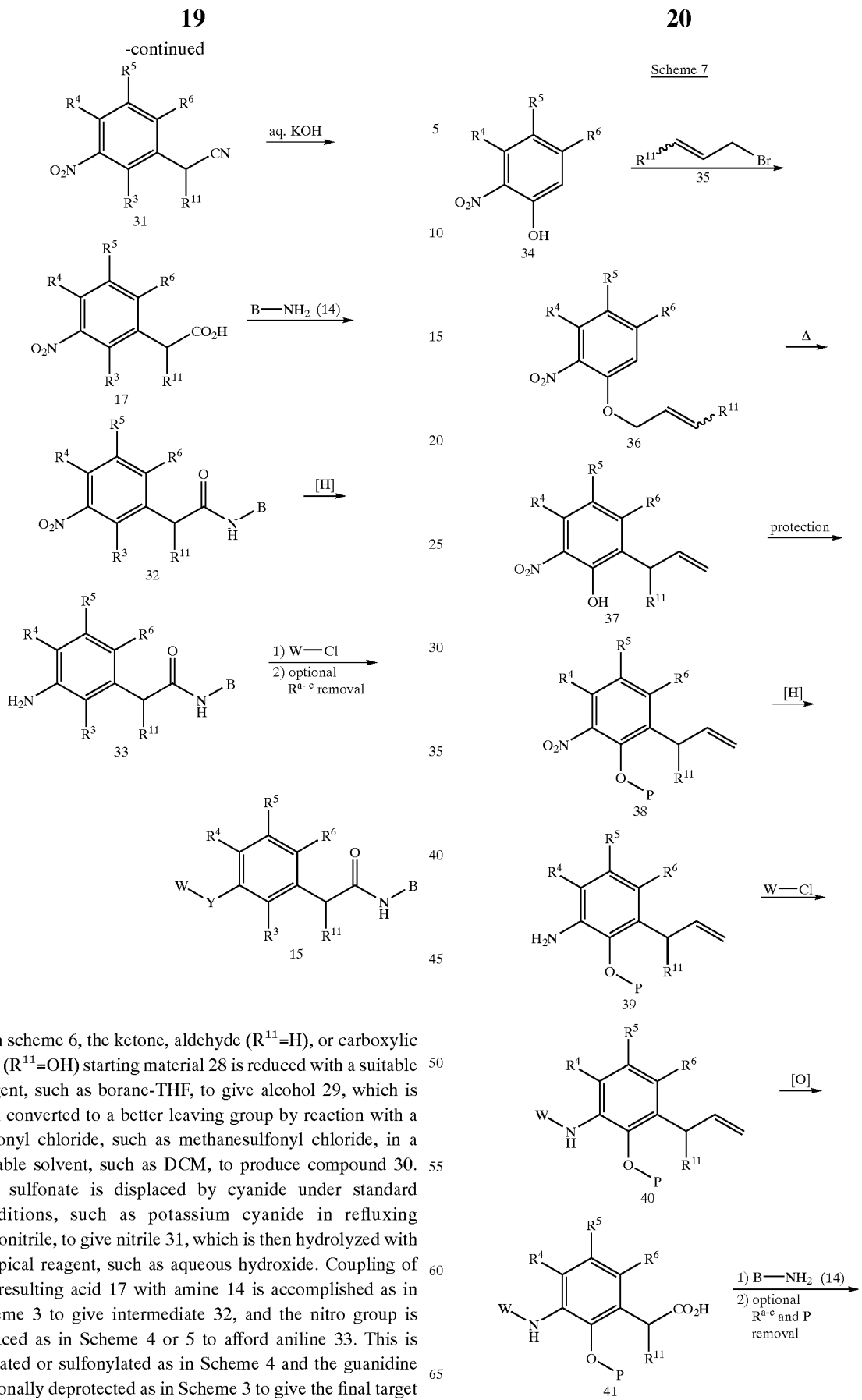

Scheme 7

In scheme 6, the ketone, aldehyde ($R^{11}$=H), or carboxylic acid ($R^{11}$=OH) starting material 28 is reduced with a suitable reagent, such as borane-THF, to give alcohol 29, which is then converted to a better leaving group by reaction with a sulfonyl chloride, such as methanesulfonyl chloride, in a suitable solvent, such as DCM, to produce compound 30. The sulfonate is displaced by cyanide under standard conditions, such as potassium cyanide in refluxing acetonitrile, to give nitrile 31, which is then hydrolyzed with a typical reagent, such as aqueous hydroxide. Coupling of the resulting acid 17 with amine 14 is accomplished as in scheme 3 to give intermediate 32, and the nitro group is reduced as in Scheme 4 or 5 to afford aniline 33. This is acylated or sulfonylated as in Scheme 4 and the guanidine optionally deprotected as in Scheme 3 to give the final target 15 (Y=NH).

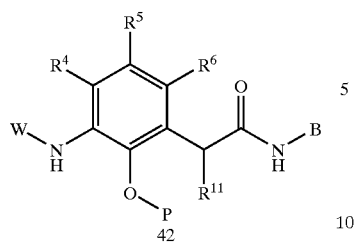

42

In Scheme 7, nitrophenol 34 is alkylated with allylic halide 35 and a suitable base, such a cesium carbonate, in a polar aprotic solvent, such as DMF, giving intermediate 36, which is then converted to compound 37 via the aromatic Claisen rearrangement by heating. The phenol is protected using typical reagents, such as benzyl bromide and cesium carbonate, in a solvent, such as DMF, to give 38 (where P is a typical hydroxyl protecting group) and the nitro group is reduced as in Scheme 4 or 5 to produce aniline 39. Aniline 39 is converted to intermediate 40 as in Scheme 4 and the alkene is oxidatively cleaved using standard conditions, such as sodium periodate and osmium tetraoxide in dioxane/water followed by Jones reagent, to provide acid 41. This is then coupled to amine 14, the guanidine optionally deprotected as in Scheme 3, and the phenol group optionally deprotected using standard conditions, such as hydrogenation over palladium (0) on carbon, in a suitable solvent, such as ethanol, to produce the target compound 42.

Scheme 8

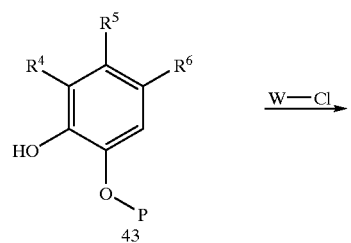

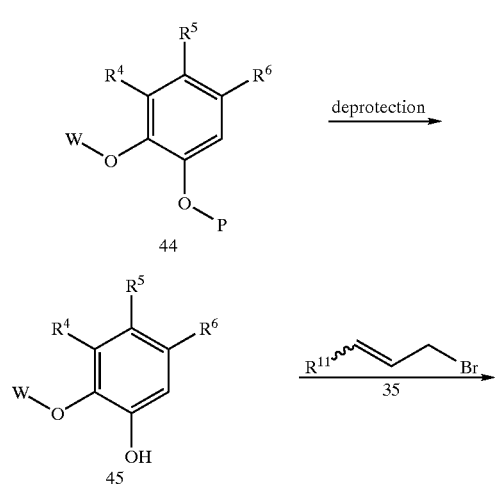

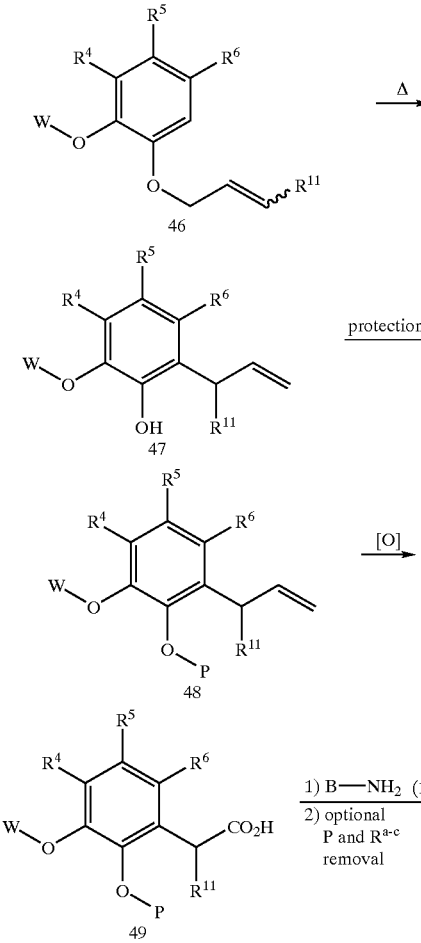

In Scheme 8, the mono-protected catechol 43 is sulfonylated with a reagent W—Cl, such as meta-toluenesulfonyl chloride, in a solvent, such as DCM, in the presence of a base, such as triethylamine, giving compound 44. The protecting group is removed using standard conditions, such as boron tribromide in DCM, and the resulting phenol 45 is alkylated with allylic halide 35 to give 46, rearranged to phenol 47, and protected to afford intermediate 48 as in Scheme 7. The alkene is oxidatively cleaved using standard conditions, such as sodium periodate and ruthenium(III) chloride in acetonitrile/water (Ashby, E. C. and Goel, A. B., *J. Org. Chem.* 46:3936 (1981)) followed by Jones reagent, giving acid 49, which is then coupled with amine 14 and optionally deprotected as in Schemes 3 and 7 to afford target compound 50.

The pharmaceutically-acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, trifluoroacetate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth, including salts with a guanidinyl moiety. Also, the basic nitrogen-containing groups may be quaternized with such agents as lower alkyl halides, such as methyl, ethyl, propyl, and butyl chlorides, bromides and iodides; dialkyl sulfates like dimethyl, diethyl, dibutyl, and diamyl sulfates; long chain halides such as decyl, lauryl, myristyl and stearyl chlorides, bromides and iodides; aralkyl halides like benzyl and phenethyl bromides and others. Preferred acids for forming acid addition salts include HCl, acetic acid and trifluoroacetic acid.

The compounds of the present invention represent a novel class of potent inhibitors of metallo, acid, thiol and serine proteases. Examples of the serine proteases inhibited by compounds within the scope of the invention include leukocyte neutrophil elastase, a proteolytic enzyme implicated in the pathogenesis of emphysema; chymotrypsin and trypsin, digestive enzymes; pancreatic elastase, and cathepsin G, a chymotrypsin-like protease also associated with leukocytes; thrombin and factor Xa, proteolytic enzymes in the blood coagulation pathway. Inhibition of thermolysin, a metalloprotease, and pepsin, an acid protease, are also contemplated uses of compounds of the present invention. The compounds of the present invention are preferably employed to inhibit trypsin-like proteases.

For their end-use application, the potency and other biochemical parameters of the enzyme-inhibiting characteristics of the compounds of the present invention are readily ascertained by standard biochemical techniques known to those of skill in the art. For example, an end use application of the compounds that inhibit chymotrypsin and trypsin is in the treatment of pancreatitis. Actual dose ranges for their specific end-use application will, of course, depend upon the nature and severity of the disease state of the patient or animal to be treated, as determined by the attending diagnostician. It is expected that a useful dose range will be about 0.01 to 10 mg per kg per day for an effective therapeutic effect.

Compounds of the present invention that are distinguished by their ability to inhibit thrombin may be employed for a number of therapeutic purposes. As thrombin inhibitors, compounds of the present invention inhibit thrombin production. Therefore, these compounds are useful for the treatment or prophylaxis of states characterized by abnormal venous or arterial thrombosis involving either thrombin production or action. These states include, but are not limited to, deep vein thrombosis; disseminated intravascular coagulopathy which occurs during septic shock, viral infections and cancer; myocardial infarction; stroke; coronary artery bypass; fibrin formation in the eye; hip replacement; and thrombus formation resulting from either thrombolytic therapy or percutaneous transluminal coronary angioplasty (PCTA). Other uses include the use of said thrombin inhibitors as anticoagulants either embedded in or physically linked to materials used in the manufacture of devices used in blood collection, blood circulation, and blood storage, such as catheters, blood dialysis machines, blood collection syringes and tubes, and blood lines. The compounds of the present invention may also be used as an anticoagulant in extracorporeal blood circuits.

Stents have been shown to reduce restenosis, but are thrombogenic. A strategy for reducing the thrombogenicity of stents is to coat, embed, adsord or covalently attach a thrombin-inhibiting agent to the stent surface. The compounds of the present invention can be employed for this purpose. Compounds of the invention can be attached to, or embedded within soluble and/or biodegradeable polymers as and thereafter coated onto stent materials. Such polymers can include polyvinylpyrrolidone, polyhydroxy-propylmethacrylamide-phenol, polyhydroxyethyl-aspartamide-phenol, or polyethyleneoxide-polylysine substituted with palmitoyl residues, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. See European Application 761 251, European Application 604,022, Canadian Patent No. 2,164,684 and PCT Published Applications Nos. WO 96/11668, WO 96/32143 and WO 96/38136.

By virtue of the effects of thrombin on a host of cell types, such as smooth muscle cells, endothelial cells and neutrophils, the compounds of the present invention find additional use in the treatment or prophylaxis of adult respiratory distress syndrome; inflammatory responses; wound healing; reperfusion damage; atherosclerosis; and restenosis following an injury such as balloon angioplasty, atherectomy, and arterial stent placement.

The compounds of the present invention may be useful in treating neoplasia and metastasis as well as neurodegenerative diseases, such as Alzheimer's disease and Parkinson's disease.

When employed as thrombin inhibitors, the compounds of the present invention may be administered in an effective amount within the dosage range of about 0.1 to about 500 mg/kg, preferably between 0.1 to 10 mg/kg body weight, on a regimen in single or 2–4 divided daily doses.

When employed as inhibitors of thrombin, the compounds of the present invention may be used in combination with thrombolytic agents such as tissue plasminogen activator, streptokinase, and urokinase. Additionally, the compounds of the present invention may be used in combination with other antithrombotic or anticoagulant drugs such as, but not limited to, fibrinogen antagonists and thromboxane receptor antagonists.

The thrombin inhibitors may also be coupled with soluble polymers as targetable drug carriers. Such polymers can include polyvinylpyrrolidone, pyran copolymer, polyhydroxy-propylmethacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

Human leucocyte elastase is released by polymorphonuclear leukocytes at sites of inflammation and thus is a contributing cause for a number of disease states. Compounds of the present invention are expected to have an anti-inflammatory effect useful in the treatment of gout, rheumatoid arthritis and other inflammatory diseases, and in the treatment of emphysema. The leucocyte elastase inhibitory properties of compounds of the present invention are determined by the method described below. Cathepsin G has also been implicated in the disease states of arthritis, gout and emphysema, and in addition, glomerulonephritis and lung infestations caused by infections in the lung. In their end-use application the enzyme inhibitory properties of the compounds of Formula I are readily ascertained by standard biochemical techniques that are well-known in the art.

The Cathepsin G inhibitory properties of compounds within the scope of the present invention are determined by the following method. A preparation of partially purified human Cathepsin G is obtained by the procedure of Baugh et al., *Biochemistry* 15: 836 (1979). Leukocyte granules are a major source for the preparation of leukocyte elastase and cathepsin G (chymotrypsin-like activity). Leukocytes are lysed and granules are isolated. The leukocyte granules are extracted with 0.20 M sodium acetate, pH 4.0, and extracts are dialyzed against 0.05 M Tris buffer, pH 8.0 containing 0.05 M NaCl overnight at 4° C. A protein fraction precipitates during dialysis and is isolated by centrifugation. This fraction contains most of the chymotrypsin-like activity of leukocyte granules. Specific substrates are prepared for each enzyme, namely N-Suc-Ala-Ala-Pro-Val-p-nitroanilide and Suc-Ala-Ala-Pro-Phe-p-nitroanilide. The latter is not hydrolyzed by leukocyte elastase. Enzyme preparations are assayed in 2.00 mL of 0.10 M Hepes buffer, pH 7.5, containing 0.50 M NaCl, 10% dimethylsulfoxide and 0.0020 M Suc-Ala-Ala-Pro-Phe-p-nitroanilide as a substrate. Hydrolysis of the p-nitroanilide substrate is monitored at 405 nm and at 25° C.

Useful dose range for the application of compounds of the present invention as neutrophil elastase inhibitors and as Cathepsin G inhibitors depend upon the nature and severity of the disease state, as determined by the attending diagnostician, with a range of 0.01 to 10 mg/kg body weight, per day, being useful for the aforementioned disease states.

Compounds of the present invention that inhibit urokinase or plasminogen activator are potentially useful in treating excessive cell growth disease state. As such compounds of the present invention may also be useful in the treatment of benign prostatic hypertrophy and prostatic carcinoma, the treatment of psoriasis, and as abortifacients. For their end-use application, the potency and other biochemical parameters of the enzyme inhibiting characteristics of compounds of the present invention are readily ascertained by standard biochemical techniques well known in the art. Actual dose ranges for this application will depend upon the nature and severity of the disease state of the patient or animal to be treated as determined by the attending diagnostician. It is to be expected that a general dose range will be about 0.01 to 10 mg per kg per day for an effective therapeutic effect.

Additional uses for compounds of the present invention include analysis of commercial reagent enzymes for active site concentration. For example, chymotrypsin is supplied as a standard reagent for use in clinical quantitation of chymotrypsin activity in pancreatic juices and feces. Such assays are diagnostic for gastrointestinal and pancreatic disorders. Pancreatic elastase is also supplied commercially as a reagent for quantitation of $\alpha_1$-antitrypsin in plasma. Plasma $\alpha_1$-antitrypsin increases in concentration during the course of several inflammatory diseases, and $\alpha_1$-antitrypsin deficiencies are associated with increased incidence of lung disease. Compounds of the present invention can be used to enhance the accuracy and reproducibility of these assays by titrametric standardization of the commercial elastase supplied as a reagent. See, U.S. Pat. No. 4,499,082.

Protease activity in certain protein extracts during purification of particular proteins is a recurring problem which can complicate and compromise the results of protein isolation procedures. Certain proteases present in such extracts can be inhibited during purification steps by compounds of the present invention, which bind tightly to various proteolytic enzymes.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

For compositions of the present invention suitable for administration to a human, the term "excipient" is meant to include, but not be limited by, those excipients described in the *Handbook of Pharmaceutical Excipients*, American Pharmaceutical Association, $2^{nd}$ Ed. (1994), which is herein incorporated by reference in its entirety. Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions and cyclodextrin inclusion complexes. Especially preferred alkaline salts are ammonium salts prepared, for example, with Tris, choline hydroxide, Bis-Tris propane, N-methylglucamine, or arginine. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

Compounds of Formula I can be labeled with radioactive iodine by using an exchange reaction. Exchange of hot iodine for cold iodine is well known in the art. Alternatively, a radio iodine labeled compound can be prepared from the corresponding bromo compound via a tributylstannyl intermediate. See, U.S. Pat. No. 5,122,361, herein incorporated by reference.

The present invention also includes compositions which are useful for in vivo imaging of thrombi in a mammal, wherein the compositions are comprised of a compound of Formula I complexed with a radioactive atom.

For the compounds of Formula I, suitable radioactive atoms include Co-57, Cu-67, Ga-67, Ga-68, Ru-97, Tc-99m, In-111, In-113m, Hg-197, Au-198, and Pb-203. Some radioactive atoms have superior properties for use in radiochemical imaging techniques. In particular, technetium-99m (Tc-99m) is an ideal radioactive atom for imaging because of its nuclear properties. Rhenium-186 and -188 also have gamma emission which allows it to be imaged. Preferred compositions contain the radioactive atom, Tc-99m.

The compounds of Formula I can be labeled by any of the many techniques known in the art to provide a composition of the present invention. For example, these compounds can be labeled through a chelating agent such as diethylenetriaminepentaacetic acid (DTPA) or metallothionein, both of which can be covalently attached to the compound of Formula I.

In general, the compositions of the present invention containing technetium-99m are prepared by forming an aqueous mixture of technetium-99m and a reducing agent and a water-soluble ligand, and then contacting the mixture with a compound of the present invention represented by Formula I. For example, the imaging compounds of this invention are made by reacting technetium-99m (in an oxidized state) with the compounds of the present invention having a chelating means in the presence of a reducing agent to form a stable complex between technetium-99m in a reduced state (IV or V valence state).

One embodiment of the composition of the present invention is prepared by labeling a compound of Formula I having a DTPA chelating means with technetium-99m. This may be accomplished by combining a predetermined amount (as 5 $\mu$g to 0.5 mg) of compound of the present invention with an aqueous solution containing citrate buffer and stannous reducing agent, then adding freshly eluted sodium pertechnetate containing a predetermined level of radioactivity (as 15 mCi). After allowing an incubation of the mixture at room temperature, the reaction mixture is loaded into a shielded syringe through a sterile filter (0.2–0.22 micron), then is dispensed into 0.9% saline for injection, if desired.

Another embodiment of the compositions of the present invention is prepared by labeling a compound of Formula I having a metallothionein chelating means with technetium-99m. This may be accomplished by combining aqueous sodium pertechnetate-99m with aqueous stannous glucoheptonate to form a soluble complex of technetium-99m (in reduced state) with two glucoheptonate molecules, then combining this solution with a compound of the Formula I having a metallothionein attached thereto. After incubating the mixture for a period of time and under conditions which allow for an exchange of the technetium-99m from the glucoheptonate complex to the metallothionein of the compound of Formula I, the technetium-labeled composition of the present invention is formed.

Reducing agents for use in the method are physiologically acceptable for reducing technetium-99m from its oxidized state to the IV or V valence state or for reducing rhenium from its oxidized state. Reducing agents which can be used are stannous chloride, stannous fluoride, stannous glucoheptonate, stannous tartarate, and sodium dithionite. The preferred agents are stannous reducing agents, especially stannous chloride or stannous glucoheptonate. The amount of reducing agent is that amount necessary to reduce the technetium-99m to provide for the binding to the chelating means of a compound of Formula I in this radioisotope's reduced state. For example, stannous chloride ($SnCl_2$) is the reducing agent and can be used in range from 1–1,000 $\mu$g/mL.

Citric acid complexes with technetium-99m quickly to form a stable technetium-99m-citrate complex. Upon contact with a compound of Formula I, substantially quantitative transfer of technetium-99m from its citrate complex to the chelating means of the compound of Formula I is achieved rapidly and under mild conditions. The amount of citric acid (as sodium citrate) can range from about 0.5 mg/ml up to the amount maximally soluble in the medium. Preferred amounts of citric acid range from 15 to 30 $\mu$g/ml.

The amount of compound of Formula I having a chelating means can range from 0.001 to about 3 mg/mL, preferably about 0.017 to about 0.15 mg/mL. Finally, technetium-99m in the form of pertechnetate can be used in amounts of preferably about 1–50 mCi. The amount of mCi per mg of compound of the present invention is preferably about 30–150.

The reaction between the compound of Formula I and the metal ion-transfer ligand complex is preferably carried out in a aqueous solution at a pH at which the compound of Formula I is stable. By "stable", it is meant that the compound remains soluble and retains its inhibitory activity against α-thrombin. Normally, the pH for the reaction will be from about 5 to 9, the preferred pH being above 6–8. The technetium-99m-citrate complex and a compound of Formula I are incubated, preferably at a temperature from about 20° C. to about 60° C., most preferably from about 20° C. to about 37° C., for a sufficient amount of time to allow transfer of the metal ion from the citrate complex to the chelating means of the compound of Formula I. Generally, less than one hour is sufficient to complete the transfer reaction under these conditions.

Alternative compositions of the present invention include an In-111 labeled compound of the present invention.

The present invention also includes compositions of the compounds of the present invention which are useful for in vivo imaging of thrombi in a mammal, comprised of a compound represented by Formula I complexed to a paramagnetic atom.

Preferred paramagnetic atoms are divalent or trivalent ions of elements with an atomic number of 21 to 29, 42, 44 and 58 to 70. Suitable ions include chromium(III), manganese(II), iron(III), iron(II), cobalt(II), nickel(II), copper(II), praseodymium(III), neodymium(III), samarium (III) and ytterbium(III). Because of their very strong magnetic moments, gadolinium(III), terbium(III), dysoprosium (III), holmium(III), and erbium(III) are preferred. Especially preferred for the paramagnetic atom is gadolinium(III).

The compositions of the present invention may be prepared by combining a compound of Formula I with a paramagnetic atom. For example, the metal oxide or a metal salt (for example, nitrate, chloride or sulfate) of a suitable paramagnetic atom is dissolved or suspended in a medium comprised of water and an alcohol, such as methyl, ethyl or isopropyl alcohol. This mixture is added to a solution of an equimolar amount of the compound of Formula I in a similar aqueous medium and stirred. The reaction mixture may be heated moderately until the reaction is completed. Insoluble compositions formed may be isolated by filtering, while soluble compositions may be isolated by evaporation of the solvent. If acid groups on the chelating means are still present in the composition of the present invention, inorganic or organic bases, and even amino acids, may be added to convert the acidic complex into a neutral complex to facilitate isolation or purification of homogenous composition. Organic bases or basic amino acids may be used as neutralizing agents, as well as inorganic bases such as hydroxides, carbonates or bicarbonates of sodium, potassium or lithium.

The present invention also include diagnostic compositions which are useful for in vivo imaging of thrombi in a mammal, comprising a pharmaceutically acceptable carrier and a diagnostically effective amount of compositions derived from the compounds of Formula I.

The "diagnostically effective amount" of the composition required as a dose will depend on the route of administration, the type of mammal being treated, and the physical characteristics of the specific mammal under consideration. These factors and their relationship to determining this dose are well known to skilled practitioners in the medial diagnostic arts. Also, the diagnostically effective amount and method of administration can be tailored to achieve optimal efficacy but will depend on such factors as weight, diet, concurrent medication and other factors which those skilled in the medical arts will recognize. In any regard, the dose for imaging should be sufficient for detecting the presence of the imaging agent at the site of a thrombus in question. Typically, radiologic imaging will require that the dose provided by the pharmaceutical composition position of the present invention be about 5 to 20 $\mu$Ci, preferably about 10 $\mu$Ci. Magnetic resonance imaging will require that the dose provided be about 0.001 to 5 mmole/kg, preferably about 0.005 to 0.5 mmole/kg of a compound of Formula I complexed with paramagnetic atom. In either case, it is known in the art that the actual dose will depend on the location of the thrombus.

"Pharmaceutically acceptable carriers" for in vivo use are well known in the pharmaceutical art, and are described, for example, in *Remington's Pharmaceutical Sciences*, Mack Publishing Co. (A. R. Gennaro edit. 1985). The pharmaceutical compositions of the present invention may be formulated with a pharmaceutically acceptable carrier to provide sterile solutions or suspensions for injectable administration. In particular, injectables can be prepared in conventional forms, either as liquid solutions or suspensions, solid forms suitable for solution or suspensions in liquid prior to injection, or as emulsions, Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

The present invention also encompasses diagnostic compositions prepared for storage or administration. These would additionally contain preservatives, stabilizers and dyes. For example, sodium benzoate, sorbic acid and esters of p-hydroxybenzoic acid may be added as preservatives. Id. at 1449. In addition, antioxidants and suspending agents may be used.

The in vivo imaging methods of the present invention also offer several advantages over previous imaging techniques for the detection or monitoring of the presence, size, regression or increase of a thrombus. In particular, the present invention provides compounds, compositions and diagnostic compositions that bind tightly to the thrombin associated with a thrombus and thereby reduce "background" due to circulating radioactivity or paramagnetism arising from unbound imaging agent. Furthermore, in vivo imaging by intracoronary injection of the compounds, compositions or diagnostic compositions of the present invention, is expected to be almost instantaneous since these imaging agents would saturate the thrombin bound to the thrombus immediately.

Accordingly, the present invention also includes methods for in vivo imaging of a thrombus in a mammal, comprising the steps of: (1) administering to a mammal a diagnostically acceptable amount of a compound, composition, or diagnostic composition of the present invention and (2) detecting a thrombus in a blood vessel.

The term "in vivo imaging" as used herein relates to methods of the detection of a thrombus in a mammal, as well as the monitoring of the size, location and number of thrombi in a mammal, as well as dissolution or growth of the thrombus.

In employing the compounds, compositions or diagnostic compositions in vivo by this method, "administering" is accomplished parenterally, in either a systemic or local targeted manner. Systemic administration is accomplished by injecting the compounds, compositions by diagnostic compositions of the present invention into a convenient and accessible vein or artery. This includes but is not limited to administration by the ankecubutal vein. Local targeted administration is accomplished by injecting the compounds, compositions or diagnostic compositions of the present invention proximal in flow to a vein or artery suspected to contain thrombi distal to the injection site. This includes but is not limited to direct injection into the coronary arterial vasculature to image coronary thrombi, into the carotid artery to image thrombi in the cerebral vasculature, or into a pedal vein to image deep vein thrombosis of the leg.

Also, the manner of delivery of a composition of the present invention to the site of a thrombus is considered within the scope of the term "administering". For example, a compound represented by Formula I having a chelating means attached thereto may be injected into the mammal, followed at a later time by the radioactive atom thereby forming in vivo at the site of the thrombus the composition comprising the compound of formula complexed to radioactive atom. Alternatively, a composition comprising the compound of formula complexed to radioactive atom may be injected into the mammal.

The "diagnostically effective amount" of the compounds, compositions or diagnostic compositions used in the methods of the present invention will, as previously mentioned, depend on the route of administration, the type of mammal being treated, and the physical characteristics of the specific mammal under treatment. These factors and their relationship to determining this dose are well known to skilled practitioners in the medical diagnostic arts. In any regard, the dose for in vivo imaging should be sufficient for detecting the presence of the imaging agent at the site of a thrombus in question. Typically, radiologic imaging will require that the dose provided by the diagnostic composition of the present invention be about 5 to 20 µCi, preferably about 10 µCi. Magnetic resonance imaging will require that the dose provided by the diagnostic composition be about 0.001 to 5 mmole/kg, preferably about 0.005 to 0.5 mmole/kg of a compound of Formula I complexed with paramagnetic atom. In either case, it is known in the art that the actual dose will depend on the location of the thrombus.

The detecting of a thrombus by imaging is made possible by the presence of radioactive or paramagnetic atoms localized at such thrombus.

The radioactive atoms associated with the compositions and diagnostic compositions of the present invention are preferably imaged using a radiation detection means capable of detecting gamma radiation, such as a gamma camera or the like. Typically, radiation imaging cameras employ a conversion medium (wherein the high energy gamma ray is absorbed, displacing an electron which emits a photon upon its return to the orbital state), photoelectric detectors arranged in a spatial detection chamber (to determine the position of the emitted photons), and circuitry to analyze the photons detected in the chamber and produce an image.

The paramagnetic atoms associated with the compositions and diagnostic compositions of the present invention are detected in magnetic resonance imaging (MRI) systems. In such systems, a strong magnetic field is used to align the nuclear spin vectors of the atoms in a patient's body. The field is disturbed by the presence of paramagnetic atoms localized at a thrombus and an image of the patient is read as the nuclei return to their equilibrium alignments.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLES

Example 1

N-[2-(Amidinoaminooxy)ethyl]-2-{3-[(2,2-difluoro-2-phenylethyl)amino]-6-chloro-2-fluorophenyl}acetamide Trifluoroacetate Salt

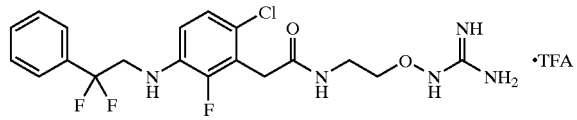

1. Ethyl 2,2-difluoro-2-phenylacetate (Middleton, W., et al. *J. Org. Chem.* 42:2883 (1980)).

A mixture of ethyl benzoylformate (12.5 g, 70.0 mmol) and (diethylamino)sulfur trifluoride (DAST, 18.5 mL, 140 mmol) was stirred for 48 hours at ambient temperature, and then poured over ice. The oil formed was taken up into dichloromethane (DCM), washed with $H_2O$, dried over $Na_2SO_4$, concentrated, and filtered through a short column of silica gel eluting with 50% DCM/hexane. The filtrate was concentrated to give the title compound (12.3 g, 88% yield) as a brown liquid. $^1$H NMR (400 MHz, CDCl$_3$) δ 7.65–7.63 (m, 2H), 7.52–7.43 (m, 3H), 4.30 (q, J=7.1 Hz, 2H), 1.30 (t, J=7.1 Hz, 3H).

2. 2,2-Difluoro-2-phenylacetic Acid

A suspension of ethyl 2,2-difluoro-2-phenylacetate (6.0 g, 30 mmol), as prepared in the preceding step, in 1 N NaOH (36 mL, 36 mmol) was stirred at ambient temperature. After 36 hours, the reaction became almost homogeneous. The mixture was acidified with 1N HCl (36 mL), and extracted with DCM twice. The extracts were combined, washed with $H_2O$, dried over $Na_2SO_4$, and concentrated to give the title compound (3.85 g, 81% yield) as a pale yellow solid, that was used without further purification.

3. 2,2-Difluoro-2-phenylacetyl Chloride

To a flask charged with 2,2-difluoro-2-phenylacetic acid (0.8 g, 5.06 mmol), as prepared in the preceding step, under argon in an ice-bath was added oxalyl chloride (5 mL), and the reaction mixture stirred for 15 min. A solution of dimethylformamide (DMF) (37 mg, 0.506 mmol) in DCM (0.5 mL) was added. After 2 hours, the ice-bath was removed, and the mixture continued to stir for 1 hour. The solvents were evaporated, DCM was added, and then evaporated in vacuo giving the title compound (0.88 g, 98% yield), that was used immediately without further purification.

4. 2-(2,3-Difluoro-6-nitrophenyl)acetic Acid
(Yokomoto, M, W., et al. 1991, EP 0 470 578 A1)

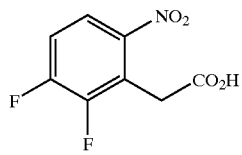

To a suspension of NaH (11.3 g, 60% oil dispersion, 282 mmol) in tetrahydrofuran (THF) (35 mL) in an ice-bath was added a solution of diethyl malonate (45.2 g, 42.9 mL, 282 mmol) in THF (70 mL) over a period of an hour so that the reaction temperature was kept below 20° C. Some white solid precipitated during the addition. To the above reaction mixture was added a solution of 1,2,3-trifluoro-4-nitrobenzene (25.0 g, 141 mmol) in THF (35 mL) over a period of 1 hour so that the reaction temperature was kept below 10° C. The ice-bath was removed and the mixture was stirred at ambient temperature for 2 hours. Acetic acid (18 mL) was added to the reaction solution, and THF was evaporated under reduced pressure. Chloroform (200 mL), $H_2O$ (250 mL), and concentrated HCl (18 mL) were added. The organic layer was separated, concentrated, mixed with 4N HCl (45 mL) and acetic acid (35 mL), and refluxed for 14 hours. The reaction mixture was allowed to cool to room temperature. The solid precipitated upon cooling was filtered off, washed with diisopropyl ether, and dissolved in MeOH (70 mL). After treating with active carbon, the solvent was evaporated, and the crystalline residue washed with isopropyl ether, and filtered off to give the title compound (17.6 g, 58% yield) as a white solid. $^1$H-NMR (400 MHz, CDCl$_3$) δ 8.05–8.01 (m, 1H), 7.47 (dd, J=17.4, 8.9 Hz, 1H), 4.10 (s, 2H).

5. 2-(2,3-Difluoro-6-nitrophenyl)ethanol
(Yokomoto, M, W., et al., EP 0 470 578 A1 (1991))

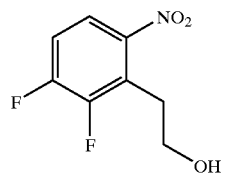

To a mixture of NaBH$_4$ (3.60 g, 95.4 mmol) in THF (12 mL) cooled below 10° C. was added a solution of 2-(2,3-difluoro-6-nitrophenyl)acetic acid (10.9 g, 50.2 mmol), as prepared in the preceding step, in THF (4 mL) over a period of 1 hour. To this mixture was added a solution of boron trifluoride diethyl etherate complex (16.5 mL, 131 mmol) in THF (24 mL) over a period of 1 hour, keeping the reaction temperature below 10° C. After the addition the reaction was continued to stir on ice for 15 minutes, and then at ambient temperature for 20 minutes. To a mixture of DCM (180 mL) and H$_2$O (140 mL) was added NaHCO$_3$ (15 g, 179 mmol). The reaction mixture was slowly added to the above NaHCO$_3$ solution and stirred overnight. The organic layer was separated, dried over Na$_2$SO$_4$, and concentrated to give the title compound (10.1 g, 99% yield) as light brown oil. $^1$H NMR (400 MHz, CDCl$_3$) δ 7.82 (dd, J=9.1, 4.4 Hz, 1H), 7.27–7.18 (m, 1H), 3.95 (t, J=6.3 Hz, 2H), 3.30–3.27 (m, 2H), 1.82 (s, 1H).

6. 2-{3-[(tert-Butyl)amino]-2-fluoro-6-nitrophenyl}ethanol (Yokomoto, M, W., et al. EP 0 470 578 A1 (1991)).

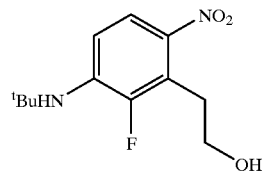

A mixture of 2-(2,3-difluoro-6-nitrophenyl)ethanol (6.00 g, 29.6 mmol), as prepared in the preceding step, tert-butylamine (18.6 mL, 1.77 mmol), DMSO (30 mL), and toluene (5 mL) was heated at reflux for 16 hours. After cooling to ambient temperature the brown solution was poured into H$_2$O (300 mL), and the deposited yellow crystals were filtered and washed with H$_2$O twice. The yellow solid was dissolved in CHCl$_3$ (70 mL), dried over Na$_2$SO$_4$, concentrated, and crystallized from hexane to give the title compound (4.70 g, 62% yield) as a yellow solid. $^1$H NMR (400 MHz, CDCl$_3$) δ 7.92 (dd, J=9.3, 1.5 Hz, 1H), 6.79 (t, J=8.7 Hz, 1H), 4.69 (br s, 1H), 3.96 (dd, J=11.4, 5.9 Hz, 2H), 3.32 (dt, J=6.5, 3.1 Hz, 2H), 1.75 (t, J=5.3 Hz, 1 H), 1.46 (s, 9H).

7. 2-(3-Amino-2-fluoro-6-nitrophenyl)ethanol
(Yokomoto, M, W., et al. EP 0 470 578 A1 (1991))

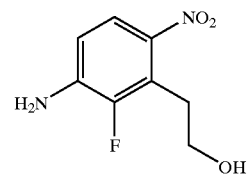

A solution of 2-{3-[(tert-butyl)amino]-2-fluoro-6-nitrophenyl}ethanol (3.9 g, 15 mmol), as prepared in the preceding step, in concentrated HCl (40 mL) was refluxed for 2 hours. After cooling to room temperature, the mixture was extracted with ethyl acetate (6×50 mL). The extracts were combined, washed with saturated NaHCO$_3$ (2 times) and brine, dried over Na$_2$SO$_4$, and concentrated to give the crude product as a solid. The solid was triturated in hexane, filtered, and dried in high vacuum to produce the title compound (2.8 g, 93% yield) as a yellow solid. $^1$H-NMR (400 MHz, CD$_3$OD) δ 7.80 (dd, J=9.1, 1.5 Hz, 1H), 6.70 (t, J=9.0 Hz, 1H), 3.77 (t, J=7.1 Hz, 2H), 3.26 (dt, J=7.3, 2.8 Hz, 2).

8. 2-(3-Amino-2-fluoro-6-nitrophenyl)ethyl Acetate

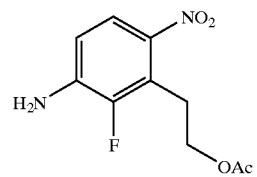

To a solution of DIEA (1.80 mL, 10.6 mmol) and 2-(3-amino-2-fluoro-6-nitrophenyl)ethanol (0.88 g, 4.40 mmol), as prepared in the preceding step, in THF (10 mL) in an ice-bath was added a solution of acetyl chloride (319 μL, 4.49 mmol) in THF (5 mL). After stirring for 1.5 hour, the ice-bath was removed and the mixture was continued to stir at ambient temperature overnight. Additional acetyl chloride (63 μL, 0.88 mmol) was added, and the mixture was stirred for another 16 hours. The solvents were removed, and the mixture was partitioned between DCM and H$_2$O. The organic layer was separated, and the aqueous layer was back-extracted with DCM. The organic layers were combined, washed with H$_2$O (twice), dried over Na$_2$SO$_4$, concentrated, and flash chromatographed on silica gel eluting with EtOAc/DCM (0, 1, 2, and 5%) to give the title compound (0.73 g, 69% yield) as a yellow solid. $^1$H-NMR (400 MHz, CDCl$_3$) δ 7.85 (dd, J=9.0, 1.5 Hz, 1H), 6.68 (t, J=8.9 Hz, 1H), 4.38–4.35 (m, 4H), 3.38 (dt, J=6.6, 2.8 Hz, 2H), 2.03 (s, 3H).

9. 2-[3-(2,2-Difluoro-2-phenylacetylamino)-2-fluoro-6-nitrophenyl]ethyl Acetate

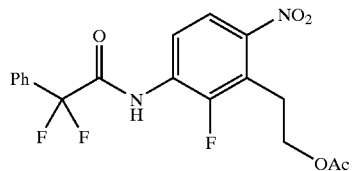

To a solution of DIEA (1.49 mL, 8.55 mmol) and 2-(3-amino-2-fluoro-6-nitrophenyl)ethyl acetate (690 mg, 2.85 mmol), as prepared in the preceding step, in DCM (6 mL) was added a solution of 2,2-difluoro-2-phenylacetyl chloride (0.99 g, 5.20 mmol), as prepared according to the procedure of step 3 of Example 1, in DCM (3 mL). After stirring for 24 hours, the mixture was concentrated, and partitioned between DCM and H$_2$O. The organic layer was separated, and the aqueous layer extracted with DCM. The organic layers were combined, washed with H$_2$O and brine, dried over Na$_2$SO$_4$, concentrated, and flash chromatographed on silica gel eluting with EtOAc/DCM (0, 2.5, and 5%) to give the title compound (1.04 g, 92% yield) as an orange oil. $^1$H-NMR (400 MHz, CDCl$_3$) δ 8.49–8.43 (m, 2H), 7.87 (d, J=9.2 Hz, 1H), 6.68 (d, J=7.1 Hz, 2H), 7.55–7.49 (m, 3H), 4.35 (t, J=6.4 Hz, 2H), 3.37 (dt, J=6.3, 2.3 Hz, 2H), 2.01 (s, 3H).

10. 2-[2-Amino-5-(2,2-fluoro-2-phenylacetylamino)-6-fluorophenyl]ethyl Acetate

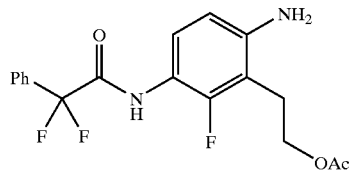

A mixture of 2-[3-(2,2-difluoro-2-phenylacetylamino)-2-fluoro-6-nitrophenyl]ethyl acetate (0.84 g, 2.12 mmol), as prepared in the preceding step, and palladium catalyst (226 mg, 10% on activated carbon, 0.212 mmol) in ethanol (17 mL) was hydrogenated under a hydrogen balloon for 3.5 hours. The mixture was filtered through Celite (diatomaceous earth) and washed with MeOH. The filtrate and washings were combined, concentrated, and flash chromatographed on silica gel eluting with EtOAc/DCM (5, 10, and 20%) to give the title compound (0.713 g, 92% yield) as a white solid. $^1$H-NMR (400 MHz, CDCl$_3$) δ 8.10 (bs, 1H), 7.81 (t, J=8.7 Hz, 1H), 7.68–7.66 (m, 2H), 7.52–7.44 (m, 3H), 6.45 (dd, J=8.8, 1.2 Hz, 1H), 4.18 (t, J=7.4 Hz, 2H), 4.07 (bs, 2H), 2.90 (dt, J=7.4, 1.9 Hz, 2H), 2.07 (s, 3H). Mass spectrum (LCMS, ESI) calc'd for C$_{18}$H$_{18}$F$_3$N$_2$O$_3$ (M+H): 367.1. Found: 367.1.

11. N-[4-Amino-2-fluoro-3-(2-hydroxyethyl)phenyl]-2,2-difluoro-2-phenylacetamide

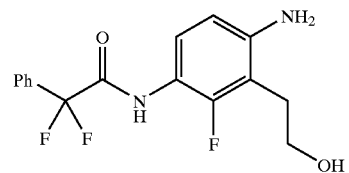

To a solution of 2-[2-amino-5-(2,2-difluoro-2-phenylacetylamino)-6-fluorophenyl] ethyl acetate (0.67 g, 1.84 mmol), as prepared in the preceding step, in MeOH (19 mL) was added dropwise a solution of K$_2$CO$_3$ (280 mg, 2.03 mmol) in H$_2$O (4.8 mL). The mixture was stirred for 45 minutes, and then neutralized with 1N HCl. The MeOH was evaporated, and the mixture was extracted with EtOAc twice. The extracts were combined, washed with H$_2$O, dried over Na$_2$SO$_4$, and concentrated to give the title compound (0.55 g, 92% yield) as a pale yellow solid. $^1$H-NMR (400 MHz, CD$_3$OD) δ 7.70–7.68 (m, 2H), 7.54–7.48 (m, 3H), 7.01 (t, J=8.5 Hz, 1H), 6.53 (dd, J=8.6, 1.3 Hz, 1H), 3.70 (t, J=6.7 Hz, 2H), 2.80 (dt, J=6.7, 2.0 Hz, 2H). Mass spectrum (LCMS, ESI) calc'd for C$_{16}$H$_{16}$F$_3$N$_2$O$_2$ (M+H): 325.1. Found: 325.3.

12. N-[4-Chloro-2-fluoro-3-(2-hydroxyethyl)phenyl]-2,2-difluoro-2-phenylacetamide (Yokomoto, M, W., et al. 1991, EP 0470 578 A1).

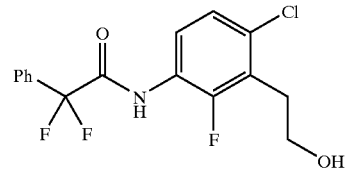

A suspension of N-[4-amino-2-fluoro-3-(2-hydroxyethyl)phenyl]-2,2-difluoro-2-phenylacetamide (1.63 g, 5.00 mmol), as prepared according to the procedure of the preceding step, in 6N HCl (9 mL) was cooled in an ice-bath, and then a solution of NaNO$_2$ (434 mg, 6.30 mmol) in H$_2$O (2.4 mL) was added over a period of 5 minutes. After 30 minutes, acetic acid (2.9 mL) and concentrated HCl (2.9 mL) were added and the reaction mixture stirred for 1 hour. To this mixture was added a solution of CuCl (848 mg, 8.55 mmol) in concentrated HCl (5 mL) over a period of 20 minutes. After stirring in an ice-bath for 3 hours, the reaction mixture was extracted with EtOAc (200 mL×3). The extracts were combined, washed with H$_2$O (2 times) and brine, dried over Na$_2$SO$_4$, concentrated, and flash chromatographed on silica gel eluting with EtOAc/DCM (0, 2.5, and 5%) to deliver the title compound (0.845 g, 48% yield) as a pale orange oil. $^1$H-NMR (400 MHz, CDCl$_3$)δ 8.31 (s, 1H), 8.14 (t, J=8.6 Hz, 1H), 7.68–7.66 (m, 2H), 7.54–7.46 (m, 3H), 7.19 (dd, J=8.9, 1.7 Hz, 1H), 3.86 (dd, J=12.6, 6.5 Hz., 2H), 3.09 (dt, J=6.7, 2.3 Hz, 2H), 1.58 (t, J=5.7 Hz, 1H). Mass

13. 2-{3-[(2,2-Difluoro-2-phenylethyl)amino]-6-chloro-2-fluorophenyl}ethanol

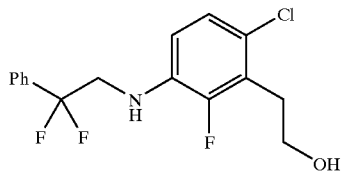

To a solution N-[4-chloro-2-fluor-3-(2-hydroxyethyl) phenyl]-2,2-difluoro-2-phenylacetamide (1.05 g, 3.06 mmol), as prepared according to the procedure in the preceding step, in THF (12 mL) at 0° C. under argon was added a solution of borane-THF complex in THF (12.3 mL, 12.3 mmol, 1.0 M) over a period of 10 minutes, and the reaction mixture continued to stir until the ice-bath expired. The reaction mixture was heated at reflux for 20 hours, and allowed to cool to room temperature. A solution of $K_2CO_3$ (1.7 g, 12 mmol) in $H_2O$ (12 mL) was added, the THF was removed in vacuo, and the mixture was extracted with DCM (3 times). The extracts were combined, washed with brine, dried over $Na_2SO_4$, concentrated, and flash chromatographed on silica gel eluting with EtOAC/DCM (0 and 2.5%) to give the title compound (815 mg, 81% yield) as a colorless oil. $^1$H-NMR (400 MHz, $CDCl_3$) δ 7.52–7.43 (m, 5H), 6.97 (dd, J=8.8, 1.7 Hz, 1H), 6.51 (t, J=8.9 Hz, 1H), 4.17 (bs, 1H), 3.83 (t, J=6.9 Hz, 2H), 3.74 (dt, J=13.4, 6.6 Hz, 2H), 3.04 (dt, J=6.9, 2.4 Hz, 2H), 1.43 (s, 1H). Mass spectrum (LCMS, ESI) calc'd for $C_{16}H_{16}ClF_3NO$ (M+H): 330.1. Found: 330.3.

14. 2-{3-[(2,2-Difluoro-2-phenylethyl)amino]-6-chloro-2-fluorophenyl}ethanal

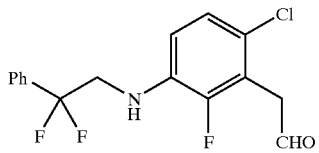

To a solution of DMSO (1.03 mL, 14.5 mmol), DIEA (1.99 mL, 11.4 mmol), and 2-{3-[(2,2-difluoro-2-phenylethyl)amino]-6-chloro-2-fluorophenyl}ethanol (1.45 g, 4.4 mmol), as prepared according to the procedure in the preceding step, in DCM (140 mL) in an ice-bath was added sulfur trioxide pyridine complex (1.82 g, 11.4 mmol) and stirred at the same temperature for 3.5 hours. The mixture was diluted with DCM (300 mL), washed with 10% citric acid (3 times), $H_2O$, and brine, dried over $Na_2SO_4$, and concentrated to give the title compound (1.43 g, 99% yield) as an orange oil, that was used without further purification.

15. 2-{3-[(2,2-Difluoro-2-phenylethyl)amino]-6-chloro-2-fluorophenyl}acetic Acid (Dalcanale, E., et al. J. Org. Chem., 51:567 (1986)).

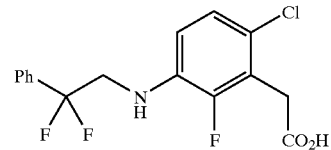

A solution of sodium chlorite (692 mg, 6.11 mmol) in $H_2O$ (6.1 mL) was added over a period of 30 minutes to a stirred mixture of 2{-3-[(2,2-difluoro-2-phenylethyl) amino]-6-chloro-2-fluorophenyl}ethanal (1.43 g, 4.37 mmol), as prepared in the preceding step, in DMSO (4.5 mL) and of $NaH_2PO_4$ (141 mg, 1.18 mmol) in $H_2O$ (1.7 mL). After the addition, the mixture was stirred at ambient temperature overnight, acidified with 10 M HCl to pH 1, and extracted with DCM (3 times). The extracts were combined, washed with $H_2O$ and brine, dried over $Na_2SO_4$, and concentrated in vacuo. The resulting residue was flash chromatographed on silica gel eluting with MeOH/DCM (0, 2, and 4%) to give the title compound (0.77 g, 51% yield) as a pale brown solid. $^1$H-NMR (400 MHz, $CD_3OD$) δ 7.53–7.51 (m, 2H), 7.44–7.41 (m, 3H), 6.93 (dd, J=8.9, 1.8 Hz, 1H), 6.62 (t, J=9.1 Hz, 1H), 3.80 (t, J=13.7 Hz, 2H), 3.74 (d, J=2.2 Hz, 2H). Mass spectrum (LCMS, ESI) calc'd for $C_{16}H_{14}ClF_3NO_2$ (M+H): 344.1. Found: 344.4.

16. tert-Butyl 2-aza-3-{[2-(2-{3-[(2,2-difluoro-2-phenylethyl)amino]-6-chloro-2-fluorophenyl}acetylamino)ethoxy]amino}-3-[(tert-butoxy) carbonylamino]prop-2-enate

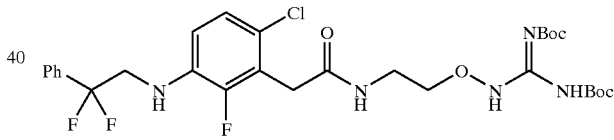

To a solution of 2-{3-[(2,2-difluoro-2-phenylethyl) amino]-6-chloro-2-fluorophenyl}acetic acid (28 mg, 82 μmol), as prepared in the preceding step, in DMF (0.3 mL) in an ice-bath was added BOP (58 mg, 130 μmol), HCl salt of [N,N'-di(tert-butoxycarbonyl)]-2-aminoethoxyguanidine (36 mg, 102 μmol) (Tianbao Lu, et al., WO 99/26926 (1999)), and a solution of DIEA (42 mg, 33 μmol) in DMF (0.1 mL). After the ice-bath expired, the reaction mixture continued to stir at ambient temperature overnight. The solvents were evaporated, and the resulting residue was partitioned between saturated $NaHCO_3$ and DCM. The aqueous phase was extracted with DCM, and the organic layers were combined, washed with 10% $KHSO_4$, $H_2O$, and brine, dried over $Na_2SO_4$, concentrated, and flash chromatographed on silica gel eluting with MeOH/DCM (1%) to give the title compound (44 mg, 83% yield) as a colorless oil. $^1$H-NMR (400 MHz, $CDCl_3$) δ 7.54–7.50 (m, 2H), 7.45–7.42 (m, 3H), 6.93 (dd, J=8.8, 1.7 Hz, 1H), 6.63 (t, J=9.0 Hz, 1H), 4.03 (t, J=4.8 Hz, 2H), 3.81 (t, J=13.7 Hz, 2H), 3.71 (d, J=1.9 Hz, 2H), 3.47 (t, J=5.1 Hz, 2H), 1.50 (s, 9H), 1.48 (s, 9H). Mass spectrum (LCMS, ESI) calc'd for $C_{29}H_{38}ClF_3N_5O_6$ (M+H): 644.2. Found: 644.1.

17. N-[2-(Amidinoaminooxy)ethyl]-2-{3-[(2,2-difluoro-2-phenylethyl)amino]-6-chloro-2-fluorophenyl}acetamide Trifluoroacetate Salt

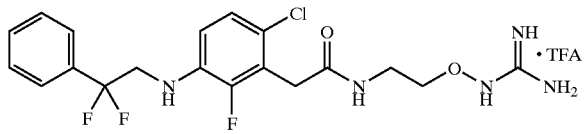

A solution of tert-butyl 2-aza-3-{[2-(2-{3-[(2,2-difluoro-2-phenylethyl)amino]-6-chloro-2-fluorophenyl}acetyl-amino)ethoxy]amino}-3-[(tert-butoxy) carbonylamino] prop-2-enoate (44 mg, 68 µmol), as prepared in the preceding step, in TFA/DCM (2 mL, 2/3) was stirred at room temperature for 4 hours. The solvents were evaporated, and the resulting residue was flash chromatographed on silica gel eluting with 0.05% TFA in MeOH/DCM (5 and 10%) to deliver the title compound (37 mg, 98% yield) as a white solid. $^1$H-NMR (400 MHz, CD$_3$OD) δ 7.67–7.52 (m, 2H), 7.47–7.42 (m, 3H), 6.96 (dd, J=8.9, 1.7 Hz, 1H), 6.66 (t, J=9.1 Hz, 1H), 3.93 (t, J=5.4 Hz, 2H), 3.82 (t, J=13.8 Hz, 2H), 3.71 (d, J=2.0 Hz, 2H), 3.50 (t, J=5.4 Hz, 2H). Mass spectrum (LCMS, ESI) calc'd for C$_{19}$H$_{22}$ClF$_3$N$_5$O$_2$ (M+H): 444.1. Found: 444.2.

Example 2

N-[6-Amino-2-methyl(3-pyridyl))methyl]-2-{3-[(2,2-difluoro-2-phenylethyl)amino]-6-chloro-2-fluorophenyl}acetamide Hydrochloride Salt

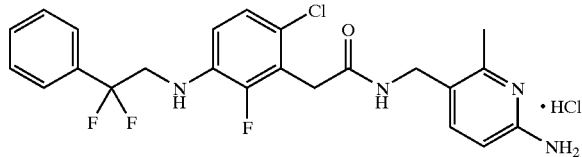

1. 2-{3-[(2,2-Difluoro-2-phenylethyl)amino]-6-chloro-2-fluorophenyl}-N-({6-[(tert-butoxy) carbonylamino]-2-methyl(3-pyridyl)}methyl) acetamide

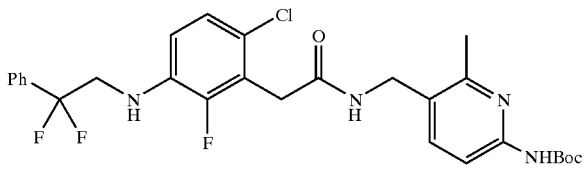

To a solution of 2-{3-[(2,2-difluoro-2-phenylethyl) amino]-6-chloro-2-fluorophenyl}acetic acid (516 mg, 1.5 mmol), as prepared in step 15 of Example 1, in DMF (8.0 mL) was added N-[5-(aminomethyl)-6-methyl (2-pyridyl)] (tert-butoxy) carboxamide (498 mg, 2.1 mmol) (Sanderson, P. E., et al., WO 97/01338 (1997)), BOP (1.06 g, 2.4 mmol), and DIEA (0.78 mL, 4.5 mmol). After stirring for 18 hours, additional amine (107 mg, 450 µmol) was added, and the mixture continued to stir for 18 hours. The solvents were evaporated, and the reaction mixture was partitioned between DCM and saturated NaHCO$_3$. The organic layer was separated, and the aqueous layer extracted with DCM. The organic layers were combined, washed with 10% KHSO$_4$ (2 times), H$_2$O, and brine, dried over Na$_2$SO$_4$, concentrated, and flash chromatographed on silica gel eluting with MeOH/DCM (0, 1.5, and 2.5%) to give the title compound (770 mg, 91% yield) as a pale brown foam. $^1$H-NMR (400 MHz, CDCl$_3$)δ 7.66 (d, J=8.4 Hz, 1H), 7.51–7.41 (m, 6H), 7.23 (bs, 1H), 7.01 (dd, J=8.8, 1.5 Hz, 1H), 6.57 (t, J=9.0 Hz, 1H), 5.64 (br s, 1H), 4.37 (d, J=5.6 Hz, 2H), 4.26–4.22 (m, 1H), 3.79–3.70 (m, 4H), 2.35 (s, 3H), 1.50 (s, 9H). Mass spectrum (LCMS, ESI) calc'd for C$_{28}$H$_{31}$ClF$_3$N$_4$O$_3$ (M+H): 563.2. Found: 562.9.

2. N-[(6-Amino-2-methyl(3-pyridyl))methyl]-2-{3-[(2,2-difluoro-2-phenylethyl)amino]-6-chloro-2-fluorophenyl}acetamide Hydrochloride Salt

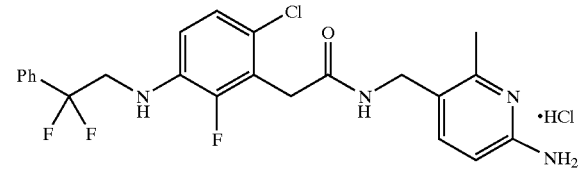

To a flask charged with 2-{3-[(2,2-difluoro-2-phenylethyl)amino]-6-chloro-2-fluorophenyl}-N-({6-[(tert-butoxy)carbonylamino]-2-methyl(3-pyridyl)}methyl) acetamide (770 mg, 1.37 mmol), as prepared in the preceding step, was added a solution of HCl in 1,4-dioxane (5 mL, 20 mmol, 4.0 M). After stirring at ambient temperature for 1.5 hours, some solid precipitated. A solution of MeOH (1 mL) in DCM (3 mL) was added to dissolve the solid, and the mixture was stirred for additional 4 hours. The solvents were removed, and the resulting residue was washed with DCM (5 mL×2), ether (8 mL×2), and dried in high vacuum to give the title compound (620 mg, 91% yield) as a pale brown solid. $^1$H-NMR (400 MHz, CD$_3$OD) δ 7.81 (d, J=9.1 Hz, 1H), 7.54–7.51 (m, 2H), 7.45–7.42 (m, 3H), 6.94 (dd, J=8.9, 1.6 Hz, 1H), 6.80 (d, J=9.1 Hz, 1H), 6.65 (t, J=9.1 Hz, 1H), 4.25 (s, 2H), 3.81 (t, J=13.8 Hz, 2H), 3.70 (d, J=1.8 Hz, 2H), 2.50 (s, 3H). Mass spectrum (LCMS, ESI) calcd for C$_{23}$H$_{23}$ClF$_3$N$_4$O (M+H): 463.1. Found: 463.7.

Example 3

N-[(6-Amino-2,4-dimethyl(3-pyridyl))methyl]-2-{3-[(2,2-difluoro-2-phenylethyl)amino]-6-chloro-2-fluorophenyl}acetamide Hydrochloride Salt

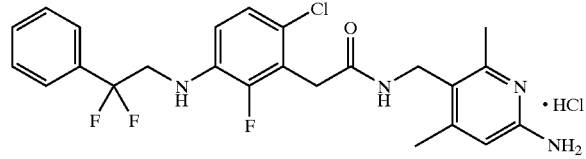

1. 2-{3-[(2,2-Difluoro-2-phenylethyl)amino]-6-chloro-2-fluorophenyl}-N-({6-[(tert-butoxy)carbonylamino]-2,4-dimethyl(3-pyridyl)}methyl)acetamide

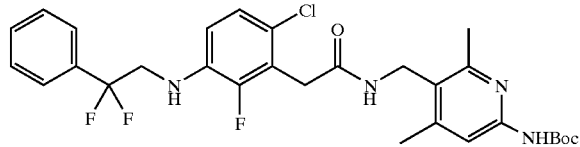

To a solution of 2-{3-[(2,2-difluoro-2-phenylethyl)amino]-6-chloro-2-fluorophenyl}acetic acid (25 mg, 73 μmol), as prepared in step 15 of Example 1, in DMF (0.25 mL) was added BOP (52 mg, 116 μmol), a solution of DIEA (38 mg, 295 mol) in DMF (0.1 mL), and N-[5-(aminomethyl)-4,6-dimethyl(2-pyridyl)](tert-butoxy)carboxamide (23 mg, 91 μmol) (Sanderson, P. E., et al. WO 97/01338 (1997)). After stirring at ambient temperature for 2 days, additional amine (7 mg, 28 μmol) BOP (16 mg, 36 μmol), and DIEA (9 mg, 70 μmol) were added, and the mixture was stirred for another 16 hours. The solvents were evaporated, and the resulting residue was partitioned between saturated NaHCO$_3$ and DCM. The organic layer was separated, and the aqueous layer was extracted with DCM. The organic layers were combined, washed with 10% citric acid, H$_2$O, and brine, dried over Na$_2$SO$_4$, concentrated, and flash chromatographed on silica gel eluting with MeOH/DCM (0, 1, 2%) to produce the title compound (18.5 mg, 44% yield) as a pale brown solid. $^1$H-NMR (400 MHz, CDCl$_3$) δ 7.58 (s, 1H), 7.50–7.41 (m, 5H), 7.24 (s, 1H), 6.98 (dd, J=8.8, 1.1 Hz, 1H), 6.55 (t, J=9.0 Hz, 1H), 5.33 (bs, 1H), 4.40 (d, J=4.7 Hz, 2H), 4.24–4.20 (m, 1H), 3.78–3.70 (m, 4H), 2.39 (s, 3H), 2.28 (s, 3H), 1.50 (s, 9H). Mass spectrum (LCMS, ESI) calcd for C$_{29}$H$_{33}$ClF$_3$N$_4$O$_3$ (M+H): 577.0. Found: 577.1.

2. N-[(6-Amino-2,4-dimethyl(3-pyridyl))methyl]-2-{3-[(2,2-difluoro-2-phenylethyl)amino]-6-chloro-2-fluorophenyl}acetamide Hydrochloride Salt

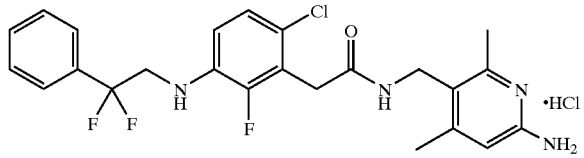

A solution of HCl in 1,4-dioxane (4.0 M, 0.5 mL, 2 mmol) was added to 2-{3-[(2,2-difluoro-2-phenylethyl)amino]-6-chloro-2-fluorophenyl}-N-({6-[(tert-butoxy)carbonylamino]-2,4-dimethyl(3-pyridyl)}methyl) acetamide (18.5 mg, 32 μmol), as prepared in the preceding step. After stirring at ambient temperature for 3 hours, solid precipitated. A solution of MeOH (0.1 mL) in DCM (1 mL) was added to dissolve the solid. After stirring for another 2 hours the reaction was concentrated to give a brown solid, that was washed with ether and DCM and dried in vacuo to produce the title compound (12.6 mg, 77% yield) as a pale brown solid. $^1$H-NMR (400 MHz, CD$_3$OD) δ 8.40 (bs, 1H), 7.53–7.51 (m, 2H), 7.47–7.40 (m, 3H), 6.93 (dd, J=8.8, 1.3 Hz, 1H), 6.68 (s, 1H), 6.64 (t, J=9.1 Hz, 1H), 4.31 (d, J=4.6 Hz, 2H), 3.81 (t, J=13.8 Hz, 2H), 3.67 (d, J=1.2 Hz, 2H), 2.54 (s, 3H), 2.42 (s, 3H). Mass spectrum (LCMS, ESI) calc'd for C$_{24}$H$_{25}$ClF$_3$N$_4$O (M+H): 477.2. Found: 477.5.

Example 4

N-[2-(Amidinoaminooxy)ethyl]-2-(3-{[2,2-difluoro-2-(4-fluoronaphthyl)ethyl]amino}-6-chloro-2-fluorophenyl)acetamide Trifluoroacetate Salt

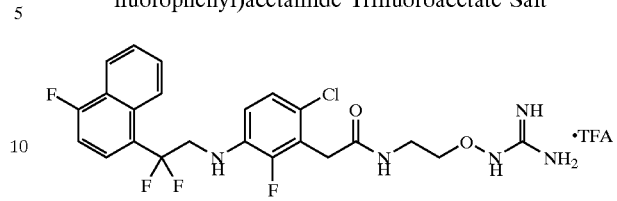

1. Ethyl 2-(4-fluoronaphthyl)-2-oxoacetate

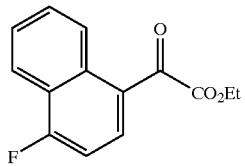

A solution of n-butyllithium (2.5 M in THF, 20 mL, 50 mmol) was cooled to −78° C., and a solution of 1-bromo-4-fluoronaphthalene (11.25 g, 50 mmol) in THF (40 mL) was added slowly and the mixture was stirred for 1 hour. The reaction mixture was warmed to −20° C., then added to a solution of diethyl oxalate (29.2 g, 200 mmol) in THF (40 mL) at −78° C. After slowly warming-up to room temperature, EtOAc (100 mL), 10% HCl (50 mL) and water (50 mL) were added and the phases were separated. The aqueous layer was extracted with EtOAc (2×100 mL), and the organic layers were combined, washed with brine (50 mL), and dried over Na$_2$SO$_4$. After evaporating the solvent and the excess diethyl oxalate under high vacuum, the residue was purified by flash column chromatography (1:1 DCM:hexane) to give the title compound (9.4 g, 76% yield) as a white solid. $^1$H—NMR (400 MHz, CDCl$_3$) δ (9.13 (d, J=8.6 Hz, 1H), 8.20 (d, J=8.4 Hz, 1H), 8.01 (dd, J=8.2, 5.4 Hz, 1H), 7.76 (t, J=7.2 Hz, 1H), 7.67 (t, J=8.1 Hz, 1H), 7.21 (t, J=8.5 Hz, 1H), 4.49 (q, J=7.1 Hz, 2H), 1.45 (t, J=7.1 Hz, 3H).

2. Ethyl 2,2-difluoro-2-(4-fluoronaphthyl)acetate

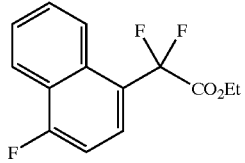

To a solution of ethyl 2-(4-fluoronaphthyl)-2-oxoacetate (9.4 g, 38.2 mmol), as prepared in the preceding step, in DCM (60 mL) was added DAST (16.1 g, 100 mmol). The mixture was stirred at room temperature overnight, poured into ice slowly, and extracted with DCM (3×50 mL). The organic layers were combined, washed with brine, and dried over Na$_2$SO$_4$. After evaporating the solvent, the residue was purified by flash column chromatography (1:1 DCM:hexane) to give the title compound (9.7 g, 95% yield) as a light brown oil. $^1$H-NMR (400 MHz, CDCl$_3$) δ 8.20 (m, 2H), 7.82 (dd, J=8.2, 5.3 Hz, 1H), 7.63 (m, 2H), 7.20 (t, J=8.4 Hz, 1H), 4.28 (q, J=7.1 Hz, 2H), 1.24 (t, J=7.1 Hz, 3H).

3. 2,2-Difluoro-2-(4-fluoronaphthyl)acetic Acid

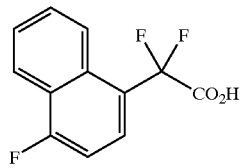

To a solution of ethyl 2,2-difluoro-2-(4-fluoronaphthyl)acetate (9.6 g, 35.8 mmol), as prepared in the preceding step, in methanol (20 mL) and THF (20 mL) was added a solution of NaOH (2.0 g, 50 mmol) in water (40 mL). The reaction mixture was stirred at room temperature for 2 hours. After evaporating the methanol and THF in vacuo, the aqueous phase was acidified to pH 2 using 10% HCl, and extracted with DCM (3×50 mL). The extracts were combined, washed with brine, dried over $Na_2SO_4$, and concentrated to give the title compound (8.1 g, 94% yield) as an off white solid. $^1$H-NMR (400 MHz, $CDCl_3$) δ 9.68 (br s, 1H), 8.18 (m, 2H), 7.83 (dd, J=8.1, 5.3 Hz, 1H), 7.62 (m, 2H), 7.19 (t, J=8.3 Hz, 1H).

4. 2-{3-[2,2-Difluoro-2-(4-fluoronaphthyl)acetylamino]-2-fluoro-6-nitrophenyl}ethyl Acetate

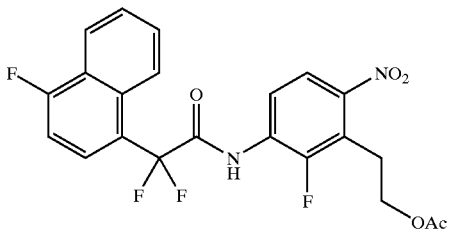

To a solution of DIEA (7.8 mL) and 2-(3-amino-2-fluoro-6-nitrophenyl)ethyl acetate (4.6 g, 19 mmol), prepared as in step 8 of Example 1, in DCM (60 mL) was added 2,2-difluoro-2-(4-fluoronaphthyl)acetyl chloride (prepared by refluxing 2,2-difluoro-2-(4-fluoronaphthyl)acetic acid, as prepared in the preceding step, with oxalyl chloride) (7.8 g, 30 mmol) in DCM (40 mL). The mixture was stirred at room temperature for 1 hour. Additional DCM (100 mL) was added, and the resulting mixture was washed with 10% citric acid (3×40 mL) and brine, and dried over $Na_2SO_4$. After evaporating the solvent, the residue was purified by flash column chromatography eluting with DCM to give the title compound (5.3 g, 61%) as a yellow oil. $^1$H-NMR (400 MHz, $CDCl_3$) δ 8.45 (m, 2H), 8.21 (d, J=7.0 Hz, 2H), 7.87 (s, 1H), 7.85 (t, J=4.1 Hz, 1H), 7.66 (m, 2H), 7.22 (t, J=8.3 Hz, 1H), 4.34 (t, J=6.4 Hz, 2H), 3.36 (t, J=6.4 Hz, 2H), 2.00 (s, 3H).

5. 2-{2-Amino-5-[2,2-difluoro-2-(4-fluoronaphthyl)acetylamino]-6-fluorophenyl}ethyl Acetate

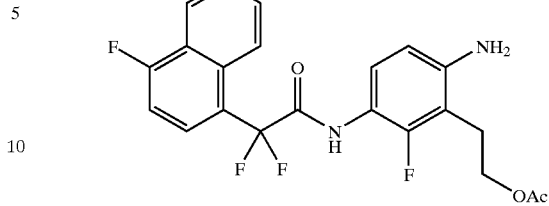

A mixture of 2-{3-[2,2-difluoro-2-(4-fluoronaphthyl)acetylamino]-2-fluoro-6-nitrophenyl}ethyl acetate (4.9 g, 10.5 mmol), as prepared in the preceding step, and Pd/C (10%, 500 mg) in ethanol (50 mL) and THF (50 mL) was stirred under hydrogen for 5 hours. The reaction mixture was filtered through Celite, and washed with THF and MeOH. The filtrate and washings were combined, concentrated in vacuo, and flash chromatographed on silica gel eluting with EtOAc/DCM (0 to 2%) to produce the title compound (3.8 g, 83%) as an off white solid. $^1$H-NMR (400 MHz, $CDCl_3$) δ 8.27 (d, J=8.2 Hz, 1H), 8.19 (d, J=8.6 Hz, 1H), 8.10 (s, 1H), 7.82 (m, 2H), 7.63 (m, 2H), 7.19 (t, J=8.6 Hz, 1H), 6.46 (d, J=8.7 Hz, 1H), 4.19 (t, J=7.4 Hz, 2H), 4.08 (s, 2H), 2.91 (t, J=7.3 Hz, 2H), 2.08 (s, 3H).

6. N-[4-Amino-2-fluoro-3-(2-hydroxyethyl)phenyl]-2,2-difluoro-2-(4-fluoronaphthyl)acetamide

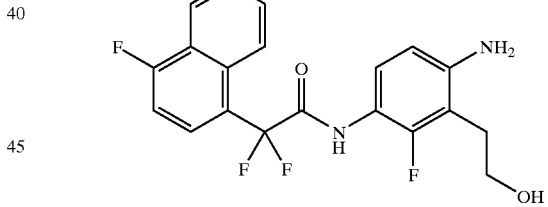

To a solution of 2-{2-amino-5-[2,2-difluoro-2-(4-fluoronaphthyl)acetylamino]-6-fluorophenyl}ethyl acetate (3.8 g, 8.8 mmol), as prepared in the preceding step, in MeOH (40 mL) and THF (20 mL) was added a solution of $K_2CO_3$ (1.68 g, 12 mmol) in water (30 mL). The mixture was stirred at room temperature for 3 hours. Additional water (50 mL) was added, and the resulting mixture was extracted with EtOAc (3×50 mL). The extracts were combined, washed with brine, dried over $Na_2SO_4$, and concentrated in vacuo to give the title compound (3.3 g, 96%) as an off white solid. $^1$H-NMR (400 MHz, $CDCl_3$) δ 8.27 (d, J=8.4 Hz, 1H), 8.19 (d, J=8.2 Hz, 1H), 8.13 (s, 1H), 7.81 (m, 2H), 7.64 (m, 2H), 7.19 (t, J=8.7 Hz, 1H), 6.47 (d, J=8.7 Hz, 1H), 4.07 (s, 2H), 3.89 (t, J=5.6 Hz, 2H), 2.85 (t, J=5.5 Hz, 2H).

7. N-[4-Chloro-2-fluoro-3-(2-hydroxyethyl)phenyl]-2,2-difluoro-2-(4-fluoronaphthyl)acetamide (Doyle, M. P., et al. *J. Org. Chem.*, 42:2426 (1977))

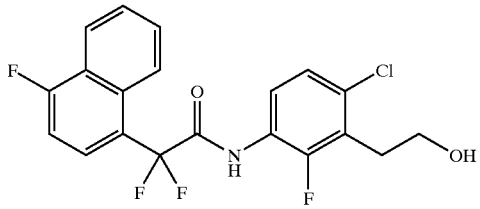

To a flask charged with copper(II) chloride (1.84 g, 13.7 mmol) was added a solution of tert-butylnitrite (1.46 g, 12.8 mmol, 90%, Aldrich) in acetonitrile (35 mL) under argon atmosphere. The resulting green reaction mixture was cooled in an ice-bath to 0° C., and a solution of N-[4-amino-2-fluor-3-(2-hydroxyethyl)phenyl]-2,2-difluoro-2-(4-fluoronaphthyl) acetamide (3.58 g, 9.13 mmol), as prepared according to the procedure of the preceding step, in acetonitrile (60 mL) was added over a period of 45 minutes. After stirring for an additional 6 hours at 0° C., the resulting brown mixture was allowed to warm up to ambient temperature, then poured into 20% aqueous HCl (160 mL), and extracted with DCM (3 times). The extracts were combined, washed with 20% HCl, $H_2O$, and brine, dried over $Na_2SO_4$, concentrated, and flash chromatographed on silica gel eluting with EtOAc/DCM (0 and 2.5%) to deliver the title compound (2.1 g, 56% yield) as a white solid. $^1$H-NMR (400 MHz, CDCl$_3$) δ 8.31 (br s, 1H), 8.24–8.12 (m, 3H), 7.84 (dd, J=8.2, 5.3 Hz, 1H). 7.68–7.60 (m, 2H), 7.22–7.20 (m, 2H), 3.87 (dd, J=12.6, 6.5 Hz, 2H), 3.09 (dt, J=6.7, 2.2 Hz, 2H), 1.47 (t, J=5.6 Hz, 2H). Mass spectrum (LCMS, ESI) calc'd for $C_{20}H_{15}ClF_4NO_2$ (M+H): 412.1. Found: 412.6.

8. 2-(3-{[2,2-Difluoro-2-(4-fluoronaphthyl)ethyl]amino}-6-chloro-2-fluorophenyl)ethanol

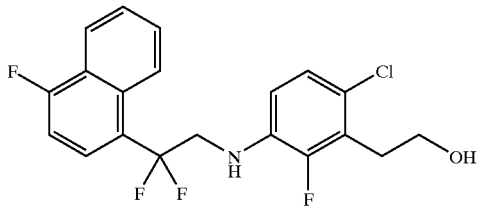

To a solution of N-[4-chloro-2-fluoro-3-(2-hydroxyethyl)phenyl]-2,2-difluoro-2-(4-fluoronaphthyl)acetamide (1.9 g, 4.6 mmol), as prepared in the preceding step, in THF (19 mL) at 0° C. was added dropwise a solution of $BH_3 \cdot$THF complex (19.4 mL, 19.4 mmol, 1.0 M in THF) over a period of 20 minutes, and the reaction mixture continued to stir until the ice bath expired. The mixture was then heated at reflux in an oil bath at 75 to 80° C. for 3 hours, and continued to stir at ambient temperature overnight. A solution of NaHCO$_3$ (1.63 g, 19.4 mmol) in $H_2O$ (20 mL) was added, the THF was evaporated, and the resulting mixture was extracted with DCM twice. The extracts were combined, washed with $H_2O$ and brine, dried over $Na_2SO_4$, concentrated, and flash chromatographed on silica gel eluting with EtOAc/DCM (0, 1, 1.5%) to give the title compound (805 mg, 44% yield) as a white solid. $^1$H-NMR (400 MHz, CDCl$_3$) δ 8.24–8.19 (m, 2H), 7.70–7.61 (m, 3H), 7.14 (t, J=9.3 Hz, 1H), 6.90 (dd, J=8.7, 1.6 Hz, 1H), 6.42 (t, J=8.9 Hz, 1H), 4.22–4.16 (m, 1H), 4.00 (dt, J=13.4, 6.8 Hz, 2H), 3.82 (dd, J=12.1, 6.4 Hz, 2H), 3.02 (dt, J=6.8, 2.3 Hz, 2H), 1.39 (br s, 1H). Mass spectrum (LCMS, ESI) calc'd for $C_{20}H_{17}ClF_4NO$ (M+H): 398.1. Found: 398.3.

9. 2-(3-{[2,2-Difluoro-2-(4-fluoronaphthyl)ethyl]amino}-6-chloro-2-fluorophenyl)ethanal

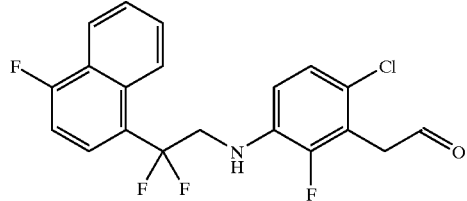

To a solution of DMSO (470 mg, 6.0 mmol), DIEA (823 μL, 4.74 mmol) and 2-(3-{[2,2-difluoro-2-(4-fluoronaphthyl)ethyl]amino}-6-chloro-2-fluorophenyl)ethanol (723 mg, 1.82 mmol), as prepared in the preceding step, in DCM (55 mL) in an ice-bath was added sulfur trioxide pyridine complex (754 mg, 4.74 mmol). After stirring for 3.5 hours the reaction mixture was diluted with DCM (110 mL). The organic layer was separated, and the aqueous layer extracted with DCM (100 mL). The organic layers were combined, washed with 10% citric acid (3 times), $H_2O$, and brine, dried over $Na_2SO_4$, and concentrated to give the title compound (722 mg, quantitative yield) as an orange oil. $^1$H-NMR (400 MHz, CDCl$_3$) δ 9.69 (d, J=1.1 Hz, 1H), 8.22–8.18 (m, 2H), 7.67–7.60 (m, 3H), 7.14 (t, J=9.2 Hz, 1H), 6.94 (d, J=8.8 Hz, 1H), 6.49 (t, J=8.7 Hz, 1H), 4.20 (bs, 1H), 4.00 (dt, J=13.3, 6.7 Hz, 2H), 3.83 (s, 2H).

10. 2-(3-{[2,2-Difluoro-2-(4-fluoronaphthyl)ethyl]amino}-6-chloro-2-fluorophenyl)acetic Acid

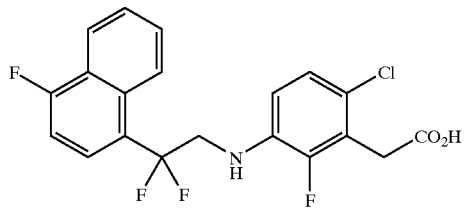

A solution of sodium chlorite (309 mg, 2.73 mmol, 80%) in $H_2O$ (3.0 mL) was added dropwise over a period of 30 minutes to a stirred mixture of 2-(3-{[2,2-difluoro-2-(4-fluoronaphthyl)ethyl]amino}-6-chloro-2-fluorophenyl)ethanal (722 mg, 1.82 mmol), as prepared in the preceding step, in DMSO (3.6 mL) and of NaH$_2$PO$_4$ (74 mg, 0.55 mmol) in $H_2O$ (0.9 mL). After the addition, the mixture was stirred at ambient temperature for 48 hours, then acidified with 10 M HCl to pH 1, and extracted with DCM (3 times). The extracts were combined, washed with $H_2O$ and brine, dried over $Na_2SO_4$, and concentrated in vacuo. The resulting residue was flash chromatographed on silica gel eluting with MeOH/DCM (0, 1, 1.5, and 2%) to give the starting aldehyde 2-(3-{[2,2-difluoro-2-(4-fluoronaphthyl)ethyl]amino}-6-chloro-2-fluorophenyl)ethanal (165 mg, 23% yield) and the title compound (570 mg, 76% yield) as a solid. $^1$H-NMR (400 MHz, CDCl$_3$) δ 8.32 (d, J=8.4 Hz, 1H), 8.15 (d, J=8.0 Hz, 1H), 7.71–7.61 (m, 3H), 7.18 (dd, J=9.8, 8.5 Hz, 1H), 6.78 (dd, J=8.8, 1.5 Hz, 1H), 6.44 (t, J=9.1 Hz, 1H), 4.05 (t, J=13.5 Hz, 2H), 3.69 (d, J=2.1 Hz, 2H).

11. tert-Butyl 2-aza-3-({2-[2-(3-{[2,2-difluoro-2-(4-fluoronaphthyl)ethyl]amino}-6-chloro-2-fluorophenyl)acetylamino]ethoxy}amino)-3-[(tert-butoxy)carbonylamino]prop-2-enoate

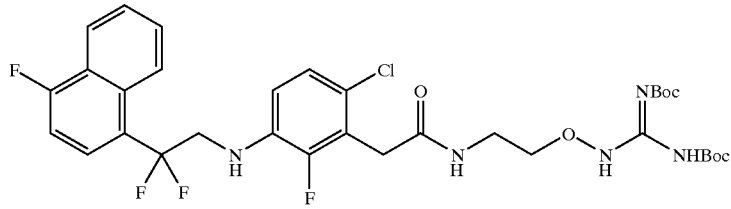

To a solution of 2-(3-{[2,2-difluoro-2-(4-fluoronaphthyl)ethyl]amino}-6-chloro-2-fluorophenyl)acetic acid (570 mg, 1.39 mmol), as prepared in the preceding step, in DMF (7.5 mL) in an ice-bath was added BOP (981 mg, 2.22 mmol), HCl salt of [N,N'-di(tert-butoxycarbonyl)]-2-aminoethoxyguanidine (689 mg, 1.94 mmol), and DIEA (0.96 mL, 5.55 mmol). After the ice-bath expired, the mixture continued to stir at ambient temperature overnight. Additional BOP (123 mg, 0.28 mmol) and the HCl salt of [N,N'-di(tert-butoxycarbonyl)]-2-aminoethoxyguanidine (98 mg, 0.28 mmol) were added, and the reaction mixture was stirred for 24 hours. The solvents were evaporated, and the resulting residue was partitioned between saturated $NaHCO_3$ and DCM. The organic layer was separated, and the aqueous layer was extracted with DCM. The organic layers were combined, washed with 10% $KHSO_4$, $H_2O$, and brine, dried over $Na_2SO_4$, concentrated, and flash chromatographed on silica gel eluting with MeOH/DCM (0, 0.5, and 1%) to give the title compound (720 mg, 73% yield) as a white foam. $^1$H-NMR (400 MHz, $CD_3OD$) δ 9.12 (s, 1H), 8.24–8.19 (m, 2H), 7.78–7.81 (m, 1H), 7.70–7.60 (m, 4H), 7.14 (dd, J=9.6, 8.4 Hz, 1H), 6.91 (dd, J=8.8, 1.6 Hz, 1H), 6.44 (t, J=8.8 Hz, 1H), 4.20–4.15 (m, 1H), 4.13–4 10 (m, 2H), 3.98 (dt, J=13.4, 6.7 Hz, 2H), 3.78 (d, J=1.9 Hz, 2H), 3.60 (dd, J=8.6, 4.9 Hz, 2H), 1.51 (s, 9H), 1.48 (s, 9H). Mass spectrum (LCMS, ESI) calc'd for $C_{33}H_{39}ClF_4N_5O_6$ (M+H): 712.2. Found: 712.3.

12. N-[2-(Amidinoaminooxy)ethyl]-2-(3-{[2,2-difluoro-2-(4-fluoronaphthyl)ethyl]amino}-6-chloro-2-fluorophenyl)acetamide Trifluoroacetate Salt

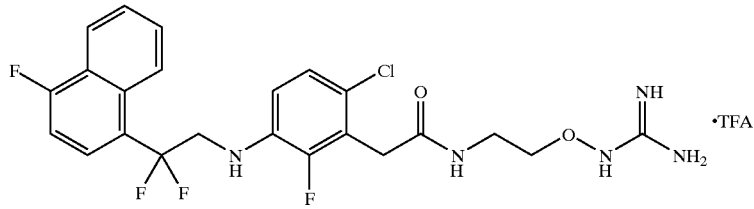

A solution of tert-butyl 2-aza-3-({2-[2-(3-{[2,2-di fluoro-2-(4-fluoronaphthyl)ethyl]amino}-6-chloro-2-fluorophenyl)acetyl amino]ethoxy}amino)-3-[(tert-butoxy)carbonylamino]prop-2-enoate (720 mg, 1.01 mmol), as prepared in the preceding step, in TFA/DCM (2:3, 30 mL) was stirred at ambient temperature for 4 hours. The solvents were evaporated, and the resulting residue was flash chromatographed on silica gel eluting with 0.05% TFA in MeOH/DCM (5 and 10%) to give the title compound (626 mg, 99% yield) as a pale brown foam. $^1$H-NMR (400 MHz, $CD_3OD$) δ 8.33 (d, J=8.5 Hz, 1H), 8.17–8.15 (m, 1H), 7.73–7.63 (m, 3H), 7.20 (dd, J=10.0, 8.3 Hz, 1H), 6.82 (dd, J=8.8, 1.6 Hz, 1H), 6.92 (t, J=9.1 Hz, H), 4.07 (t, J=13.7 Hz, 2H), 3.92 (t, J=5.4 Hz, 2H), 3.67 (d, J=1.8 Hz, 2H), 3.52–3.51 (m, 2H). Mass spectrum (LCMS, ESI) calc'd for $C_{23}H_{23}ClF_4N_5O_2$ (M+H): 512.1. Found: 512.2.

Example 5

N-[(6-Amino-2-methyl(3-pyridyl))methyl]-2-(3-{[2,2-difluoro-2-(4-fluoronaphthyl)ethyl]amino}-6-chloro-2-fluorophenyl)acetamide Hydrochloride Salt

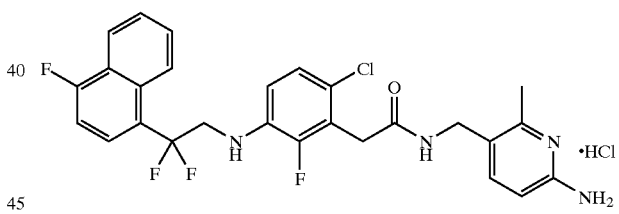

1. 2-(3-{[2,2-Difluoro-2-(4-fluoronaphthyl)ethyl]amino}-6-chloro-2-fluorophenyl)-N-({6-[(tert-butoxy)carbonylamino]-2-methyl(3-pyridyl)}methyl)acetamide

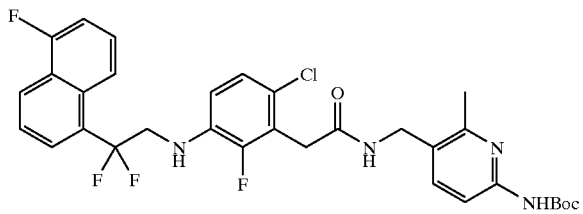

To a solution of 2-(3-{[2,2-difluoro-2-(4-fluoronaphthyl)ethyl]amino}-6-chloro-2-fluorophenyl)acetic acid (15 mg, 37 μmol), as prepared according to the procedure of step 10 of Example 4, in DMF (0.3 mL) was added BOP (26 mg, 58 μmol), N-[5-(aminomethyl)-6-methyl(2-pyridyl)](tert-butoxy)carboxamide (12 mg, 51 μmol), and a solution of DIEA (19 mg, 146 μmol) in DMF (0.1 mL) (Sanderson, P. E., et al., WO 97/01338 (1997)). The mixture was stirred overnight, the solvents evaporated, and the resulting mixture was partitioned between saturated NaHCO₃ and DCM. The organic layer was separated, and the aqueous layer extracted with DCM. The organic layers were combined, washed with 10% KHSO₄, H₂O, and brine, dried over Na₂SO₄, concentrated, and flash chromatographed on silica gel eluting with MeOH/DCM (0.3, 0.6, and 1%) to give the title compound (11 mg, 49% yield) as a white solid. ¹H-NMR (400 MHz, CD₃OD) δ 8.33 (d, J=8.4 Hz, 1H), 8.17–8.14 (m, 1H), 7.72–7.61 (m, 4H), 7.55 (d, J=8.5 Hz, 1H), 7.19 (dd, J=10.0, 8.3 Hz, 1H), 6.81 (dd, J=8.8, 1.7 Hz, 1H), 6.47 (t, J=9.1 Hz, 1H), 4.32 (s, 2H), 4.12–4.03 (m, 2H), 3.67 (d, J=2.0 Hz, 2H), 2.40 (s, 3H), 1.50 (s, 9H). Mass spectrum (LCMS, ESI) calc'd for C₃₂H₃₂ClF₄N₄O₃ (M+H): 631.2. Found: 631.1.

2. N-[(6-Amino-2-methyl(3-pyridyl))methyl]-2-(3-{[(2,2-difluoro-2-(4-fluoronaphthyl)ethyl]amino}-6-chloro-2-fluorophenyl)acetamide Hydrochloride Salt

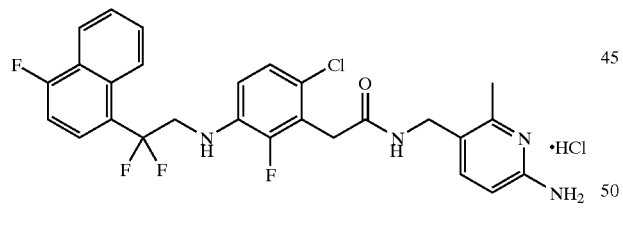

A solution of 2-(3-{[2,2-difluoro-2-(4-fluoronaphthyl)ethyl]amino}-6-chloro-2-fluorophenyl)-N-({6-[(tert-butoxy)carbonylamino]-2-methyl(3-pyridyl)}methyl)acetamide (10 mg, 16 μmol), as prepared in the preceding step, in HCl (0.5 mL, 4.0 M in 1,4-dioxane) was stirred for 2 hours at ambient temperature. A solution of MeOH/DCM (25%, 0.4 mL) was added, and the mixture continued to stir overnight. The solvents were evaporated, and the resulting brown residue was flash chromatographed on silica gel eluting with MeOH/DCM (2.5, 5, and 10%) to give a solid product. It was treated with HCl solution (0.01 mL, 4.0 M in 1,4-dioxane, 40 μmol) in DCM (0.5 mL), stirred for 5 minutes, and the solvents evaporated to give the title compound (6.2 mg, 69% yield) as a white solid. ¹H-NMR (400 MHz, CD₃OD) δ 8.26 (d, J=8.4 Hz, 1H), 8.17–8.14 (m, 1H), 7.80 (d, J=9.1 Hz, 1H), 7.73–7.64 (m, 4H), 7.20 (dd, J=10.0, 8.3 Hz, 1H), 6.82–6.79 (m, 1H), 6.49 (t, J=9.1 Hz, 1H), 4.24 (s, 2H), 4.10–4.02 (m, 2H), 3.66 (d, J=2.3 Hz, 2H), 2.49 (s, 3H). Mass spectrum (LCMS, ESI) calc'd for C₂₇H₂₄ClF₄N₄O (M+H): 531.1. Found: 531.6.

Example 6

N-[2-(Guanidinooxy)ethyl]-2-(3-{[benzylsulfonyl]amino}phenyl)acetamide Trifluoroacetate Salt

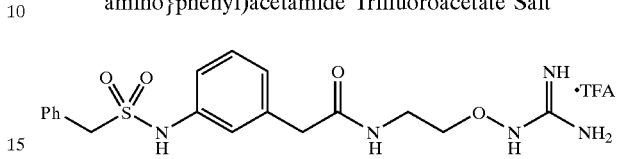

1. N-(2-Hydroxyethyl)-2-(3-nitrophenyl)acetamide

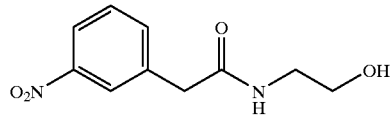

To a solution of 3-nitrophenylacetic acid (3.21 g, 17.7 mmol), ethanolamine (2.8 g, 46 mmol), and triethylamine (3.0 mL, 22 mmol) in anhydrous DMF (110 mL) was added a solution of benzotriazole-1-yl-oxy-tris-pyrrolidinophosphonium hexafluorophosphate (PyBOP, 9.37 g, 18.0 mmol) in anhydrous DMF (80 mL). After stirring 16 hours at ambient temperature (under nitrogen), the reaction mixture was concentrated in vacuo, dissolved in DCM and filtered. The filtrate was washed with 10% aqueous citric acid, saturated aqueous NaHCO₃, pH 7 buffer, and brine, dried over Na₂SO₄ and filtered. The evaporated filtrate was then purified by flash chromatography (10% methanol in DCM) giving the title compound (1.02 g, 26%) as a light yellow solid. ¹H NMR (300 MHz, CDCl₃/CD₃OD) δ 8.18 (m, 1H), 8.11 (ddd, 1H, J=8.1 Hz, 2.4 Hz, 1.1 Hz), 7.72 (m, 1H), 7.60 (t, 1H, J=7.8 Hz), 3.62 (s, 2H), 3.44 (t, 2H, J=5.9 Hz), 3.16 (t, 2H, J=5.9 Hz).

2. N-[2-(N'-Phthalimidyl)hydroxyethyl]-2-(3-nitrophenyl)acetamide

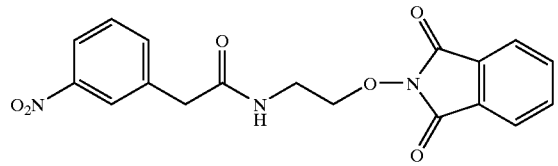

To a solution of the product of the preceding step (1.02 g, 4.55 mmol), N-hydroxyphthalimide (0.76 g, 4.64 mmol), and triphenylphosphine (1.22 g, 4.65 mmol) in anhydrous THF (100 mL) was added diethylazadicarboxylate (0.75 mL, 4.77 mmol) via syringe. After stirring overnight at ambient temperature (under nitrogen), the reaction was concentrated in vacuo and purified by flash chromatography (40% ethyl acetate in DCM) giving an impure product that was dissolved in DCM, cooled, and filtered. The evaporated filtrate was then purified by flash chromatography (66%–100% ethyl acetate in hexane) giving the title compound (0.86 g, 51%) as a white solid. ¹H NMR (300 MHz, CDCl₃) δ 8.26 (t, 1H, J=1.7 Hz), 8.15 (ddd, 1H, J=8.3 Hz, 2.3 Hz, t, 1.0 Hz), 7.82 (m, 4H), 7.74 (m, 1H), 7.53 (t, 1H, J=7.9 Hz), 7.03 (br s, 1H), 4.26 (m, 2H), 3.76 (s, 2H), 3.57 (dd, 2H, J=9.8 Hz, 5.7 Hz).

3. N-[2-(N'-Phthalimidyl)hydroxyethyl]-2-(3-aminophenyl)acetamide

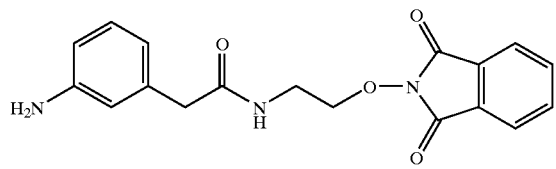

A solution of the product of the preceding step (0.66 g, 1.80 mmol) and 10% palladium on carbon (15 mg) in degassed 1:1 ethanol:THF (40 mL) was stirred under hydrogen at ambient temperature. After 6 hours the reaction was filtered over Celite and the filtrate evaporated and purified by flash chromatography (5% methanol in DCM) giving the title compound (0.20 g, 33%) as a yellow solid. ¹H NMR (300 MHz, CDCl₃) δ 7.81 (m, 4H), 7.14 (t, 1H, J=8.0 Hz), 6.72 (m, 2H), 6.61 (ddd, 1H, J=8.0 Hz, 2.2 Hz, 1.0 Hz), 4.23 (m, 2H), 3.55 (m, 4H). Mass spectrum (MALDI-TOF, α-cyano-4-hydroxycinnamic acid matrix) calc'd. for C₁₈H₁₇N₃O₄: 362.1 (M+Na), 340.1 (M+H). Found: 362.2, 340.3.

4. N-[2-(N'-Phthalimidyl)hydroxyethyl]-2-(3-{[benzylsulfonyl]-amino}phenyl)acetamide

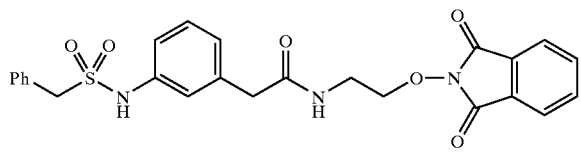

To an ice-cold solution of the product of the preceding step (0.20 g, 0.58 mmol) in anhydrous DCM (50 mL) was added a solution of α-toluenesulfonyl chloride (0.11 g, 0.58 mmol) in anhydrous DCM (20 mL) followed by N-methylmorpholine (0.10 mL, 0.91 mmol). After stirring 16 hours at ambient temperature, more α-toluenesulfonyl chloride (0.07 g, 0.36 mmol) and N-methylmorpholine (0.10 mL, 0.91 mmol) were added and the reaction stirred an additional 4 hours and evaporated in vacuo. The residue was dissolved in DCM, washed with 10% aqueous citric acid, pH 7 buffer and brine, dried over Na₂SO₄, filtered, and the filtrate evaporated giving the title compound (0.20 g, 69%) as a light yellow solid. ¹H NMR (300 MHz, CDCl₃) δ 7.77 (m, 4H), 7.35 (m, 1H), 7.22 (s, 5H), 7.17 (m, 1H), 7.11 (m, 1H), 7.05 (s, 1H), 6.71 (br m, 1H), 4.37 (s, 2H), 4.25 (m, 2H), 3.64 (s, 2H), 3.64 (dd, 2H, J=10 Hz, 5.5 Hz).

5. N-[2-(Aminooxy)ethyl]-2-(3-{[benzylsulfonyl]amino}phenyl)acetamide

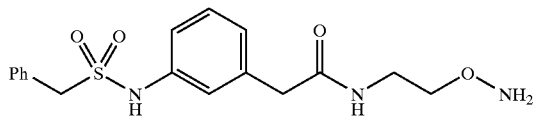

The product of the preceding step (0.19 g, 0.39 mmol) was dissolved in 1:1 ethanol:THF (20 mL) and reacted with 40% aqueous methylamine (10 mL) for 1 hour at ambient temperature. The reaction was evaporated in vacuo and purified on a Waters Sep-Pak (5 g silica, 1:1 DCM:ethyl acetate) giving an impure yellow solid. This was then purified by preparative thin layer chromatography (10% methanol in DCM) giving the title compound (0.10 g, 72%) as a white solid. ¹H NMR (300 MHz, CDCl₃/CD₃OD) δ 7.34 (m, 3H), 7.28 (m, 3H), 7.10 (m, 1H), 7.05 (m, 2H), 4.35 (s, 2H), 3.69 (1, 2H, J=5 Hz), 3.51 (s, 2H), 3.43 (t, 2H, J=5 Hz). Mass spectrum (MALDI-TOF, α-cyano-4-hydroxycinnamic acid matrix) calc'd. for C₁₇H₂₁N₃O₄S: 386.1 (M+Na). Found: 386.6.

6. N-[2-({N,N'-Di[tert-butoxycarbonyl]}guanidinooxy)ethyl]-2-(3-{[benzylsulfonyl]amino}phenyl)acetamide

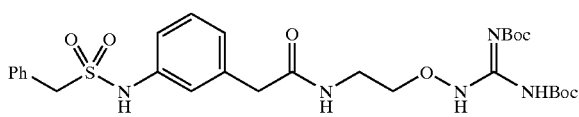

A solution of the product of the preceding step (89 mg, 0.24 mmol) and [N,N'-di(tert-butoxycarbonyl)] amidinopyrazole (86 mg, 0.28 mmol) in DMF (5 mL) was stirred for 4 days at ambient temperature. The reaction was evaporated in vacuo and the crude product purified by flash chromatography (5% methanol in DCM) giving an impure yellow oil. This was then purified by preparative thin layer chromatography (5% methanol in DCM) giving the title compound (72 mg, 49%) as a colorless solid. ¹H NMR (300 MHz, CDCl₃) δ 9.19 (s, 1H), 8.22 (br t, 1H, J=5.0 Hz), 7.62 (s, 1H), 7.23 (m, 10H (Ar+NH)), 4.27 (s, 2H), 4.08 (m, 2H), 3.57 (m, 4H), 1.51 (s, 9H), 1.49 (s, 9H).

7. N-[2-(Guanidinooxy)ethyl]-2-(3-{[benzylsulfonyl]amino}phenyl) acetamide Trifluoroacetate Salt

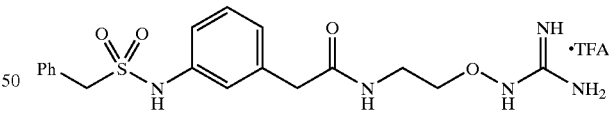

The product of the preceding step (72 mg, 0.12 mmol) was dissolved in DCM (5 mL) and reacted with trifluoroacetic acid (2 mL) for 4 hours at ambient temperature. The reaction was concentrated in vacuo and the crude product purified by preparative thin layer chromatography (20% methanol in DCM) giving the title compound (44 mg, 71%) as a pale yellow wax. ¹H NMR (300 MHz, CDCl₃/CD₃OD) δ 7.34 (m, 3H), 7.28 (m, 3H), 7.11 (m, 1H), 7.05 (m, 2H), 4.35 (s, 2H), 3.90 (t, 2H, J=4.9 Hz), 3.52 (s, 2H), 3.47 (t, 2H, J=4.8 Hz). Mass spectrum (MALDI-TOF, α-cyano-4-hydroxycinnamic acid matrix) calc'd. for C₁₈H₂₃N₅O₄S: 428.1 (M+Na), 406.2 (M+H). Found: 428.4, 406.4.

Example 7

N-[2-(Guanidinooxy)ethyl]-2-(2-chloro-5-{[benzylsulfonyl]amino}phenyl) acetamide Trifluoroacetate Salt

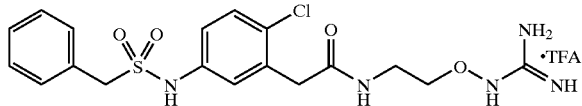

1. 2-Chloro-5-nitrophenylacetic Acid Monohydrate

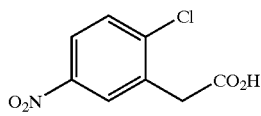

A solution of 2-chlorophenylacetic acid (10.0 g, 58.6 mmol) in concentrated sulfuric acid (40 mL) was cooled to −10° C. and slowly reacted with a solution of fuming nitric acid (2.80 mL, 66.7 mmol) in concentrated sulfuric acid (7.2 mL). After 2.5 hours the reaction was slowly poured over ice water (400 mL), filtered over a coarse filter frit, washed once with cold water, and dried on the frit overnight giving the title compound (13.5 g, 98%) as a white solid. Integration of the proton NMR spectrum showed the product contained about 0.2 equivalents of 2-chlorophenylacetic acid, but thin-layer chromatography showed this to be inseparable from the product. $^1$H NMR (300 MHz, CDCl$_3$/CD$_3$OD) δ 8.25 (d, 1H, J=2.7 z), 8.13 (dd, 1H, J=8.7 Hz, 2.7 Hz), 7.61 (d, 1H, J=8.8 Hz), 3.89 (s, 2H).

2. Ethyl 2-(3-amino-6-chlorophenyl)acetate

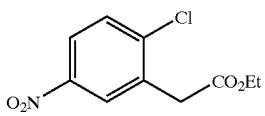

The product of the preceding step (4.14 g, 17.7 mmol) was suspended in DCM (70 mL) and reacted with oxalyl chloride (4.0 mL, 46 mmol) and a few drops of DMF. After stirring 1 hour at ambient temperature the reaction became homogeneous, reagent grade ethanol (30 mL) was added and the reaction stirred another 30 minutes. The crude product was evaporated in vacuo and purified by flash chromatography (10% to 15% ethyl acetate in hexane) giving the title compound (4.6 g) as a pale yellow oil. Proton NMR showed the product contained about 0.8 equivalents of diethyloxalate that could not be located by thin-layer chromatography. $^1$H NMR (300 MHz, CDCl$_3$) δ 8.21 (d, 1H, J=2.7 Hz), 8.11 (dd, 1H, J=8.8 Hz, 2.7 Hz), 7.57 (d, 1H, J=8.8 Hz), 4.21 (q, 2H, J=7.2 Hz), 3.87 (s, 2H), 1.28 (t, 3H, J=7.2 Hz).

3. Ethyl 2-(3-amino-6-chlorophenyl)acetate

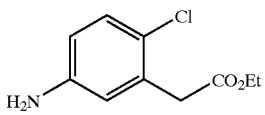

A solution of the product of the preceding step (2.00 g, 8.21 mmol) in reagent grade ethanol (50 mL) was reacted with tin(II)chloride dihydrate (9.40 g, 41.7 mmol) at ambient temperature. After 16 hours the reaction was concentrated in vacuo, dissolved in DCM and filtered. The filtrate was washed with water and brine, dried over Na$_2$SO$_4$, and filtered. The evaporated filtrate was then purified by flash chromatography (40% ethyl acetate in hexane) giving the title compound (0.53 g, 30%) as a pale yellow oil. $^1$H NMR (300 MHz, CDCl$_3$) δ 7.12 (d, 1H, J=8.5 Hz), 6.60 (d, 1H, J=2.8 Hz), 6.53 (dd, 1H, 8.5 Hz, 2.9 Hz), 4.17 (q, 2H, J=7.1 Hz), 3.65 (s, 2H), 1.26 (t, 3H, J=7.1 Hz).

4. Ethyl 2-(2-chloro-5-{[benzylsulfonyl]amino}phenyl)acetate

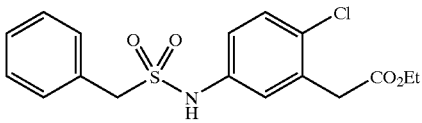

A solution of the product of the preceding step (0.50 g, 2.32 mmol) and α-toluenesulfonyl chloride (0.74 g, 3.88 mmol) in DCM (40 mL) and N-methylmorpholine (0.80 mL, 7.3 mmol) was stirred at ambient temperature for 3 hours, washed with dilute aqueous HCl, water, and brine, dried over Na$_2$SO$_4$, and filtered. The evaporated filtrate was purified by flash chromatography (5% ethyl acetate in DCM) giving the title compound (0.693 g, 81%) as a pale yellow solid. $^1$H NMR (300 MHz, CDCl$_3$) δ 7.36 (m, 4H), 7.26 (m, 2H), 7.04 (d, 1H, J=2.7 Hz), 6.99 (dd, 1H, J=8.5 Hz, 2.8 Hz), 6.47 (br s, 1H), 4.33 (s, 2H), 4.20 (q, 2H, J=7.1 Hz), 3.73 (s, 2H), 1.29 (t, 3H, J=7.1 Hz). Mass spectrum (MALDI-TOF, α-cyano-4-hydroxycinnamic acid matrix) calc'd. for C$_{17}$H$_{18}$NO$_4$SCl: 390.1 (M+Na). Found: 390.7.

5. 2-(2-Chloro-5-{[benzylsulfonyl]amino}phenyl) acetic Acid

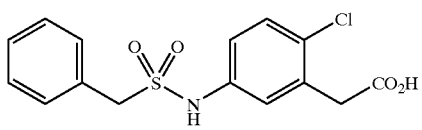

A solution of the product of the preceding step (0.69 g, 1.87 mmol) in 1:1 water/THF (20 mL) was reacted with potassium hydroxide (0.52 g, 9.32 mmol) at ambient temperature for 20 hours. After evaporating the THF in vacuo, the remaining aqueous layer was acidified to pH 3 with 1N HCl and extracted with DCM and ether. The combined organic layers were washed with brine, dried over Na$_2$SO$_4$, and filtered. The filtrate was then evaporated in vacuo to give the title compound (0.586 g, 92%) as a white solid. $^1$H NMR (300 MHz, CDCl$_3$/CD$_3$OD) δ 7.34 (m, 4H), 7.28 (m, 2H), 7.07 (m, 2H), 4.34 (s, 2H), 3.73 (s, 2H). Mass spectrum (MALDI-TOF, α-cyano-4-hydroxycinnamic acid matrix) calc'd. for C$_{15}$H$_{14}$NO$_4$SCl: 378.0 (M+K), 362.0 (M+Na). Found. 378.8, 362.9.

6. N-[2-({N,N'-Di-[tert-butoxycarbonyl]}guanidinooxy)ethyl]-2-(2-chloro-5-{[benzylsulfonyl]amino}phenyl)acetamide

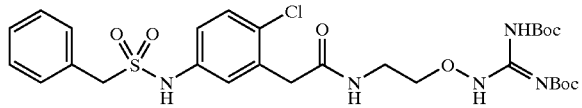

A solution of the product of the preceding step (0.21 g, 0.60 mmol) and [N,N'-di(tert-butoxycarbonyl)]-2-aminoethoxyguanidine (Tianbao Lu, et al., WO 99/26926 (1999)) (0.19 g, 0.60 mmol), in anhydrous THF (50 mL) was reacted with BOP (0.33 g, 0.75 mmol) and triethylamine (0.25 mL, 1.8 mmol) at ambient temperature for 16 hours. The reaction was evaporated in vacuo, dissolved in DCM, washed with pH 7 buffer and brine, dried over $Na_2SO_4$, and filtered. The evaporated filtrate was purified by flash chromatography (5% methanol in DCM) giving the title compound (0.380 g, 98%) as an orange solid. $^1$H NMR (300 MHz, $CDCl_3$) δ 9.14 (s, 1H), 8.22 (br t, 1H, J=5.0 Hz), 7.60 (s, 1H), 7.34 (m, 3H), 7.28 (m, 3H), 7.10 (d, 1H, J=2.6 Hz), 7.03 (dd, 1H, J=8.6 Hz, 2.7 Hz), 6.84 (br s, 1H), 4.29 (s, 2H), 4.13 (m, 2H), 3.75 (s, 2H), 3.62 (dd, 2H, J=8.8 Hz, 5.1 Hz), 1.51 (s, 9H), 1.46 (s, 9H). Mass spectrum (MALDI-TOF, gentisic acid matrix) calc'd. for $C_{28}H_{38}N_5O_8S$ Cl: 662.2 (M+Na), 440.1 (M−2 Boc+H). Found: 661.7, 439.9.

7. N-[2-(Guanidinooxy)ethyl]-2-(2-chloro-5-{[benzylsulfonyl]-amino}phenyl)acetamide Trifluoroacetate Salt

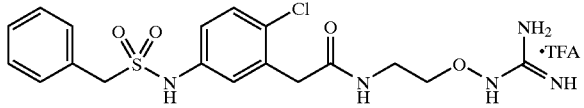

A solution of the product of the preceding step (0.375 g, 0.586 mmol) in DCM (10 mL) was reacted with trifluoroacetic acid (5 mL) at ambient temperature for 16 hours. The reaction was evaporated in vacuo, and the crude product purified by flash chromatography (20% methanol in DCM) giving the title compound (0.326 g, 100%) as a pale yellow solid. $^1$H NMR (300 MHz, $CDCl_3/CD_3OD$) δ 7.34 (m, 3H), 7.29 (m, 3H), 7.06 (m, 2H), 4.35 (s, 2H), 3.94 (br t, 2H, J=5 Hz), 3.65 (s, 2H), 3.49 (br t, 2H, J=5 Hz). Mass spectrum (MALDI-TOF, α-cyano-4-hydroxycinnamic acid matrix) calc'd. for $C_{18}H_{22}N_5O_4SCl$: 462.1 (M+Na), 440.1 (M+H). Found: 461.9, 439.9.

Example 8

N-[2-(Guanidinooxy)ethyl]-2-(2-methyl-5-{[benzylsulfonyl]amino}phenyl)acetamide Trifluoroacetate Salt

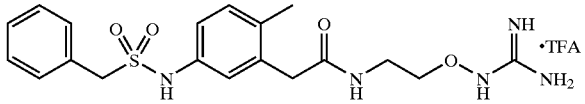

1. (2-Methyl-5-nitrophenyl)methanol

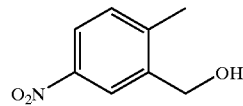

2-Methyl-5-nitrobenzoic acid (2.00 g, 11.0 mmol) was warmed under nitrogen, dissolved in anhydrous THF (25 mL), and treated with a 1N solution of borane in THF (16.5 mL). After stirring 18 hours at ambient temperature the reaction was quenched with a solution of potassium carbonate (1.8 g, 13 mmol) in water (50 mL), and the THF removed in vacuo. The remaining aqueous solution was extracted with DCM, and the organic layer washed with pH 7 buffer and brine, dried over sodium sulfate, and filtered. The evaporated filtrate gave the title compound as a pale yellow solid (1.76 g, 95%). $^1$H NMR (300 MHz, $CDCl_3$) δ 8.29 (d, 1H, J=2.5 Hz), 8.04 (dd, 1H, J=8.3 Hz, 2.5 Hz), 7.31 (d, 1H, J=8.31 Hz), 4.77 (d, 2H, J=5.5 Hz), 2.41 (s, 3H), 2.09 (t, 1H, J 5.6 Hz).

2. (2-Methyl-5-nitrophenyl)methyl Methylsulfonate

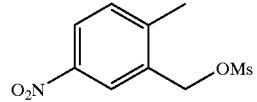

A solution of the product of the preceding step (1.74 g, 10.4 mmol) in DCM (50 mL) was cooled to 0° C. and treated with methanesulfonyl chloride (0.90 mL, 11.6 mmol) and triethylamine (1.75 mL, 12.6 mmol). After stirring 30 minutes the reaction was warmed to ambient temperature, stirred another 30 minutes, and poured onto pH 7 buffer solution. The phases were separated and the organic layer washed with brine, dried over sodium sulfate, and filtered. The evaporated filtrate gave the title compound as a pale yellow oil (2.53 g, 99%). $^1$H NMR (300 MHz, $CDCl_3$) δ 8.26 (d, 1H, J=2.5 Hz), 8.16 (dd, 1H, J=8.4 Hz, 2.4 Hz), 7.42 (d, 1H, J=8.4 Hz), 5.31 (s, 2H), 3.08 (s, 3H), 2.51 (s, 3H).

3. 2-(2-Methyl-5-nitrophenyl)ethanenitrile

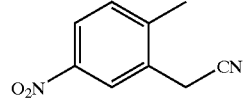

The product of the preceding step (2.48 g, 10.1 mmol) and potassium cyanide (2.00 g, 30.7 mmol) were refluxed in acetonitrile (100 mL) for 8 hours, then cooled to ambient temperature and stirred overnight. The reaction was evaporated in vacuo, dissolved in DCM, and filtered. The filtrate was washed with pH 7 buffer and brine, evaporated, and purified by flash column chromatography (1:1 hexane:ethyl acetate eluant) giving the title compound (1.27 g, 71%) as a yellow solid. $^1$H NMR (300 MHz, $CDCl_3$) δ 8.26 (d, 1H, J=2.4 Hz), 8.13 (dd, 1H, J=8.3 Hz, 2.4 Hz), 7.42 (d, 1H, J=8.3 Hz), 3.78 (s, 2H), 2.48 (s, 3H).

4. 2-(2-Methyl-5-nitrophenyl)acetic Acid

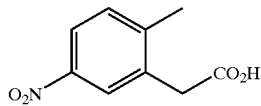

To a solution of the product of the preceding step (1.27 g, 7.21 mmol) in methanol (30 mL) was added a solution of potassium hydroxide (4.06 g, 72.4 mmol) in water (30 mL). The reaction was heated at reflux overnight and the methanol removed in vacuo. The remaining aqueous layer was acidified with 3N HCl and filtered, the solid washed with diethyl ether, and the filtrate separated. The aqueous layer was washed with DCM and diethyl ether, and the combined organic layers washed with brine, dried over sodium sulfate, and filtered. The evaporated filtrate gave the title compound (0.84 g, 60%) as an orange solid. $^1$H NMR (300 MHz, acetone-$d_6$) δ 8.17 (d, 1H, J=2.3 Hz), 8.06 (dd, 1H, J=8.4 Hz, 2.5 Hz), 7.29 (d, 1H, J=8.4 Hz), 3.88 (s, 2H), 2.45 (s, 3H).

5. N-[2-({N,N'-Di-[tert-butoxycarbonyl]}guanidinooxy)ethyl]-2-(2-methyl-5-nitrophenyl)acetamide

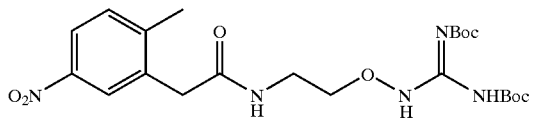

A solution of the product of the preceding step (0.27 g, 1.40 mmol), BOP (0.70 g, 1.58 mmol), triethylamine (0.50 mL, 3.60 mmol), and [N,N'-di(tert-butoxycarbonyl)]2-aminoethoxyguanidine (Tianbao Lu, et al., WO 99/26926 (1999)) (0.44 g, 1.38 mmol), in anhydrous DMF were stirred at ambient temperature overnight. The reaction was concentrated in vacuo and the crude product purified by flash column chromatography (5% methanol in DCM eluant) giving the title compound as a pale orange solid (0.63 g, 92%). $^1$H NMR (300 MHz, CDCl$_3$) δ 9.21 (s, 1H), 8.42 (m, 1H), 8.17 (d, 1H, J=2.4 Hz), 7.99 (dd, 1H, J=8.4 Hz, 2.5 Hz), 7.59 (s, 1H), 7.29 (d, 1H, J=8.4 Hz), 4.12 (m, 2H), 3.74 (s, 2H), 3.63 (m, 2H), 2.48 (s, 3H), 1.52 (s, 9H), 1.47 (s, 9H).

6. N-[2-({N,N'-Di-[tert-butoxycarbonyl]}guanidinooxy)ethyl]-2-(3-amino-6-methylphenyl)acetamide

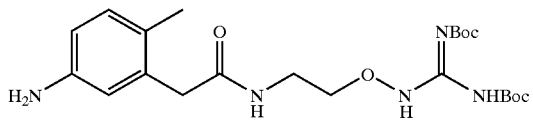

The product of the preceding step (0.29 g, 0.58 mmol) and 10% palladium (0) on carbon (0.06 g) were dissolved in reagent ethanol (50 mL), degassed with nitrogen and vacuum, and stirred under a hydrogen balloon at ambient temperature. After 4 hrs the reaction was filtered over Celite, the frit washed with methanol, and the filtrate evaporated in vacuo giving the title compound (0.27 g, 100%). $^1$H NMR (300 MHz, CDCl$_3$) δ 9.10 (s, 1H) 7.61 (s, 1H), 7.30 (m, 1H), 6.94 (d, 1H, J=8.0 Hz), 6.63 (d, 1H, J=2.4 Hz), 6.51 (dd, 1H, J=8.0 Hz, 2.5 Hz), 4.09 (m, 2H), 3.58 (m, 2H), 3.53 (s, 2H), 2.21 (s, 3H), 1.52 (s, 9H), 1.47 (s, 9H).

7. N-[2-({N,N'-Di-[tert-butoxycarbonyl]}guanidinooxy)ethyl]-2-(2-methyl-5-{[benzylsulfonyl]amino}phenyl)acetamide

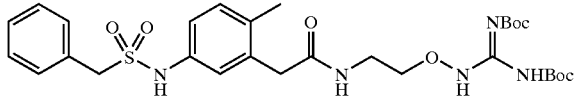

The product of the preceding step (0.27 g, 0.58 mmol), α-toluenesulfonyl chloride (0.18 g, 0.96 mmol), and N-methylmorpholine (0.20 mL, 1.82 mmol) were stirred at ambient temperature in DCM (20 mL). After 2 hours the reaction was diluted with additional DCM and washed with dilute aqueous HCl, saturated aqueous sodium bicarbonate, pH 7 buffer, and brine. The organic layer was dried over sodium sulfate, filtered, and the filtrate concentrated in vacuo giving the title compound as a pale yellow solid (0.35 g, 97%). $^1$H NMR (300 MHz, CDCl$_3$) δ 9.15 (s, 1H), 8.04 (br t, 1H, J=5 Hz), 7.60 (s, 1H), 7.34 (m, 5H), 7.12 (d, 1H, J=8.0 Hz), 7.03 (dd, 1H, J=11 Hz, 2.3 Hz), 6.26 (s, 1H), 4.31 (s, 2H), 4.12 (m, 2H), 3.63 (m, 4H), 2.33 (s, 3H), 1.51 (s, 9H), 1.45 (s, 9H).

8. N-[2-(Guanidinooxy)ethyl]-2-(2-methyl-5-{[benzylsulfonyl]-amino}phenyl)acetamide Trifluoroacetate Salt

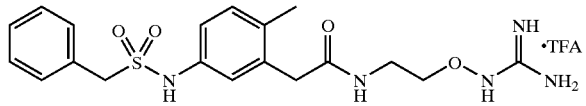

The product of the preceding step (0.35 g, 0.56 mmol) was dissolved in DCM (10 mL) and treated with trifluoroacetic acid (3 mL) at ambient temperature. After 16 hours the reaction was concentrated in vacuo and the crude product purified on a 10 g Waters silica Sep-Pak® (5 to 20% methanol in DCM gradient elution) giving the title compound as a pale yellow solid (0.27 g, 89%). $^1$H NMR (300 MHz, CDCl$_3$/CD$_3$OD) δ 7.34 (m, 3H), 7.29 (m, 2H), 7.14 (d, 1H, J=9.0 Hz), 7.02 (dd, 1H, J=6.5 Hz, 2.3 Hz), 7.00 (s, 1H), 4.33 (s, 2H), 3.92 (br t, 2H, J=5 Hz), 3.55 (s, 2H), 3.48 (br t, 2H, J=5 Hz), 2.28 (s, 3H). Mass spectrum (MALDI-TOF, gentisic acid matrix) calc'd. for C$_{19}$H$_{25}$N$_5$O$_4$S: 442.2 (M+Na), 420.2 (M+H). Found: 442.5, 420.6.

Example 9

N-[2-(Guanidinooxy)ethyl]-2-(2-hydroxy-6-methyl-3-{[(3-methylphenyl)sulfonyl]amino}phenyl)acetamide Hydrochloride Salt

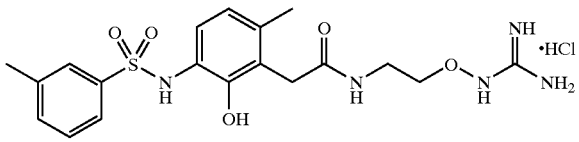

1. 4-Methyl-1-nitro-2-prop-2-enyloxybenzene

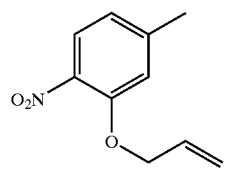

A solution of 5-methyl-2-nitrophenol (2.00 g, 13.1 mmol), allyl bromide (1.30 mL, 15.0 mmol), and cesium carbonate (5.5 g, 17 mmol) in DMF (100 mL) was stirred at ambient temperature. After 20 hrs the reaction was filtered, frit washed with methanol, and the filtrate evaporated in vacuo at 50° C. The residue was purified by flash column chromatography (4:1 then 2:1 hexane:ethyl acetate eluant) giving the title compound as a yellow oil (2.39 g, 95%) that crystallized after sitting 3 days at ambient temperature. $^1$H NMR (300 MHz, CDCl$_3$) δ 7.79 (d, 1H, J=8.2 Hz), 6.86 (s, 1H), 6.82 (m, 1H), 6.05 (ddt, 1H, J=17.3 Hz, 10.6 Hz, 5.0 Hz), 5.50 (ddd, 1H, J=17.3 Hz, 3.3 Hz, 1.7 Hz), 5.33 (ddd, 1H, J=10.6 Hz, 2.9 Hz, 1.5 Hz), 4.67 (dt, 2H, J=4.9 Hz, 1.6 Hz), 2.40 (s, 3H).

2. 3-Methyl-6-nitro-2-prop-2-enylphenol

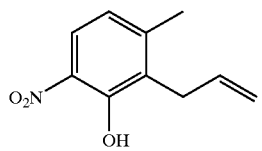

4-Methyl-1-nitro-2-prop-2-enyloxybenzene (7.11 g, 36.8 mmol), prepared as in the preceding step, was heated neat at 200° C. under nitrogen for 3 hours, cooled to ambient temperature, and purified by flash column chromatography (1:1 hexane:DCM eluant) giving the title compound as an orange oil (5.04 g, 71%). $^1$H NMR (300 MHz, CDCl$_3$) δ 11.07 (s, 1H), 7.90 (d, 1H, J=8.7 Hz), 6.80 (d, 1H, J=8.7 Hz), 5.93 (m, 1H), 5.03 (m, 1H), 4.96 (m, 1H), 3.50 (dt, 2H, J=5.9 Hz, 1.7 Hz), 2.36 (s, 3H).

3. 1-Methyl-4-nitro-3-(phenylmethoxy)-2-prop-2-enylbenzene

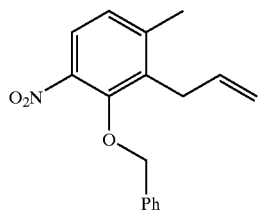

A solution of the product of the preceding step (5.02 g, 26.0 mmol), benzyl bromide (3.40 mL, 28.6 mmol), and cesium carbonate (17.2 g, 52.8 mmol) in DMF (100 mL) was stirred at ambient temperature for 20 hours. The solution was filtered, the filtrate concentrated in vacuo, and the crude product adsorbed onto silica. This was poured onto a short bed of silica and eluted with DCM, and the eluate evaporated to give the title compound (7.20 g, 98%) as a yellow oil. $^1$H NMR (300 MHz, CDCl$_3$) δ 7.72 (d, 1H, J=8.4 Hz), 7.46 (m, 2H), 7.37 (m, 3H), 7.06 (d, 1H, J=8.5 Hz), 5.93 (m, 1H), 5.08 (m, 1H), 4.98 (s, 2H), 4.88 (m, 1H), 3.51 (dt, 2H, J=5.4 Hz, 1.9 Hz), 2.36 (s, 3H).

4. 4-Methyl-2-(phenylmethoxy)-3-prop-2-enylphenylamine

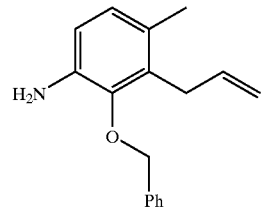

The product of the preceding step (0.55 g, 1.94 mmol) and tin(II) chloride dihydrate (2.89 g, 12.8 mmol) were stirred in reagent grade ethanol (40 mL) at ambient temperature. After 20 hours the reaction was concentrated in vacuo and the residue partitioned between saturated sodium bicarbonate and DCM. The resulting emulsion was filtered, the solids and aqueous layer washed with additional DCM, and the combined organic layers washed with brine, dried over sodium sulfate, and filtered. The filtrate was then evaporated giving the title compound as an orange oil (0.51 g, 90%). $^1$H NMR (300 MHz, CDCl$_3$) δ 7.47 (m, 2H), 7.38 (m, 3H), 6.78 (d, 1H, J=8.1 Hz), 6.60 (d, 1H, J=8.0 Hz), 5.97 (m, 1H), 5.02 (m, 1H), 4.95 (m, 1H), 4.85 (s, 2H), 3.64 (br s, 2H), 3.47 (dt, 2H, J=5.7 Hz, 1.8 Hz), 2.20 (s, 3H).

5. [4-Methyl-2-(phenylmethoxy)-3-prop-2-enylphenyl][(3-methylphenyl)sulfonyl]amine

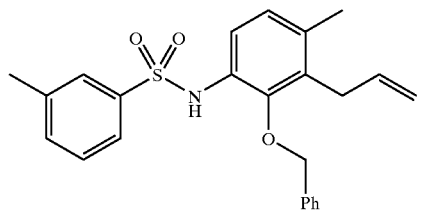

The product of the preceding step (0.49 g, 1.92 mmol) was dissolved in DCM (10 mL) and treated with m-toluenesulfonyl chloride (0.37 g, 1.96 mmol) and N-methylmorpholine (0.25 mL, 2.27 mmol) at ambient temperature. After 18 hours the reaction was concentrated in vacuo and the residue purified by flash column chromatography (DCM eluant) giving the title compound as a pale yellow oil (0.72 g, 92%). $^1$H NMR (300 MHz, CDCl$_3$) δ 7.54 (m, 2H), 7.35 (m, 8H), 6.89 (d, 1H, J=8.3 Hz), 6.80 (s, 1H), 5.87 (m, 1H), 4.99 (m, 1H), 4.79 (m, 1H), 4.43 (s, 2H), 3.36 (dt, 2H, J=5.3 Hz, 1.9 Hz), 2.31 (s, 3H), 2.19 (s, 3H).

6. 2-(6-Methyl-3-{[(3-methylphenyl)sulfonyl]amino}-2-(phenylmethoxy)phenyl)ethanol

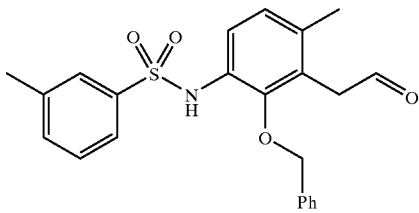

The product of the preceding step (0.71 g, 1.74 mmol) was dissolved in 1,4-dioxane (25 mL) and treated with a solution of sodium periodate (1.50 g, 7.01 mmol) in water (12 mL) and a 2.5 wt % solution of osmium tetraoxide (0.25 mL, 0.02 mmol) in 2-methyl-2-propanol. After stirring 4 hours at ambient temperature the reaction was diluted with DCM, washed with 5% aqueous sodium bisulfite, water, and brine, dried over sodium sulfate, and filtered. The filtrate was concentrated in vacuo giving a pale yellow oil that was used without further purification.

7. 2-(6-Methyl-3-{[(3-methylphenyl)sulfonyl]amino}-2-(phenylmethoxy)phenyl)acetic Acid

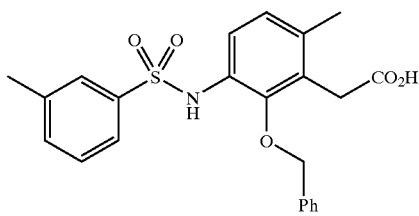

A solution of sodium dichromate (0.79 g, 2.64 mmol) and concentrated sulfuric acid (1.5 mL, 28 mmol) in water (25 ml) was added to a solution of the product of the preceding step in acetone (25 mL), and the reaction stirred at ambient temperature for 3 days. After adding methanol (3 mL) and stirring an additional 15 minutes, the organic solvents were removed in vacuo and the remaining aqueous layer extracted with DCM. The DCM layer was washed with brine, dried over sodium sulfate, filtered, and the filtrate concentrated and purified by flash column chromatography (10% methanol in DCM) giving the title compound as a pale yellow solid (0.51 g, 69% from Step 5). $^1$H NMR (300 MHz, CDCl$_3$) δ 7.56 (m, 2H), 7.39 (m, 4H), 7.31 (m, 4H), 6.93 (d, 1H, J=8.4 Hz), 6.78 (s, 1H), 4.52 (s, 2H), 3.67 (s, 2H), 2.33 (s, 3H), 2.21 (s, 3H). Mass spectrum (LCMS, ESI pos.) calc'd. for C$_{23}$H$_{23}$NO$_5$S: 448.1 (M+Na), 425.1 (M+H). Found: 448.1, 425.9.

8. N-[2-({N,N'-Di-[tert-butoxycarbonyl]}guanidinooxy)ethyl]-2-(6-methyl-3-{[(3-methylphenyl)sulfonyl]amino}-2-(phenylmethoxy)phenyl)acetamide

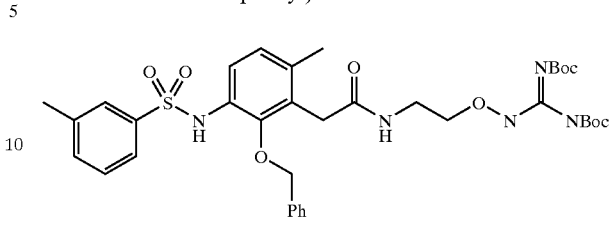

A solution of the product of the preceding step (0.32 g, 0.75 mmol), BOP (0.34 g, 0.77 mmol), triethylamine (0.25 mL, 1.80 mmol), and [N,N'-di(tert-butoxycarbonyl)]-2-aminoethoxyguanidine (Tianbao Lu, et al. WO 99/26926 (1999)) (0.27 g, 0.76 mmol), in DMF (15 mL) was stirred at ambient temperature overnight. The reaction was concentrated in vacuo, the residue dissolved in DCM, washed with saturated sodium bicarbonate, water, and brine, dried over sodium sulfate, and filtered. The filtrate was concentrated in vacuo and the crude product purified by flash column chromatography (7% methanol in DCM eluant) giving the title compound as a pale yellow solid (0.41 g, 76%). $^1$H NMR (300 MHz, CDCl$_3$) δ 9.11 (s, 1H), 7.93 (m, 1H), 7.55 (m, 3H), 7.36 (m, 8H), 6.90 (d, 1H, J=8.3 Hz), 6.84 (s, 1H), 4.60 (s, 2H), 4.06 (m, 2H), 3.71 (s, 2H), 3.56 (dd, 2H, J=8.8 Hz, 5.2 Hz), 2.34 (s, 3H), 2.23 (s, 3H), 1.51 (s, 9H), 1.43 (s, 9H).

9. N-[2-({N,N'-Di-[tert-butoxycarbonyl]}guanidinooxy)ethyl]-2-(2-hydroxy-6-methyl-3-{[(3-methylphenyl)sulfonyl]amino}phenyl)acetamide

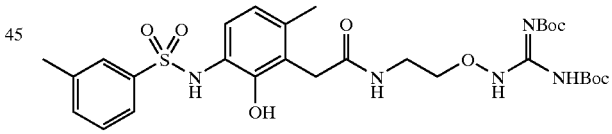

The product of the preceding step (0.41 g, 0.57 mmol) and 10% palladium (0) on carbon (60 mg) were dissolved in reagent grade ethanol (20 mL), degassed with nitrogen and vacuum, and stirred under a hydrogen balloon at ambient temperature for 4 hours. The reaction was filtered over Celite, the frit washed with methanol, the filtrate evaporated, and the residue purified by preparative thin-layer chromatography (5% methanol in DCM eluant) giving the title compound as pale yellow solid (13.0 mg, 4%). $^1$H NMR (300 MHz, CDCl$_3$) δ 9.25 (s, [H]), 8.62 (m, 1H), 7.61 (m, 3H), 7.29 (m, 3H), 6.61 (d, 1H, J=8.5 Hz), 4.06 (m, 2H), 3.64 (s, 2H), 3.54 (dd, 2H, J=8.7 Hz, 5.0 Hz), 2.34 (s, 3H), 2.30 (s, 3H), 1.51 (s, 9H), 1.49 (s, 9H).

10. N-[2-(Guanidinooxy)ethyl]-2-(2-hydroxy-6-methyl-3-{[(3-methylphenyl)sulfonyl]amino}phenyl)acetamide Hydrochloride Salt

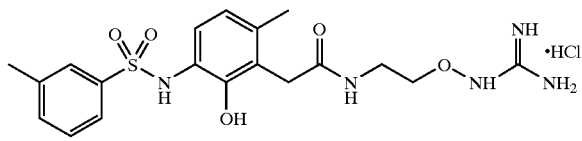

The product of the preceding step (13.0 mg, 0.02 mmol) was dissolved in DCM (5 mL) and treated with trifluoroacetic acid (1 mL) at ambient temperature. After 16 hours the reaction was concentrated in vacuo and the crude product purified by preparative thin-layer chromatography (12% methanol in DCM eluant, saturated with ammonia). The resulting product was treated with 4N HCl in ethanol, filtered, the filtrate evaporated, and the solid washed with diethyl ether and vacuum-dried giving the title compound (5.0 mg, 52%) as a tan solid. $^1$H NMR (300 MHz, CD$_3$OD) δ 7.51 (m, 2H), 7.38 (m, 2H), 6.56 (m, 2H), 3.91 (t, 2H, J=5.3 Hz), 3.61 (s, 2H), 3.47 (t, 2H, J=5.3 Hz), 2.36 (s, 3H), 2.27 (s, 3H). Mass spectrum (LCMS, ESI pos.) calc'd. for C$_{19}$H$_{25}$N$_5$O$_5$S: 436.1 (M+H). Found: 436.2.

Example 10

N-[(6-Amino-2-methyl(3-pyridyl))methyl]-2-(2-hydroxy-6-methyl-3-{[(3-methylphenyl)sulfonyl]amino}phenyl)acetamide Hydrochloride Salt

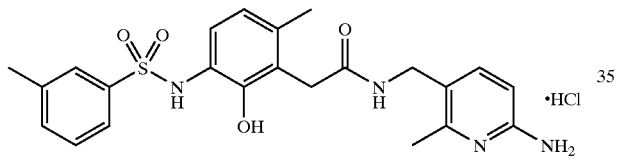

1. N-[(6-Amino-2-methyl(3-pyridyl))methyl]-2-(6-methyl-3-{[(3-methylphenyl)sulfonyl]amino}-2-(phenylmethoxy)phenyl)acetamide

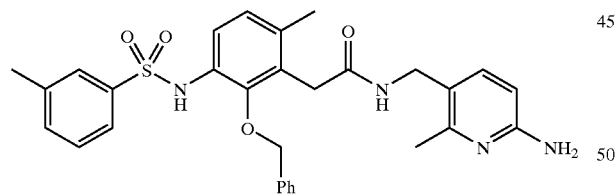

The product of Example 9, step 7 (0.18 g, 0.42 mmol), BOP (0.21 g, 0.47 mmol), triethylamine (0.25 mL, 1.80 mmol), and 2-amino-5-aminomethyl-6-methylpyridine dihydrochloride (Sanderson, P. E., et al. WO 97/01338 (1997)) (0.10 g, 0.48 mmol), were dissolved in DMF (10 mL) and stirred at ambient temperature for 2 hours. The reaction was concentrated in vacuo and the crude product purified by flash column chromatography (gradient elution: 10% to 15% methanol in DCM) giving an impure product that was dissolved in DCM, washed with saturated sodium bicarbonate, water, and brine, dried over sodium sulfate, and filtered. The evaporated filtrate then gave the title compound as a pale yellow solid (0.23 g, 99%). $^1$H NMR (300 MHz, CDCl$_3$) δ 7.64 (m, 1H), 7.56 (m, 1H), 7.35 (m, 10H), 7.11 (d, 1H, J=8.3 Hz), 6.94 (d, 1H, J=8.5 Hz), 6.22 (d, 1H, J=8.1 Hz), 5.60 (br t, 1H, J=5.3 Hz), 4.49 (s, 2H), 4.37 (br s, 2H), 4.19 (d, 2H, J=5.5 Hz), 3.56 (s, 2H), 2.34 (s, 3H), 2.23 (s, 3H), 2.22 (s, 3H). Mass spectrum (LCMS, ESI pos.) calc'd. for C$_{30}$H$_{32}$N$_4$O$_4$S: 545.2 (M+H). Found: 545.2.

2. N-[(6-Amino-2-methyl(3-pyridyl))methyl]-2-(2-hydroxy-6-methyl-3-{[(3-methylphenyl)sulfonyl]amino}phenyl)acetamide Hydrochloride Salt

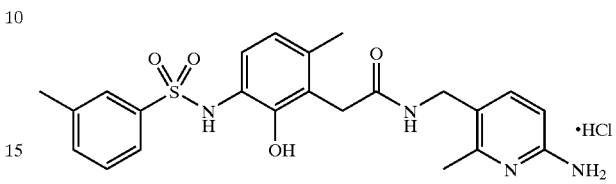

The product of the preceding step (0.22 g, 0.41 mmol) and 10% palladium (0) on carbon (0.03 g) were dissolved in 2:1 ethanol:THF (30 mL), degassed with nitrogen and vacuum, and stirred under a hydrogen balloon at ambient temperature. After 7 hours the reaction was filtered over Celite, the frit washed with methanol, and the filtrate concentrated in vacuo. The residue was treated with 4N HCl in ethanol (ca. 3 mL), evaporated under high vacuum, dissolved in DCM, filtered, and the filtrate evaporated under high vacuum again giving the title compound (0.14 g, 71%) as a pale beige solid. $^1$H NMR (300 MHz, CDCl$_3$/CD$_3$OD) δ 7.60 (m, 3H), 7.33 (m, 2H), 6.82 (d, 1H, J=8.2 Hz), 6.67 (d, 1H, J=9.0 Hz), 6.58 (d, 1H, J=8.3 Hz), 4.18 (s, 2H), 3.58 (s, 2H), 2.45 (s, 3H), 2.37 (s, 3H), 2.25 (s, 3H). Mass spectrum (LCMS, ESI pos.) calc'd. for C$_{23}$H$_{26}$N$_4$O$_4$S: 455.2 (M+H). Found: 455.2.

Example 11

3-({N-[2-(Guanidinooxy)ethyl]carbamoyl}methyl)-2-hydroxy-4-methylphenyl 3-methylbenzenesulfonate Hydrochloride Salt

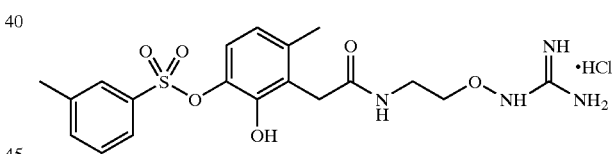

1. 2-Methoxy-4-methylphenyl 3-methylbenzenesulfonate

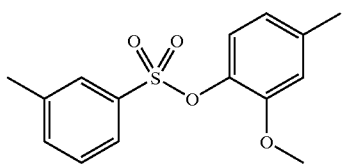

A solution of m-toluenesulfonyl chloride (0.53 g, 2.78 mmol) and 2-methoxy-4-methylphenol (0.38 g, 2.75 mmol) in DCM (10 mL) was treated with triethylamine (0.5 mL, 3.6 mmol) and stirred at ambient temperature. After 18 hours the reaction was concentrated in vacuo, the residue dissolved in 1:1 hexane:DCM, filtered, and the filtrate evaporated under high vacuum giving the title compound as a white solid (0.79 g, 99%). $^1$H NMR (300 MHz, CDCl$_3$) δ 7.72 (br s, 1H), 7.66 (br d, 1H, J=7.2 Hz), 7.45 (br d, 1H, J=7.2 Hz), 7.38 (t, 1H, J=7.6 Hz), 7.00 (d, 1H, J=8.1 Hz), 6.67 (m, 1H), 3.54 (s, 3H), 2.42 (s, 3H), 2.31 (s, 3).

2. 2-Hydroxy-4-methylphenyl 3-methylbenzenesulfonate

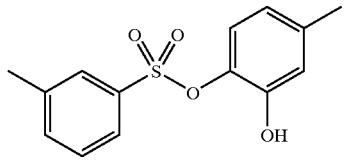

The product of the preceding step (0.79 g, 2.72 mmol) was dissolved in DCM (10 mL), cooled to −78° C., and treated with 1N boron tribromide in DCM (3.0 mL) under nitrogen. After 10 min the dry ice bath was removed, and the reaction stirred another hour while warming to ambient temperature. After slowly quenching with water, the reaction was diluted with additional DCM, washed with brine, dried over sodium sulfate, and filtered. The filtrate was concentrated in vacuo and the residue purified by flash column chromatography (gradient elution: 50% to 33% to 0% hexane in DCM) giving the title compound as a white crystalline solid (0.51 g, 68%). $^1$H NMR (300 MHz, CDCl$_3$) δ 7.71 (br s, 1H), 7.67 (br d, 1H, J=7.7 Hz), 7.51 (br d, 1H, J=8.1 Hz), 7.43 (t, 1H, J=7.7 Hz), 6.81 (d, 1H J=1.71 Hz), 6.63 (d, 1H, J=8.3 Hz), 6.55 (m, 1H), 5.87 (s, 1H), 2.43 (s, 3H), 2.26 (s, 3H).

3. 4-Methyl-2-prop-2-enyloxyphenyl 3-methylbenzenesulfonate

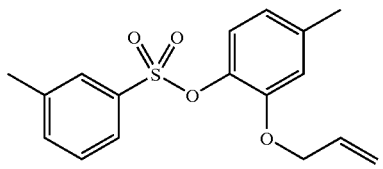

A solution of the product of the preceding step (0.51 g, 1.83 mmol), allyl bromide (0.20 mL, 2.30 mmol), and cesium carbonate (0.77 g, 2.40 mmol) in DMF (25 mL) was stirred for 16 hours at ambient temperature. The reaction was concentrated in vacuo, the residue dissolved in DCM, filtered, and the filtrate washed with 1N aqueous KOH, water, and brine, dried over sodium sulfate, and filtered. The evaporated filtrate then gave the title compound as a pale yellow oil (0.54 g, 93%). $^1$H NMR (400 MHz, CDCl$_3$) δ 7.72 (s, 1H), 7.64 (d, 1H, J=7.7 Hz), 7.42 (d, 1H, J=7.7 Hz), 7.35 (t, 1H, J=7.7 Hz), 7.04 (d, 1H, J=8.2 Hz), 6.68 (m, 2H), 5.80 (ddt, 1H, J=17.3 Hz, 10.6 Hz, 5.1 Hz), 5.28 (ddd, 1H, J=17.3 Hz, 3.1 Hz, 1.6 Hz), 5.20 (ddd, 1H, J=10.6 Hz, 2.8 Hz, 1.3 Hz), 4.29 (dt, 2H, J=5.1 Hz, 1.5 Hz), 2.40 (s, 3H), 2.30 (s, 3H).

4. 2-Hydroxy-4-methyl-3-prop-2-enylphenyl 3-methylbenzenesulfonate

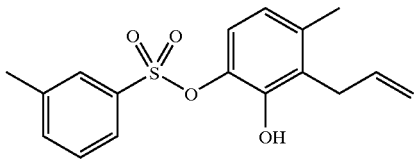

The product of the preceding step (0.54 g, 1.70 mmol) was heated neat at 200° C. for 6 hrs, cooled to ambient temperature, and purified twice by flash column chromatography (first with 2:1 DCM:hexane, then with 4:1 hexane:ethyl acetate eluant) giving the title compound as a colorless oil (84 mg, 16%). $^1$H NR (400 MHz, CDCl$_3$) δ 7.74 (s, 1H), 7.67 (d, 1H, J=7.8 Hz), 7.44 (d, 1H, J=7.6 Hz), 7.36 (t, 1H, J=7.7 Hz), 6.86 (d, 1H, J=8.3 Hz), 6.55 (d, 1H, J=8.3 Hz), 4.74 (m, 1H), 3.15 (dd, 1H, J=15.5 Hz, 8.9 Hz), 2.61 (dd, 1H, J=15.5 Hz, 7.6 Hz), 2.41 (s, 3H), 2.16 (s, 3H), 1.24 (d, 2H, J=6.3 Hz).

5. 4-Methyl-2-(phenylmethoxy)-3-prop-2-enylphenyl 3-methylbenzenesulfonate

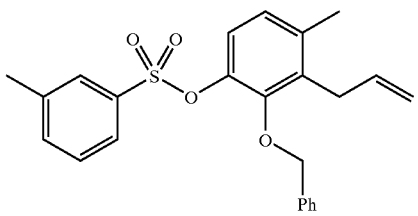

The product of the preceding step (68 mg, 0.21 mmol) and cesium carbonate (0.19 g, 0.58 mmol) were dissolved in DMF (5 mL) and treated with benzyl bromide (0.05 mL, 0.42 mmol) at ambient temperature. After 3 days the reaction was concentrated in vacuo and the residue purified by flash column chromatography (DCM eluant) giving the title compound as a pale yellow oil (50 mg, 58%). $^1$HNMR (400 MHz, CDCl$_3$)δ 7.60 (br s, 1H), 7.54 (br d, 1H, J=7.8 Hz), 7.34 (m, 4H), 7.27 (m, 3H), 7.10 (d, 1H, J=8.4 Hz), 6.91 (d, 1H, J=8.4 Hz), 5.74 (ddt, 1H, J=17.1 Hz, 10.2 Hz, 5.7 Hz), 4.93 (dq, 1H, J=10.2 Hz, 1.7 Hz), 4.81 (s, 2H), 4.72 (dq, 1H, J=17.1 Hz, 1.8 Hz), 3.30 (dt, 2H, J=5.7 Hz, 1.7 Hz), 2.24 (s, 3H), 2.23 (s, 3H).

6. 4-Methyl-3-(2-oxoethyl)-2-(phenylmethoxy)phenyl-3-methylbenzenesulfonate

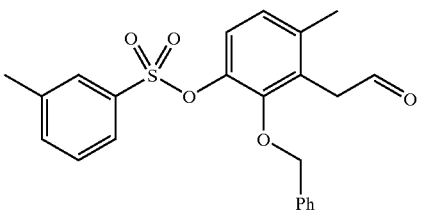

To a solution of the product of the preceding step (50 mg, 0.12 mmol) and sodium periodate (0.12 g, 0.56 mmol) in 5:1 acetonitrile water (12 mL) was added ruthenium(III) chloride hydrate (8 mg, 0.04 mmol). The reaction was stirred 6 hours at ambient temperature, diluted with DCM, and washed with 5% aqueous sodium bisulfite, water and brine. The organic solution was dried over sodium sulfate, filtered, and the filtrate evaporated giving the title compound as a crude oil that was used without further purification.

7. 2-{6-Methyl-3-[(3-methylphenyl)sulfonyloxy]-2-(phenylmethoxy)phenyl]acetic Acid

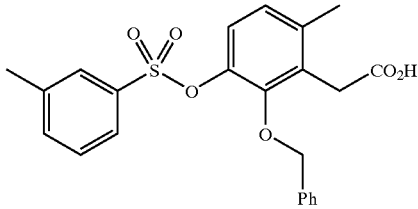

The product of the preceding step was dissolved in acetone (5 mL) and treated with a solution of sodium dichromate (65 mg, 0.22 mmol) and concentrated sulfuric acid (1 mL) in water (4 mL) at ambient temperature. After stirring 3 days the acetone was removed in vacuo, and the remaining aqueous layer extracted with DCM. The organic phase was then washed with brine, dried over sodium sulfate, filtered, and the evaporated filtrate purified by flash column chromatography (8% methanol in DCM eluant) giving the title compound (45 mg, 88% from step 5) as a white solid. $^1$H NMR (400 MHz, CDCl$_3$) δ 7.61 (br s, 1H), 7.53 (br d, 1H, J=7.8 Hz), 7.33 (br d, 1H, J=7.6 Hz), 7.27 (m, 6H), 7.12 (d, 1H, J=8.4 Hz), 6.92 (d, 1H, J=8.4 Hz), 4.87 (s, 2H), 3.60 (s, 2H), 2.24 (s, 3H), 2.23 (s, 3H).

8. 3-({N-[2-({N,N'-Di-[tert-butoxycarbonyl]}guanidinooxy)ethyl]carbamoyl}methyl)-4-methyl-2-(phenylmethoxy)phenyl 3-methylbenzenesulfonate

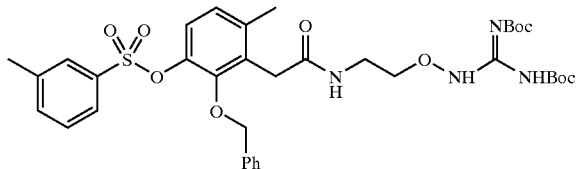

To a solution of the product of the preceding step (45 mg, 0.11 mmol), BOP (48 mg, 0.11 mmol), and [N,N'-di(tert-butoxycarbonyl)]-2-aminoethoxyguanidine (Tianbao Lu, et al., WO 99/26926 (1999)) (39 mg, 0.11 mmol), in DMF (5 mL) was added triethylamine (0.2 mL, 1.4 mmol). After stirring 18 hours at ambient temperature, the reaction was concentrated in vacuo and the residue purified by flash column chromatography (3:1 DCM:ethyl acetate eluant) giving the title compound as a colorless oil (61 mg, 79%). $^1$H NMR (300 MHz, CDCl$_3$) δ 9.11 (s, 1H), 7.65 (br s, 1H), 7.58 (br d, 1H, J=8.5 Hz), 7.48 (m, 1H), 7.36 (br d, 1H, J=7.6 Hz), 7.29 (m, 7H), 7.03 (d, 1H, J=8.4 Hz), 6.90 (d, 1H, J=8.5 Hz), 4.92 (s, 2H), 4.02 (m, 2H), 3.66 (s, 2H), 3.50 (dd, 2H, J=9.2 Hz, 5.2 Hz), 2.28 (s, 3H), 2.26 (s, 3H), 1.51 (s, 9H), 1.45 (s, 9H).

9. 3-({N-[2-({N,N'-Di-[tert-butoxycarbonyl]}guanidinooxy)ethyl]carbamoyl}methyl)-2-hydroxy-4-methylphenyl 3-methylbenzenesulfonate

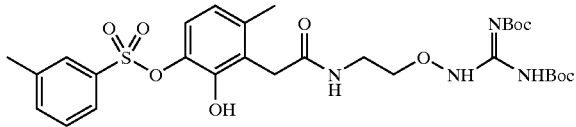

The product of the preceding step (61 mg, 0.08 mmol) and 10% palladium (o) on carbon (20 mg) were dissolved in a 1:1:1 mixture of THF, methanol, and water (50 mL), degassed with nitrogen and vacuum, and stirred vigorously under a hydrogen balloon at ambient temperature. After 18 hours the reaction was filtered over Celite, the frit washed with methanol, and the evaporated filtrate purified by flash column chromatography (10% ethyl acetate in DCM eluant) giving the title compound as a colorless solid (40 mg, 74%). $^1$H NMR (400 MHz, CDCl$_3$) δ 9.25 (s, 1H), 8.50 (br t, 1H, J=4.9 Hz), 7.79 (s, 1H), 7.57 (d, 1H, J=7.7 Hz), 7.59 (br s, 1H), 7.43 (d, 1H, J=7.7 Hz), 7.38 (t, 1H, J=7.6 Hz), 6.90 (d, 1H, J=8.3 Hz), 6.62 (d, 1H, J=8.4 Hz), 4.08 (m, 2H), 3.69 (s, 2H), 3.56 (dd, 2H, J=8.7 Hz, 5.0 Hz), 2.41 (s, 3H), 2.35 (s, 3H), 1.51 (s, 9H), 1.50 (s, 9H).

10. 3-({N-[2-(Guanidinooxy)ethyl]carbamoyl}methyl)-2-hydroxy-4-methylphenyl 3-methylbenzenesulfonate Hydrochloride Salt

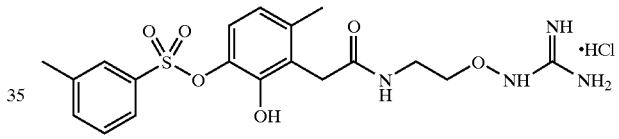

The product of the preceding step (40 mg, 0.06 mmol) was dissolved in DCM (4 mL) and treated with neat trifluoroacetic acid (1.5 mL) at ambient temperature. After 3 hours the reaction was concentrated in vacuo and the residue purified by preparative thin-layer chromatography (20% methanol in DCM saturated with ammonia gas as eluant), treated with 4N HCl in ethanol, and filtered. The evaporated filtrate was washed with diethyl ether and dried under high vacuum giving the title compound as a pale yellow solid (17 mg, 57%). $^1$H NMR (400 MHz, DMSO-d$_6$) δ 10.87 (s, 1H), 9.76 (s, 1H), 7.67 (m, 5), 7.60 (d, 1H, J=7.6 Hz), 7.51 (t, 1H, J=7.7 Hz), 6.70 (d, 1H, J=8.3 Hz), 6.60 (d, 1H, J=8.5 Hz), 3.79 (t, 2H, J=5.5 Hz), 3.45 (m, 4H), 2.39 (s, 3H), 2.17 (s, 3H). Mass spectrum (LCMS, ESI pos.) calcd. for C$_{19}$H$_{24}$N$_4$O$_6$S: 437.1 (M+H). Found: 437.3.

Example 12

Tablet Preparation

Tablets containing 25.0, 50.0, and 100.0 mg, respectively, of the following active compounds are prepared as illustrated below:

a. N-[2-(Amidinoaminooxy)ethyl]-2-{3-[(2,2-difluoro-2-phenylethyl)amino]-6-chloro-2-fluorophenyl}acetamide trifluoroacetate salt; and b. N-[(6-Amino-2-methyl(3-pyridyl))methyl]-2-{3-[(2,2-difluoro-2-phenylethyl)amino]-6-chloro-2-fluorophenyl}acetamide hydrochloride salt.

TABLE FOR DOSES CONTAINING FROM
25-100 MG OF THE ACTIVE COMPOUND

| | Amount-mg | | |
|---|---|---|---|
| Active Compound | 25.0 | 50.0 | 100.00 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

Example 13

Intravenous Solution Preparation

An intravenous dosage form of the above-indicated active compounds of Examples 1 and 2 is prepared as follows:

| Active Compound | 0.5–10.0 mg |
|---|---|
| Sodium Citrate | 5–50 mg |
| Citric Acid | 1–15 mg |
| Sodium Chloride | 1–8 mg |
| Water for Injection (USP) | q.s. to 1 ml |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md. (1994).

Example 14

In vitro Inhibition of Purified Enzymes

Reagents: All buffer salts were obtained from Sigma Chemical Company (St. Louis, Mo.), and were of the highest purity available. The enzyme substrates, N-benzoyl-Phe-Val-Arg-p-nitroanilide (Sigma B7632), N-benzoyl-Ile-Glu-Gly-Arg-p-nitroanilide hydrochloride (Sigma B2291), N-p-Tosyl-Gly-Pro-Lys-p-nitroanilide (Sigma T6140), N-succinyl-Ala-Ala-Pro-Phe-p-nitroanilide (Sigma S7388) and N-CBZ-Val-Gly-Arg-p-nitroanilide (Sigma C7271) were obtained from Sigma. N-succinyl-Ala-Ala-Pro-Arg-p-nitroanilide (BACHEM L-1720) and N-succinyl-Ala-Ala-Pro-Val-p-nitroanilide (BACHEM L-1770) were obtained from BACHEM (King of Prussia, Pa.).

Human α-thrombin, human factor Xa and human plasmin were obtained from Enzyme Research Laboratories (South Bend, Ind.). Bovine α-chymotrypsin (Sigma C4129), bovine trypsin (Sigma T8642) and human kidney cell urokinase (Sigma U5004) were obtained from Sigma. Human leukocyte elastase was obtained from Elastin Products (Pacific, Mo.).

$K_i$ Determinations: All assays are based on the ability of the test compound to inhibit the enzyme catalyzed hydrolysis of a peptide p-nitroanilide substrate. In a typical $K_i$ determination, substrate is prepared in DMSO, and diluted into an assay buffer consisting of 50 mM HEPES, 200 mM NaCl, pH 7.5. The final concentrations for each of the substrates is listed below. In general, substrate concentrations are lower than the experimentally determined value for $K_m$. Test compounds are prepared as a 1.0 mg/ml solution in DMSO. Dilutions are prepared in DMSO yielding 8 final concentrations encompassing a 200 fold concentration range. Enzyme solutions are prepared at the concentrations listed below in assay buffer.

In a typical $K_i$ determination, into each well of a 96 well plate is pipetted 280 mL of substrate solution, 10 mL of test compound solution, and the plate allowed to thermally equilibrate at 37° C. in a Molecular Devices plate reader for >15 minutes. Reactions were initiated by the addition of a 10 mL aliquot of enzyme and the absorbance increase at 405 nm is recorded for 15 minutes. Data corresponding to less than 10% of the total substrate hydrolysis were used in the calculations. The ratio of the velocity (rate of change in absorbance as a function of time) for a sample containing no test compound is divided by the velocity of a sample containing test compound, and is plotted as a function of test compound concentration. The data are fit to a linear regression, and the value of the slope of the line calculated. The inverse of the slope is the experimentally determined $K_i$ value.

Thrombin: Thrombin activity was assessed as the ability to hydrolyze the substrate N-succinyl-Ala-Ala-Pro-Arg-p-nitroanilide. Substrate solutions were prepared at a concentration of 32 mM (32 mM<<Km=180 mM) in assay buffer. Final DMSO concentration was 4.3%. Purified human α-thrombin was diluted into assay buffer to a concentration of 15 nM. Final reagent concentrations were: [thrombin]= 0.5 nM, [substrate N-succinyl-Ala-Ala-Pro-Arg-p-nitroanilide]=32 nM.

Factor X [FXa]: FXa activity was assessed as the ability to hydrolyze the substrate N-benzoyl-Ile-Glu-Gly-Arg-p-nitroanilide hydrochloride. Substrate solutions were prepared at a concentration of 51 mM (51<<$K_m$=1.3 mM) in assay buffer. Final DMSO concentration was 4.3%. Purified activated human Factor X was diluted into assay buffer to a concentration of 300 nM. Final reagent concentrations were: [FXa] 10 nM, [N-benzoyl-Ile-Glu-Gly-Arg-p-nitroanilide hydrochloride]=51 mM.

Plasmin: Plasmin activity was assessed as the ability to hydrolyze the N-p-Tosyl-Gly-Pro-Lys-p-nitroanilide. Substrate solutions were prepared at a concentration of 37 mM (37 mM<<$K_m$=243 mM) in assay buffer. Final DMSO concentration was 4.3%. Purified human plasmin was diluted into assay buffer to a concentration of 240 nM. Final reagent concentrations were: [Plasmin]=8 nM, [N-p-Tosyl-Gly-Pro-Lys-p-nitroanilide]=37 mM.

Chymotrypsin: Chymotrypsin activity was assessed as the ability to hydrolyze N-succinyl-Ala-Ala-Pro-Phe-p-nitroanilide. Substrate solutions were prepared at a concentration of 14 mM (14 mM<<$K_m$=62 mM) in assay buffer. Final DMSO concentration was 4.3%. Purified bovine chymotrypsin was diluted into assay buffer to a concentration of 81 nM. Final reagent concentrations were: [Chymotrypsin]= 2.7 nM, [N-succinyl-Ala-Ala-Pro-Phe-p-nitroanilide]=14 mM.

Trypsin: Trypsin activity was assessed as the ability to hydrolyze N-benzoyl-Phe-Val-Arg-p-nitroanilide. Substrate solutions were prepared at a concentration of 13 mM (13 mM<<$K_m$=291 mM) in assay buffer. Final DMSO concentration was 4.3%. Purified bovine trypsin was diluted into assay buffer to a concentration of 120 nM. Final reagent concentrations were: [Trypsin]=4 nM, (N-benzoyl-Phe-Val-Arg-p-nitroanilide]=13 mM.

Elastase: Elastase activity was assessed as the ability to hydrolyze N-succinyl-Ala-Ala-Pro-Val-p-nitroanilide. Substrate solutions were prepared at a concentration of 19 mM (19 mM<<$K_m$=89 mM) in assay buffer. Final DMSO concentration was 4.3%. Purified human leukocyte elastase was diluted into assay buffer to a concentration of 750 nM. Final reagent concentrations were: [Elastase]=25 nM, [N-succinyl-Ala-Ala-Pro-Val-p-nitroanilide]=19 mM.

Urokinase: Urokinase activity was assessed as the ability to hydrolyze N-CBZ-Val-Gly-Arg-p-nitroanilide. Substrate solutions were prepared at a concentration of 100 mM (100 mM<$K_m$=1.2 mM) in assay buffer. Final DMSO concentration was 4.3%. Purified human kidney urokinase was diluted into assay buffer to a concentration of 1.2 mM. Final reagent concentrations were: [Urokinase]=40 nM, and [N-CBZ-Val-Gly-Arg-p-nitroanilide]=100 mM.

The results indicate that the compounds of Examples 1 through 11 have Ki values for human thrombin of between 0.0028 and 20 $\mu$M. The compound of Example 5 has a Ki of 0.0028 $\mu$M.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound of Formula I:

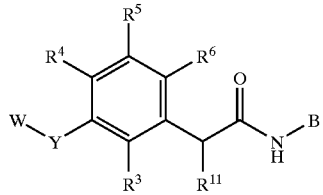

or a solvate, hydrate or pharmaceutically acceptable salt thereof; wherein:

W is hydrogen, $R^1$, $R^1OC(O)$, $R^1C(O)$, $R^1(CH_2)_sNHC(O)$, $R^1S(O)_2$, or $(R^1)_2CH(CH_2)_sNHC(O)$, wherein s is 0–4;

$R^1$ is
$R^2$,
$R^2(CH_2)_tC(R^{12})_2$, where t is 0–3, and each $R^{12}$ can be the same or different,
$(R^2)(OR^{12})CH(CH_2)_p$, where p is 1–4,
$(R^2)_2(OR^{12})C(CH_2)_p$, where p is 1–4,
$R^2C(R^{12})_2(CH_2)_t$, wherein t is 0–3, and each $R^{12}$ can be the same or different, wherein $(R^{12})_2$ can also form a ring with C represented by $C_{3-9}$ cycloalkyl,
$R^2CF_2C(R^{12})_2(CH_2)_q$, wherein q is 0–2, and each $R^{12}$ can be the same or different, wherein $(R^{12})_2$ can also form a ring with C represented by $C_{3-9}$ cycloalkyl,
$R^2CH_2C(R^{12})_2(CH_2)_q$, wherein q is 0–2, and each $R^{12}$ can be the same or different, wherein $(R^{12})_2$ can also form a ring with C represented by $C_{3-9}$ cycloalkyl,
$(R^2)_2CH(CH_2)_r$, where r is 0–4 and each $R^2$ can be the same or different, and wherein $(R^2)_2$ can also form a ring with CH represented by $C_{3-9}$ cycloalkyl, $C_{7-12}$ bicylic alkyl, $C_{10-16}$ tricyclic alkyl, or a 5- to 7-membered mono- or bicyclic heterocyclic ring which can be saturated or unsaturated, and which contains from one to three heteroatoms selected from the group consisting of N, O and S, $R^2O(CH_2)_p$, wherein p is 2–4,
$(R^2)_2CF(CH_2)_r$, wherein r is 0–4 and each $R^2$ can be the same different, wherein $(R^2)_2$ can also form a ring with C represented by $C_{3-9}$ cycloalkyl, $C_{7-12}$ bicyclic alkyl, $C_{10-16}$ tricyclic alkyl, or a 5- to 7-membered mono- or bicyclic heterocyclic ring which can be saturated or unsaturated, and which contains from one to three heteroatoms selected from the group consisting of N, O and S,

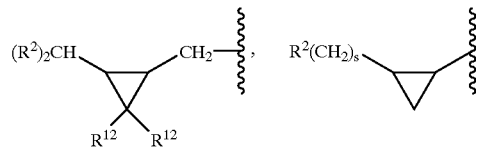

where s is 0 or 1, or
$R^2CF_2C(R^{12})_2$;

$R^2$ is
phenyl, naphthyl, or biphenyl, each of which is unsubstituted or substituted with one or more of $C_{1-4}$ alkyl, $C_{1-4}$ alkoxy, halogen, hydroxy, $CF_3$, $OCF_3$, COOH, $CONH_2$, or $SO_2NH_2$,
a 5- to 7-membered mono- or a 9- to 10-membered bicyclic heterocyclic ring or non-heterocyclic ring which can be saturated or unsaturated, wherein the heterocyclic ring contains from one to four heteroatoms selected from the group consisting of N, O and S, and wherein the heterocyclic or non-heterocyclic ring is unsubstituted or substituted with halogen or hydroxy,
$C_{1-12}$ alky, unsubstituted or substituted with one or more of hydroxy, COOH, amino, optionally $C_{1-3}$ alkyl, substituted aryl, $C_{3-9}$ cycloalkyl, $CF_3$, $N(CH_3)_2$, heteroaryl, or heterocycloalkyl,
$CF_3$,
$C_{3-9}$ cycloalkyl, unsubstituted or substituted with aryl,
$C_{7-12}$ bicyclic alkyl, or
$C_{10-16}$ tricyclic alkyl;

Y is —NH— or —O—;

$R^3$, $R^4$, $R^5$ and $R^6$ are independently hydrogen, alkyl, cycloalkyl, alkenyl, alkynyl, optionally substituted aryl, optionally substituted aralkyl, optionally substituted heteroaryl, haloalkyl, hydroxy, alkoxy, aryloxy, heteroaryloxy, halogen, haloalkoxy, hydroxyalkyl, cyano, nitro, —$CO_2R^x$, —$CH_2OR^x$ or —$OR^x$,
where $R^x$, in each instance, is independently one of hydrogen, $C_{1-12}$ alkyl or $C_{3-9}$ cycloalkyl wherein said $C_{-12}$ alkyl or $C_{3-9}$ cycloalkyl groups may optionally have one or more unsaturations;

$R^{11}$ is hydrogen, alkyl, or alkenyl;

$R^{12}$ is
hydrogen or halogen,
phenyl, naphthyl, or biphenyl, each of which is unsubstituted or substituted with one or more of $C_{1-4}$ alkyl, $C_{1-4}$ alkoxy, halogen, hydroxy, $CF_3$, $OCF_3$, COOH, or $CONH_2$,
a 5- to 7-membered mono- or a 9- to 10-membered bicyclic heterocyclic ring which can be saturated or unsaturated, and which contains from one to four heteroatoms selected from the group consisting of N, O and S, $C_{1-12}$ alkyl, unsubstituted or substituted with one or more of hydroxy, COOH, amino, $C_{6-14}$ aryl, heteroaryl, or heterocycloalkyl,
$CF_3$,
$C_{3-9}$ cycloalkyl,
$C_{7-12}$ bicyclic alkyl, or
$C_{10-16}$ tricyclic alkyl;

B is:

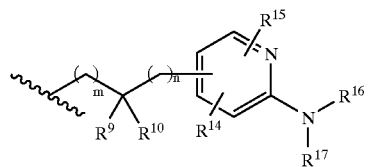

wherein
$R^9$ and $R^{10}$ are independently hydrogen, alkyl, aralkyl, aryl, hydroxyalkyl, aminoalkyl, monoalkylaminoalkyl, dialkylaminoalkyl or carboxyalkyl or $R^9$ and $R^{10}$ are taken together to form $-(CH_2)_v-$, where v is 2 to 7, preferably 2 to 5;
n is from zero to 8; and
m is from zero to 6;
$R^{14}$ and $R^{15}$ are independently hydrogen, alkyl, cycloalkyl, halogen or alkoxy; and
$R^{16}$ and $R^{17}$ are independently hydrogen, alkyl, hydroxy, alkoxy, aryloxy, alkoxycarbonyl, cyano or $-CO_2R^j$, where $R^j$ is $C_{1-12}$ alkyl, $C_{3-9}$ cycloalkyl, $C_{6-14}$ aryl, $C_{6-14}ar(C_{1-2})$alkyl, halo$(C_{1-12})$alkyl or

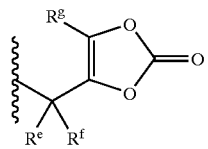

where $R^e$, $R^f$ and $R^g$ are independently hydrogen or $C_{1-12}$ alkyl.

2. A compound of claim 1, wherein
$R^3$, $R^4$, $R^5$ and $R^6$ are independently hydrogen, $C_{1-12}$ alkyl, $C_{3-9}$ cycloalkyl, halogen, $C_{2-20}$ alkenyl, $C_{2-20}$ alkynyl, optionally substituted $C_{6-14}$ aryl, optionally substituted $C_{6-14}ar(C_{1-12})$alkyl, optionally substituted heteroaryl, halo$(C_{1-12})$alkyl, $C_{1-12}$ alkoxy, $C_{6-14}$ aryloxy, heteroaryloxy, halo$(C_{1-20})$alkoxy or hydroxy$(C_{1-12})$alkyl;
$R^{11}$ is hydrogen, $C_{1-12}$ alkyl or $C_{2-20}$ alkenyl;
$R^9$ and $R^{10}$ are independently hydrogen, $C_{1-12}$ alkyl, $C_{6-14}ar(C_{1-2})$alkyl, $C_{6-14}$ aryl, hydroxy$(C_{1-12})$alkyl, amino$(C_{1-12})$alkyl, mono$(C_{1-2})$alkylamino$(C_{1-12})$alkyl, di$(C_{1-12})$alkylamino$(C_{1-12})$alkyl, or carboxy$(C_{1-2})$alkyl;
$R^{14}$ and $R^{15}$ are independently $C_{1-2}$ alkyl, $C_{3-9}$ cycloalkyl or $C_{1-20}$ alkoxy; and
$R^{16}$ and $R^{17}$ are independently $C_{1-12}$ alkyl, $C_{1-20}$ alkoxy, $C_{6-14}$ aryloxy or $C_{1-20}$ alkoxycarbonyl.

3. A compound according to claim 1, wherein Y is $-NH-$.

4. A compound according to claim 1, wherein W is $R^1$ or $R^1S(O)_2$, where $R^1$ is $R^2$ and $R^2$ is either optionally substituted phenyl, naphthyl, biphenyl or $C_{1-7}$ alkyl substituted with aryl, wherein the optional substituents on said optionally substituted phenyl, naphthyl, and biphenyl are selected from the group consisting of one or more of $C_{1-4}$ alkyl, $C_{1-4}$ alkoxy, halogen, hydroxy, $CF_3$, $OCF_3$, COOH, $CONH_2$, or $SO_2NH_2$.

5. A compound according to claim 1, wherein W is $R^1$, where $R^1$ is $R^2$ or $R^2CF_2C(R^{12})_2(CH_2)_q$, and $R^2$ is either optionally substituted aryl or $C_{1-7}$ alkyl substituted with aryl; $R^{12}$ is hydrogen; and q is zero.

6. A compound according to claim 1, wherein $R^6$ is $C_{1-6}$ alkyl or halogen.

7. A compound according to claim 6, wherein $R^6$ is methyl, chloro or fluoro.

8. A compound according to claim 7, wherein $R^6$ is chloro while $R^3$ is fluoro or hydroxy.

9. A compound according to claim 1, wherein $R^{11}$ is hydrogen.

10. A compound according to claim 1, wherein each of $R^9$ and $R^{10}$ are hydrogen.

11. A compound of claim 1, which is one of:
N-[(6-Amino-2-methyl(3-pyridyl))methyl]-2-{3-[(2,2-difluoro-2-phenylethyl)amino]-6-chloro-2-fluorophenyl}acetamide;
N-[(6-Amino-2,4-dimethyl(3-pyridyl))methyl]-2-{3-[(2,2-difluoro-2-phenylethyl)amino]-6-chloro-2-fluorophenyl}acetamide
N-[(6-Amino-2-methyl(3-pyridyl))methyl]-2-(3-{[2,2-difluoro-2-(4-fluoronaphthyl)ethyl]amino}-6-chloro-2-fluorophenyl)acetamide
N-[(6-Amino-2-methyl(3-pyridyl))methyl]-2-(2-hydroxy-6-methyl-3-{[(3-methylphenyl)sulfonyl]amino}phenyl)acetamide; or
or a solvate, hydrate or pharmaceutically acceptable salt thereof.

12. A pharmaceutical composition, comprising a compound of claim 1 and a pharmaceutically-acceptable carrier.

13. A pharmaceutical composition, comprising a compound of claim 11 and a pharmaceutically-acceptable carrier.

14. A pharmaceutical composition according to claim 12, further comprising at least one of an anticoagulant, an antiplatelet agent or a thrombolytic agent.

15. A pharmaceutical composition according to claim 12, wherein said compound is present in an amount between about 0.1 and about 500 mg.

16. A method of inhibiting or treating aberrant thrombosis, ischemia, stroke, restenosis or inflammation in a mammal in need thereof, comprising administering to said mammal an effective amount of a compound of claim 1.

17. A method of inhibiting or treating thrombosis, ischemia, stroke, restenosis or inflammation in a mammal in need thereof, comprising administering to said mammal an effective amount of a compound of claim 11.

18. A method for the treatment of states characterized by abnormal venous or arterial thrombosis involving either thrombin production or action in a mammal in need thereof, comprising administering to said mammal a composition of claim 12.

19. A method for the treatment of states characterized by abnormal venous or arterial thrombosis involving either thrombin production or action in a mammal in need thereof, comprising administering to said mammal a composition of claim 13.

20. A method for the treatment of states characterized by abnormal venous or arterial thrombosis involving either thrombin production or action in a mammal in need thereof, comprising administering to said mammal a composition of claim 14.

21. A method for the treatment or prophylaxis of states characterized by abnormal venous or arterial thrombosis involving either thrombin production or action in a mammal in need thereof, comprising administering to said mammal a composition of claim 15.

22. A medical device for use in blood collection, blood storage or blood circulation, comprising a compound of any claim 1 embedded in or physically attached to said medical device.

23. A medical device according to claim 22, which is a catheter, stent, blood dialysis machine, blood collection syringe or tube, or a blood line.

24. A method of inhibiting the action of a proteolytic enzyme, wherein said proteolytic enzyme is a metalloprotease, acid protease, thiol protease or serine protease, comprising contacting said enzyme with a compound of claim 1.

25. A method according to claim 24, wherein said enzyme is leukocyte neutrophil elastase, chymotrypsin, trypsin, urokinase, plasminogen activator, pancreatic elastase, cathepsin G, thrombin or factor Xa.

26. A pharmaceutical composition according to claim 12 adapted for oral administration.

27. A pharmaceutical composition according to claim 13 adapted for oral administration.

28. A pharmaceutical composition according to claim 14 adapted for oral administration.

29. A pharmaceutical composition according to claim 15 adapted for oral administration.

30. A compound according to claim 1 wherein v is 2 to 5.

* * * * *

UNITED STATES PATENT AND TRADEMARK OFFICE
CERTIFICATE OF CORRECTION

PATENT NO. : 6,900,231 B2
DATED : May 31, 2005
INVENTOR(S) : Pan et al.

It is certified that error appears in the above-identified patent and that said Letters Patent is hereby corrected as shown below:

Column 1,
Line 30, delete "Sandier" and insert -- Sandler --.

Column 9,
Lines 24-25, delete "(=NH)–(CH$_2$)$_6$(=NH)–" and insert
-- –C(=NH)–(CH$_2$)$_6$–C(=NH)– --.
Line 25, delete "C(=O)+CH$_2$)$_6$–(=O)–" and insert -- –C(=O)–(CH$_2$)$_6$–C(=O)– --.

Column 65,
Line 2, delete "(s, 3)" and insert -- (s, 3H) --.

Column 71,
Line 47, delete "(R$^1$)$_2$CH(CH$_2$)$_5$NHC(O)" and insert -- (R$^1$)$_2$CH(CH$_2$)$_8$NHC(O) --.

Column 73,
Line 23, delete "preferably 2 to 5;".

Column 74,
Line 43, delete "aberrant".

Signed and Sealed this

Twenty-first Day of March, 2006

JON W. DUDAS
*Director of the United States Patent and Trademark Office*